US012564609B2

(12) United States Patent
Shizuru et al.

(10) Patent No.: US 12,564,609 B2
(45) Date of Patent: Mar. 3, 2026

(54) HEMATOPOIETIC STEM CELL ENGRAFTMENT WITH A COMBINATION OF AGENTS

(71) Applicant: The Board of Trustees of the Leland Stanford Junior University, Stanford, CA (US)

(72) Inventors: Judith A. Shizuru, Palo Alto, CA (US); Andriyana Krasimirova Bankova, Stanford, CA (US); Wendy W. Pang, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 580 days.

(21) Appl. No.: 18/031,536

(22) PCT Filed: Oct. 14, 2021

(86) PCT No.: PCT/US2021/054955
§ 371 (c)(1),
(2) Date: Apr. 12, 2023

(87) PCT Pub. No.: WO2022/081828
PCT Pub. Date: Apr. 21, 2022

(65) Prior Publication Data
US 2023/0310508 A1     Oct. 5, 2023

Related U.S. Application Data

(60) Provisional application No. 63/092,989, filed on Oct. 16, 2020.

(51) Int. Cl.
| | |
|---|---|
| *A61K 39/395* | (2006.01) |
| *A61K 31/00* | (2006.01) |
| *A61K 31/706* | (2006.01) |
| *A61K 35/28* | (2015.01) |
| *A61K 45/06* | (2006.01) |
| *A61P 35/00* | (2006.01) |
| *A61P 37/06* | (2006.01) |
| *C12N 5/0789* | (2010.01) |
| *A61K 39/00* | (2006.01) |

(52) U.S. Cl.
CPC ............ *A61K 35/28* (2013.01); *A61K 31/706* (2013.01); *A61K 39/3955* (2013.01); *A61K 45/06* (2013.01); *A61P 35/00* (2018.01); *A61P 37/06* (2018.01); *C12N 5/0647* (2013.01); *A61K 2039/505* (2013.01); *A61K 2039/545* (2013.01)

(58) Field of Classification Search
CPC .... A61K 39/3955; A61K 35/28; A61K 31/00; A61K 45/06; C07K 16/2803
See application file for complete search history.

(56) References Cited

U.S. PATENT DOCUMENTS

2013/0288303 A1     10/2013     Ng et al.
2017/0360954 A1*    12/2017     Nixon ................ A61K 47/6809

FOREIGN PATENT DOCUMENTS

WO     WO2020047164     3/2020

OTHER PUBLICATIONS

Bankova et al., Blood Adv., Oct. 12, 2021, vol. 5(19):3900-3912.*
Bankova et al. (2021) 5-Azacytidine depletes HSCs and synergizes with an anti-CD117 antibody to augment donor engraftment in immunocompetent mice, Blood Advances, vol. 5, No. 19, pp. 3900-3912.

* cited by examiner

*Primary Examiner* — Xiaozhen Xie
(74) *Attorney, Agent, or Firm* — Pamela J. Sherwood; Bozicevic, Field & Francis LLP

(57)     ABSTRACT

The present invention provides a clinically applicable method of bone marrow conditioning for stem cell transplantation or therapeutic treatment of hematologic malignancies.

20 Claims, 41 Drawing Sheets

HEMATOPOIETIC STEM CELL ENGRAFTMENT WITH A COMBINATION OF AGENTS

CROSS REFERENCE TO RELATED APPLICATION

The present application claims the benefit of and priority to U.S. Provisional Patent Application No. 63/092,989, filed Oct. 16, 2020, the entire disclosure of which is hereby.

STATEMENT REGARDING FEDERALLY SPONSORED RESEARCH

This invention was made with Government support contract HL 152830 awarded by the National Institutes of Health. The Government has certain rights in the invention.

BACKGROUND

Hematopoietic cell transplantation (HCT) utilizes stem cell replacement therapy to provide curative options for many life-threatening malignant and non-malignant blood disorders. However, the toxicity of the conditioning regimens used to achieve engraftment of allogeneic donor or autologous gene corrected hematopoietic stem cells (HSC) continues to be a major obstacle to the safe and more widespread use of HCT. For decades, conditioning of recipients for transplant has relied on DNA-damaging alkylator chemotherapy or radiation to deplete endogenous stem cells and clear hematopoietic niche space necessary for donated HSC to engraft. The development of targeted and less toxic methods to eliminate host HSC would substantially reduce the morbidity and mortality of HCT, thereby expanding the scope of the diseases treated, and allowing many more patients to undergo this life-saving procedure which is currently thought to be too high risk.

Targeted HSC depletion methods have been developed using a monoclonal antibody (mAb) that recognizes CD117 (c-Kit), a receptor tyrosine kinase present on hematopoietic stem and progenitor cells (HSPC). An anti-human CD117 mAb, JSP191 (formerly AMG 191), can eliminate HSC with little to no off-target toxicity in non-human primates. Furthermore, a Phase 1 clinical trial using JSP191 as the sole conditioning agent for patients undergoing HCT for severe combined immunodeficiency (SCID) has demonstrated that the antibody can clear HSC niche space permitting donor HSC engraftment, and result in robust, nascent T cell reconstitution.

The interaction between CD117 with its ligand, stem cell factor (SCF), is fundamentally important for HSC survival, proliferation and differentiation within the stem cell niche. It is known that the anti-mouse CD117 mAb, ACK2, can efficiently deplete host hematopoietic cells and permit engraftment of donor HSC in lymphocyte deficient mice. However, the potency of ACK2 is significantly reduced in enabling engraftment of congenic HSC in wildtype immunocompetent mice. The reasons for this higher engraftment resistance to anti-CD117 mAb conditioning is unclear, but may reflect differences that exist in the bone marrow environment of immune deficient vs wildtype mice.

CD117 is also expressed on disease initiating HSC present on human myelodysplastic syndrome (MDS) and secondary acute myeloid leukemia (AML), and in mice xenografted with human MDS or AML HSC, anti-human CD117 mAbs can deplete these cells. Hence, there is a desire to potentiate the effect of naked anti-CD117 mAbs to permit the targeted elimination of host HSC for a range of different immune competent BM states, from monogenic disorders such as the hemoglobinopathies, to BM containing clonal malignant HSC. To date, strategies shown to enhance the potency of anti-CD117 mAb HSC ablation include the generation of antibody drug conjugates (ADC), or combining anti-CD117 mAbs with low dose irradiation or with agents that block the macrophage check point inhibitor CD47.

Improved methods for engraftment of stem cells, including hematopoietic stem cells, are of great clinical interest. The present invention addresses this need.

SUMMARY OF THE INVENTION

Methods and compositions are provided for the long term multilineage engraftment of hematopoietic stem cells in a recipient, by: treating the recipient with a pre-transplantation non-myeloablative conditioning regimen comprising an effective dose of an agent specific for CD117 (referred to as an anti-CD117 agent) and an effective dose of a hypomethylating agent, e.g. a cytosine analog; and administering an effective dose of a cell population comprising exogenous stem cells. The methods allow engraftment to treat, for example, hematologic disorders. In some embodiments the combination of agents provides for a synergistic improvement in the effectiveness of the engraftment process relative to either of the agents administered as a single agent.

Endogenous hematopoietic stem cells are depleted by the conditioning regimen. Conditioning agents that deplete endogenous hematopoietic stem cells comprise a combined regimen of an agent specific for CD117 and a hypomethylating agent. These agents are also capable of depleting the exogenous stem cells after administration, and the methods can utilize a "wash-out" period, from the time the conditioning agents are administered to the time the exogenous stem cells are administered. The wash-out period is sufficient to reduce the serum levels of the conditioning agents that deplete endogenous stem cells to a non-toxic level, which does not result in depletion of the exogenous stem cells.

In some embodiments the anti-CD117 agent is an antibody that specifically binds to human CD117. In some embodiments the antibody is a humanized monoclonal antibody, which may be an aglycosylated IgG antibody. In some embodiments, a single dose of the anti-CD117 agent is administered prior to transplantation. In some embodiments the dose of agent is delivered by intravenous infusion. The effective dose of the antibody agent may be up to about 25 mg/kg, up to about 15 mg/kg, up to about 10 mg/kg; up to about 5 mg/kg; up to about 1 mg/kg; up to about 0.1 mg/kg. In some embodiments an antibody dose is from about 0.1 mg/kg to about 25 mg/kg, from about 0.5 mg/kg to about 15 mg/kg, from about 1 to about 5 mg/kg.

In other embodiments the anti-CD117 agent is a molecule that binds to CD117 including, without limitation, stem cell factor (SCF) or a variant thereof. Where the molecule is SCF, it may be conjugated to a cytotoxic moiety. Alternatively, a variant of SCF may be used, e.g. where the variant binds to CD117 but does not elicit signaling through this receptor. In some embodiments the agent specific for CD117 is a small molecule, e.g. a small molecule that binds to CD117 but does not elicit signaling through this receptor. Such a variant or small molecule may block the interaction between SCF and CD117.

In some embodiments the hypomethylating agent blocks the activity of DNA methyltransferase. In some embodiments the hypomethylating agent is a cytosine analog. In some embodiments a cytosine analog is one or more of 5-azacytidine, decitabine, guadecitabine, 5-Fluro-2'-de-oxycytidine, etc. In some embodiments the hypomethylating agent is 5-azacytidine. In some embodiments the hypom-ethylating agent is administered of a period of time, e.g. daily for a period of from about 1 to about 9 days, from about 1 to about 7 days, from about 1 to about 6 days, and may be for about 5 days. In some embodiments the hypom-ethylating agent is administered from about 1 to 14 days, and maybe for about 1 to 21 days. The effective daily dose of a hypomethylating agent may be, for example, up to 10 mg/kg, up to about 5 mg/kg, up to about 2.5 mg/kg; up to about 1 mg/kg; up to about 0.5 mg/kg; up to about 0.1 mg/kg. In some embodiments the effective daily dose is from about 0.1 mg/kg to about 10 mg/kg, from about 0.5 mg/kg to about 5 mg/kg, from about 1 to about 2.5 mg/kg.

In some embodiments the hypomethylating agent is administered subsequent to the administration of the anti-CD117 agent, in other embodiments the administration is concomitant. In some embodiments the interval of time between administration of the anti-CD117 agent and the hypomethylating agent is at least 1 day, at least 2 days, at least 3 days, at least 4 days, at least 5 days, for example between about 1 and 10 days, between about 2 and 8 days, between about 3 and 5 days.

The infusion of hematopoietic stem and progenitor cells (HSPC) to provide exogenous stem cells may be performed when the dose of hypomethylating agent is completed, e.g. concomitant with the final dose, after about 12 hours, after about 24 hours after about 18 hours, after about 2 days, after about 3 days, after about 5 days, and usually after not more than 10 days.

In some embodiments HSPC are obtained from a donor hematopoietic cell sample. In some embodiments the hema-topoietic cell sample is bone marrow. In some embodiments the HSPC are obtained from umbilical cord blood. In some embodiments, the hematopoietic cell sample is obtained by apheresis from donor mobilized peripheral blood. In some embodiments the HSPC are generated in vitro. The HSPC donor may be allogeneic or autologous, for example where the HSPC are genetically engineered by introduction or deletion of genetic material prior to re-infusion, for example during ex vivo culture. Allogeneic donors may be MHC matched to the recipient. The donor may be haploidentical or not haplo-identical to the recipient. The donor may be mismatched at one or more MHC loci, e.g. mismatched at 1, 2, 3, 4, 5 or 6 of the major loci for MHC matching.

The HSPC are optionally isolated from the hematopoietic cell sample for expression of CD34. The isolation may optionally comprise selection for expression of CD90. HSPC that are purified may be at least about 45% pure, as defined by the percentage of cells that are CD34$^+$ in the population, may be at least about 50% pure, at least about 60% pure, at least about 70% pure, at least about 80% pure, at least about 90% pure. The effective dose of CD34$^+$ cells may be from about $10^5$ to about $10^7$ CD34$^+$ cells/kg of recipient body weight, and may be at least about $5\times10^5$ CD34$^+$ cells/kg of recipient body weight, at least about $10^6$ CD34+ cells/kg of recipient body weight, at least about $5\times10^6$ CD34$^+$ cells/kg of recipient body weight, at least about $10\times10^6$ CD34$^+$ cells/kg of recipient body weight, and may be $5\times10^7$ CD34+ cells/kg of recipient body weight or more.

In some embodiments, the transplantation is performed in the absence of myeloablative conditioning. In some embodi-ments the recipient is immunocompetent. The administra-tion of the pre-transplantation conditioning regimen is repeated as necessary to achieve the desired level of abla-tion. Following transplantation with donor stem cells, the recipient may be a chimera or mixed chimera with respect to the donor cells.

In one embodiment of the invention, the stem cells are one or more of autologous hematopoietic stem cells, genetically modified hematopoietic stem cells, and allogeneic hema-topoietic stem cells, for example and without limitation allogeneic or genetically modified autologous cells. Such stem cells find use in the treatment of a variety of blood disorders, e.g. genetic disorders including aplastic anemia; sickle cell disease; thalassemias; severe immunodeficiency; bone marrow failure states, immune deficiencies, hemoglo-binopathies, leukemias, lymphomas, immune-tolerance induction, genetic disorders treatable by bone marrow trans-plantation and other blood disorders, and the like. Alloge-neic stem cells find use, for example and without limitation, in the treatment of hematologic malignancies, i.e. cancers and myelodysplastic syndromes, e.g. AML, MDS, CMML, multiple myeloma, CML, NHL, and the like, or non-malig-nant genetic disorders treatable by bone marrow transplan-tation such as cell disease; thalassemias; severe immunode-ficiency, neurologic disorders and the like. The methods of the invention are also useful in the induction of tolerance in a patient, for example tolerance to donor tissue, e.g. in organ transplants; tolerance to autoantigens, e.g. in the context of treatment of autoimmune disease; and the like.

In one embodiment of the invention, a method is provided for inducing tolerance in a patient, comprising administering to a patient administration of an agent that targets stem cells, including without limitation an antibody specific for c-kit and a hypomethylating agent. Following the conditioning regimen, the recipient is infused with an effective dose of hematopoietic stem and progenitor cells, thereby providing immune tolerance to the donor cells for future organ trans-plants.

In other embodiments the combination of an anti-CD117 agent and a hypomethylating agent as disclosed above is utilized for therapeutic treatment of malignancies in the absence of transplantation. For myeloid malignancies, elimi-nation of leukemic stem cells (LSC) is essential for disease eradication. Such conditions include, without limitation, cancers and myelodysplastic syndromes, e.g. AML, MDS, CMML, multiple myeloma, CML, NHL, etc. Despite the disease-modifying effects of AZA in these patients, single agent AZA is insufficient to eliminate LSC and therefore does not achieve durable remissions. The combination therapy disclosed herein provides substantial efficacy in the synergistic targeting of LSC.

Additional agents useful in the conditioning regimen for transplantation, or for therapeutic treatment in the absence of transplantation may include, without limitation, biologic agents that enhance the HSC depleting activity of anti-CD117 antibodies, e.g., anti-CD47 antibodies; antibodies that target progenitor cells, e.g., anti-CD38 antibodies; che-motherapy agents that deplete HSC, e.g., busulfan, cyclo-phosphamide; small molecules that inhibit c-Kit tyrosine kinase activity, e.g, imatinib, midostaurin; agents that work synergistically with HMAs, e.g., venetoclax, anti-CD70; and agents that target leukemic cells, e.g. gilteritinib; and the like.

BRIEF DESCRIPTION OF THE FIGURES

Figure 17:
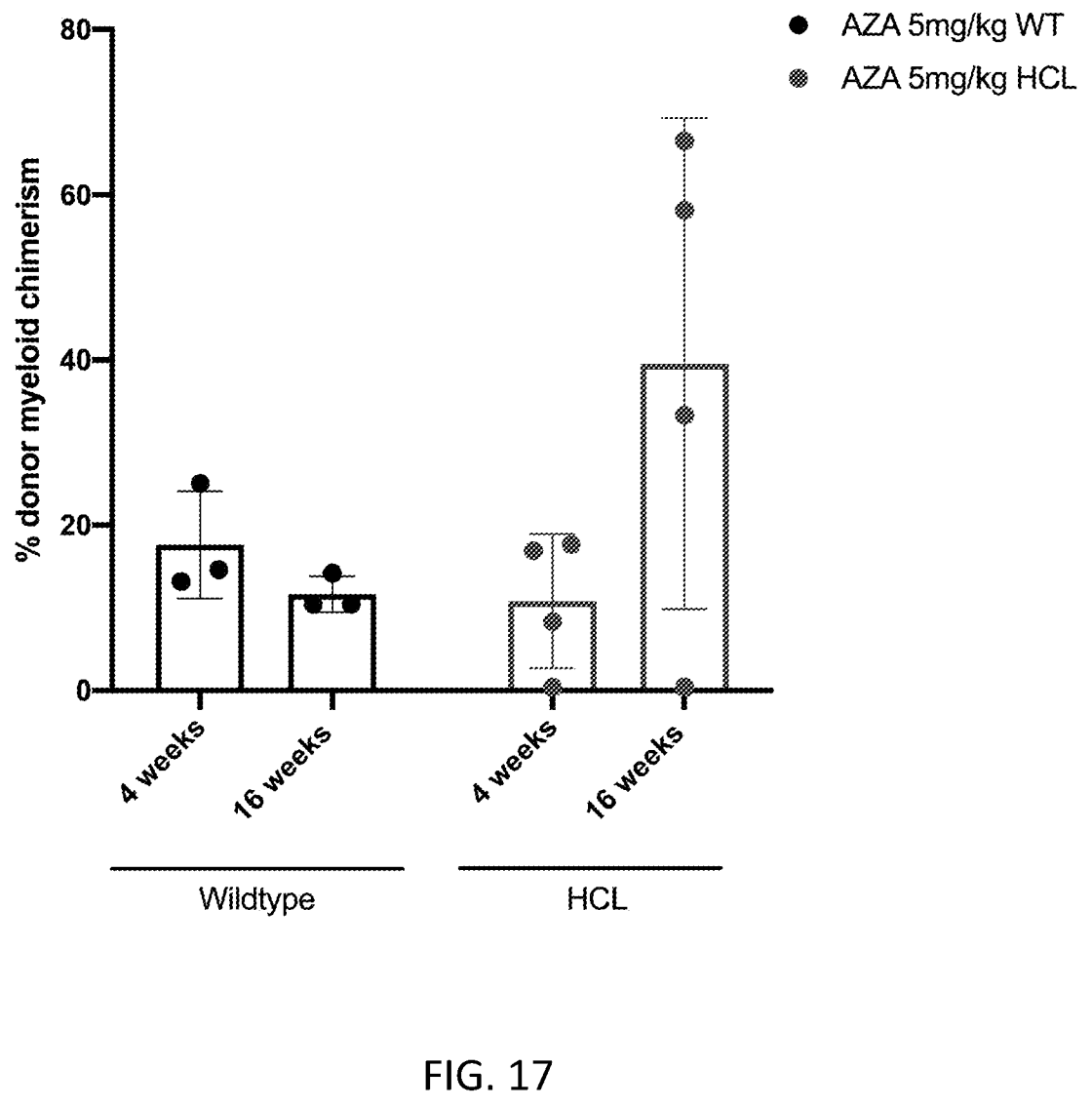

FIG. 17 shows AZA shows therapeutic activity in mouse model of HCL. Wildtype and HCL mice were treated with AZA 5 mg/kg for 5 days following by transplantation of donor hematopoietic cells. % myeloid donor chimerism was assessed by flow cytometry at 4- and 16-weeks post transplantation.

DETAILED DESCRIPTION OF THE EMBODIMENTS

Figure 1:
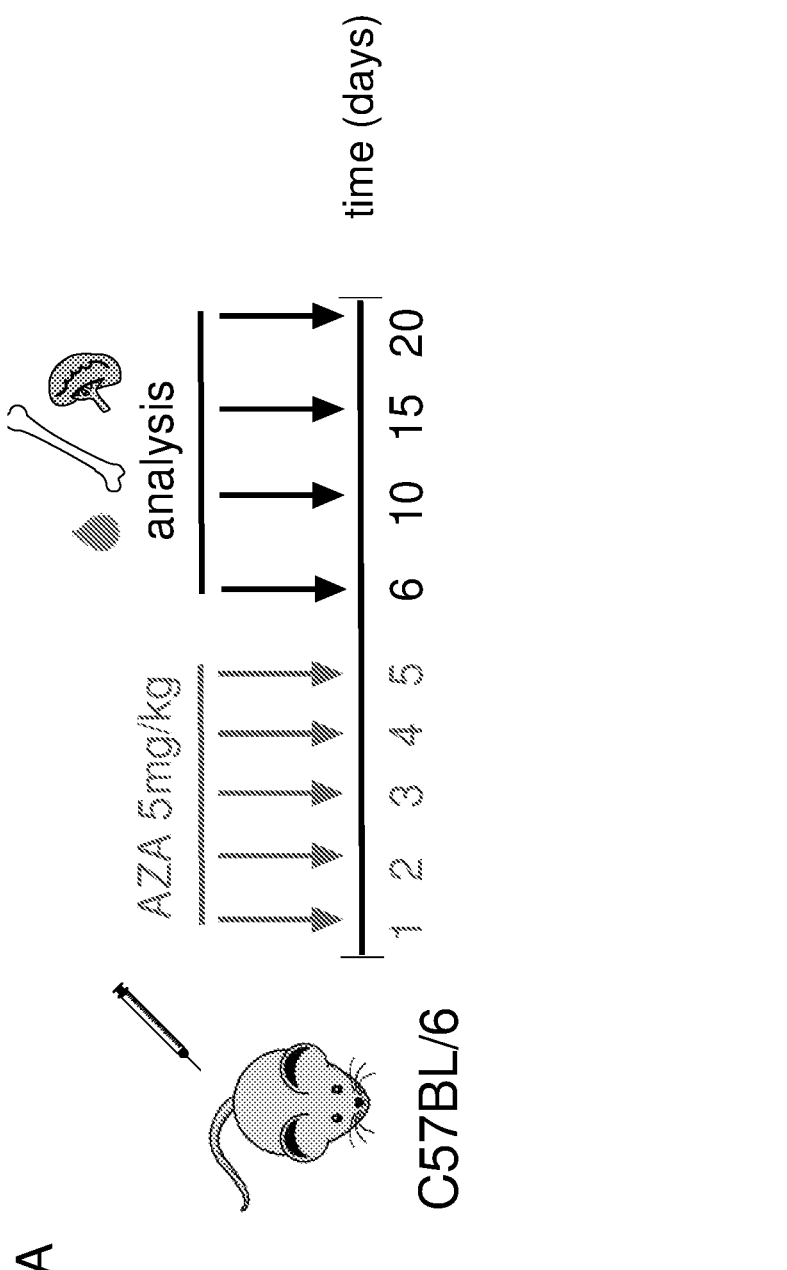
FIG. 1 shows 5-Azacytidine depletes hematopoietic stem and progenitor cells in vivo. A. Schematic of treatment protocol. C57BL/6 mice were injected with 5-Azacytidine (AZA) in dose 5 mg/kg/d for 5 consecutive days. Peripheral blood, bone marrow (BM) and spleen were analyzed on days 6, 10 and 15 and 20 after start AZA treatment. B. Peripheral blood cell counts in untreated mice as compared to AZA-treated mice at day 6, 10 and 20 following AZA treatment. Hemoglobin (Hb); white blood cells (WBC). C. Total live cells in bone marrow (BM) and spleen of untreated mice and AZA-treated mice at day 6, 10, 15 and 20 after start AZA treatment. D. Hematoxylin and eosin staining of bone marrow section from mouse femur at day 6 after treatment with AZA 5 mg/kg/d for 5 days as compared to untreated control. Magnification 100 μm. E. Representative flow cytometric analysis of the hematopoietic stem and progenitor cell (HSPC) compartment in the BM of untreated and AZA-treated mice at day 6, 10, 15 and 20. The figure shows the gating strategy beginning with lineage negative (Lin⁻) live cells. Lin⁻Sca1⁺c-Kit⁺ cells (LSK), multipotent progenitors (MPP), long-term hematopoietic stem cells (LT-HSC), short-term HSC (ST-HSC). F. Absolute number of the different HSPC compartments at day 6, 10, 15 and 20 after start of AZA treatment as compared to untreated control mice. Lin⁻Sca1⁺c-Kit⁺ (LSK); LSKCD150⁺CD48⁻ (LT-HSC), LSKCD150⁻CD48⁻ (ST-HSC), LSKCD150⁺CD48⁺ (MPP2), LSKCD150⁻CD48⁺Flt3⁻ (MPP3), LSKCD150⁻CD48⁺Flt3⁺ (MPP4). Data in (B), (C) and (F) represent mean±SD (n=4 per group per timepoint). Statistics were calculated with Mann-Whitney test (*P<0.05).
Figure 1:
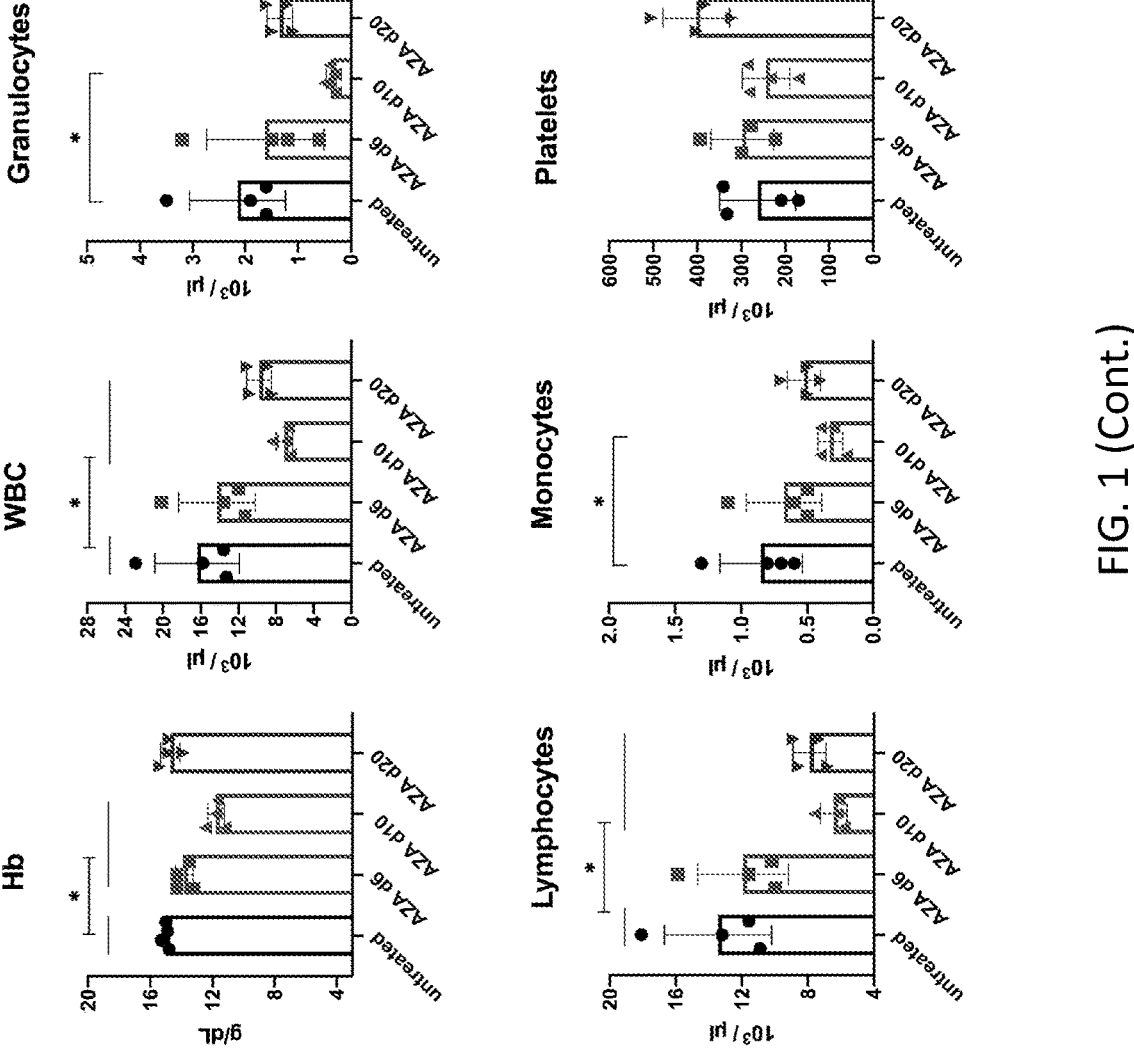
Figure 1:
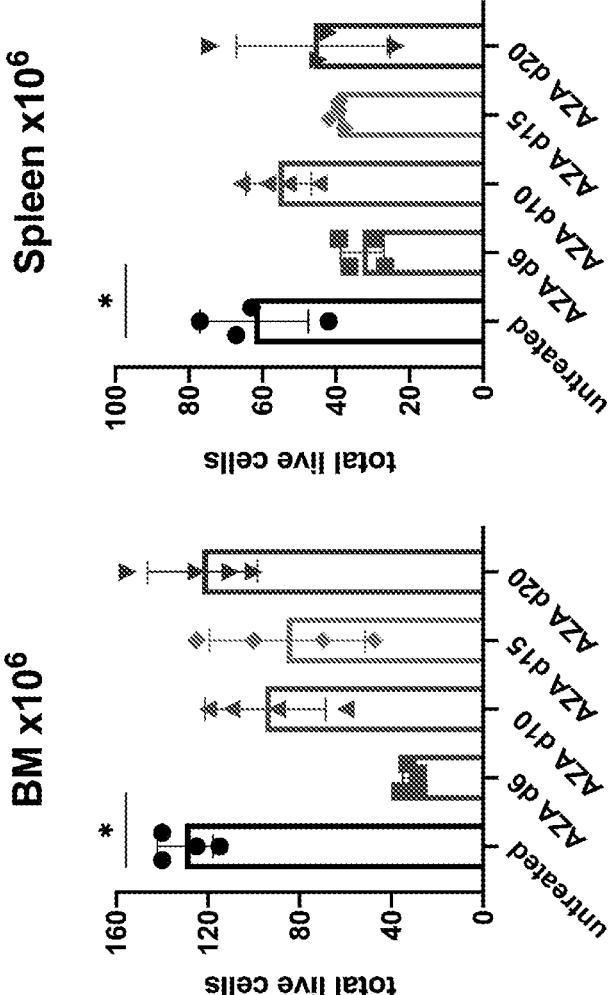
Figure 1:
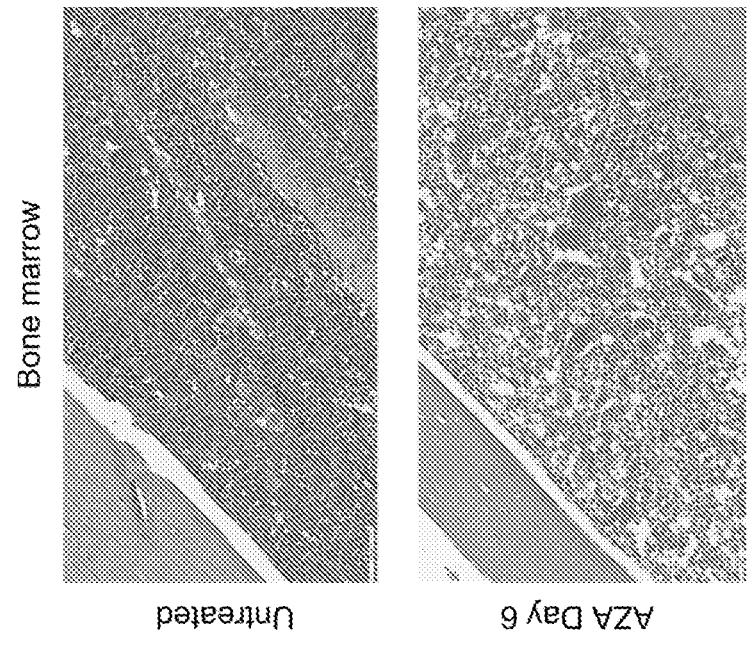
Figure 1:
Figure 1:
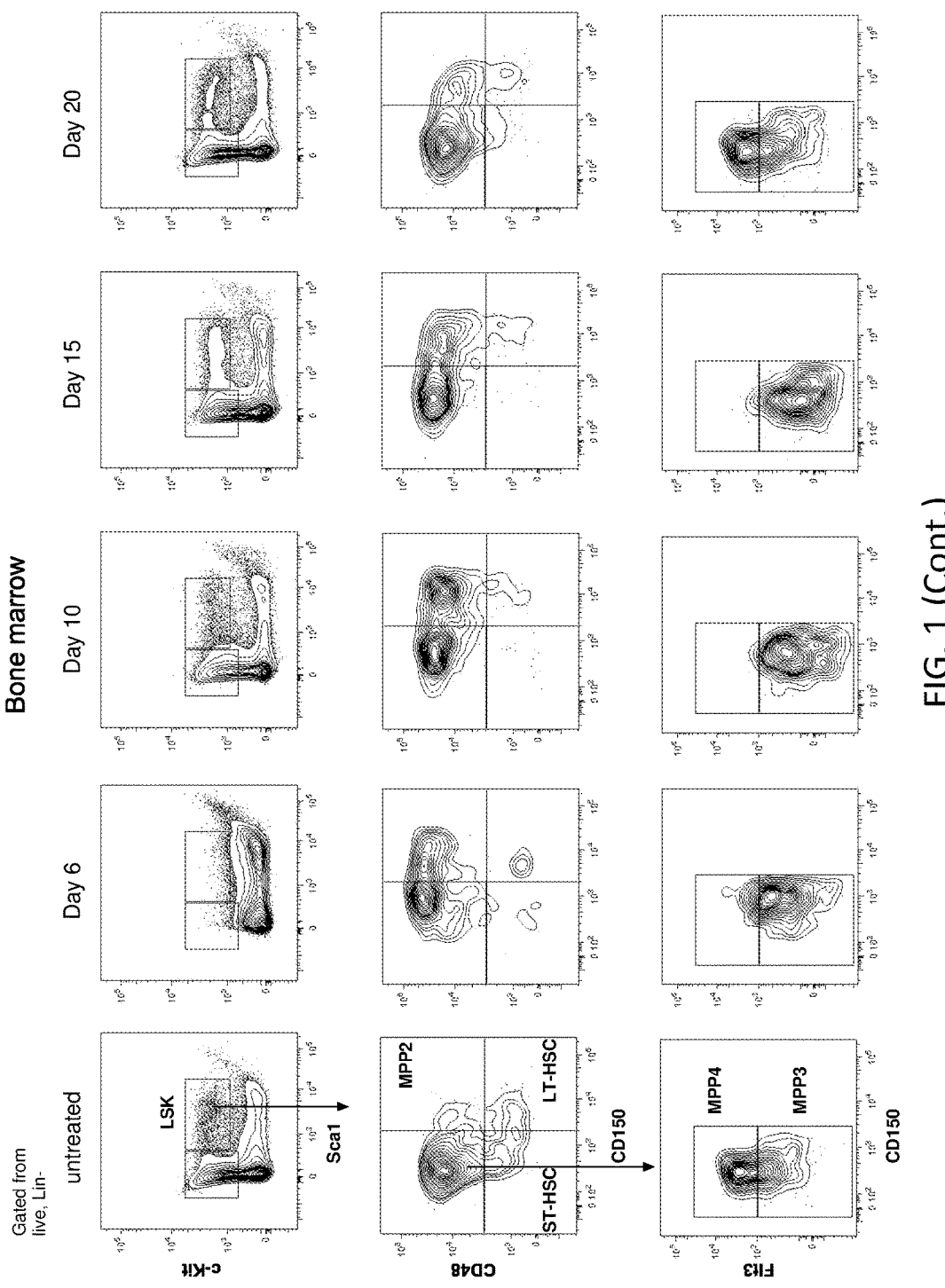
Figure 1:
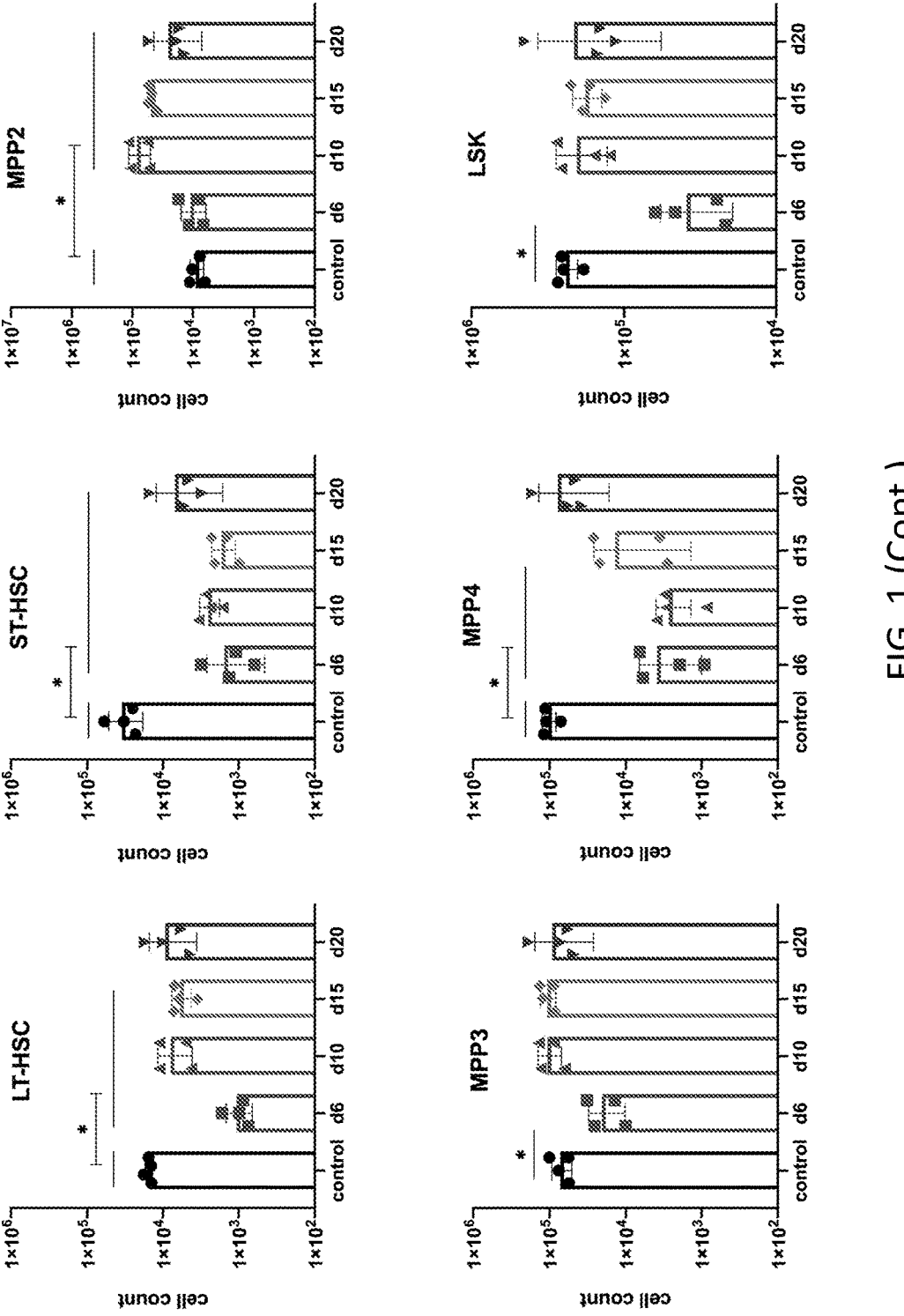

Methods are provided for the engraftment of stem cells in a subject by treatment with a combined regimen of an anti-CD117 agent and a hypomethylating agent prior to infusion of a cellular composition comprising the stem and progenitor cells.

It is an objective of the present invention to provide a clinically applicable method of stem cell transplantation that facilitates engraftment and reconstitutes immunocompetence of the recipient without requiring myeloablative conditioning, or development of graft-vs-host disease (GVHD) or graft rejection.

Aspects of the present invention are based on the discovery that a depletion of the endogenous stem cell niche that facilitates efficient engraftment of hematopoietic stem cells (HSCs) is accomplished by combining the use of an agent that targets the endogenous stem cells, e.g. anti-CD117 antibody, with a hypomethylating agent. In particular, the present invention combines this improved selective ablation of endogenous stem cells with the administration to the recipient of exogenous stem cells, resulting in efficient, long-term engraftment and tolerance.

It is to be understood that this invention is not limited to the particular methodology, products, apparatus and factors described, as such methods, apparatus and formulations may, of course, vary. It is also to be understood that the terminology used herein is for the purpose of describing particular embodiments only, and is not intended to limit the scope of the present invention which will be limited only by appended claims.

It must be noted that as used herein and in the appended claims, the singular forms "a," "and," and "the" include plural referents unless the context clearly dictates otherwise. Thus, for example, reference to "a drug candidate" refers to one or mixtures of such candidates, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, formulations and methodologies which are described in the publication and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

Generally, conventional methods of protein synthesis, recombinant cell culture and protein isolation, cell engineering with synthetic messenger RNA, recombinant DNA techniques, and genome editing within the skill of the art are employed in the present invention, including, for example, programmable gene editing tools. For additional information related to programmable gene editing tools (e.g., CRISPR/Cas RNA-guided proteins such as Cas9, CasX, CasY, and Cpf1, Zinc finger proteins such as Zinc finger nucleases, TALE proteins such as TALENs, CRISPR/Cas guide RNAs, PAMs, and the like) refer to, for example, Dreier, et al., (2001) J Biol Chem 276:29466-78; Dreier, et al., (2000) J Mol Biol 303:489-502; Liu, et al., (2002) J Biol Chem 277:3850-6); Dreier, et al., (2005) J Biol Chem 280:35588-97; Jamieson, et al., (2003) Nature Rev Drug Discov 2:361-8; Durai, et al., (2005) Nucleic Acids Res 33:5978-90; Segal, (2002) Methods 26:76-83; Porteus and Carroll, (2005) Nat Biotechnol 23:967-73; Pabo, et al., (2001) Ann Rev Biochem 70:313-40; Wolfe, et al., (2000) Ann Rev Biophys Biomol Struct 29:183-212; Segal and Barbas, (2001) Curr Opin Biotechnol 12:632-7; Segal, et al., (2003) Biochemistry 42:2137-48; Beerli and Barbas, (2002) Nat Biotechnol 20:135-41; Carroll, et al., (2006) Nature Protocols 1:1329; Ordiz, et al., (2002) Proc Natl Acad Sci USA 99:13290-5; Guan, et al., (2002) Proc Natl Acad Sci USA 99:13296-301; Sanjana et al., Nature Protocols, 7:171-192 (2012); Zetsche et al., Cell. 2015 Oct. 22; 163(3):759-71; Makarova et al, Nat Rev Microbiol. 2015 November; 13(11):722-36; Shmakov et al., Mol Cell. 2015 Nov. 5; 60(3):385-97; Jinek et al., Science. 2012 Aug. 17; 337(6096):816-21; Chylinski et al., RNA Biol. 2013 May; 10(5):726-37; Ma et al., Biomed Res Int. 2013; 2013:270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 September; 31(9):839-43; Qi et al, Cell. 2013 Feb. 28; 152(5):1173-83; Wang et al., Cell. 2013 May 9; 153(4):910-8; Auer et. al., Genome Res. 2013 Oct. 31; Chen et. al., Nucleic Acids Res. 2013 Nov. 1; 41(20):e19; Cheng et. al., Cell Res. 2013 October; 23(10):1163-71; Cho et. al., Genetics. 2013 November; 195(3):1177-80; DiCarlo et al., Nucleic Acids Res. 2013 April; 41(7):4336-43; Dickinson et. al., Nat Methods. 2013 October; 10(10):1028-34; Ebina et. al., Sci Rep. 2013; 3:2510; Fujii et. al, Nucleic Acids Res. 2013 Nov. 1; 41(20):e187; Hu et. al., Cell Res. 2013 November; 23(11):1322-5; Jiang et. al., Nucleic Acids Res. 2013 Nov. 1; 41(20):e188; Larson et. al., Nat Protoc. 2013 November; 8(11):2180-96; Mali et. al., Nat Methods. 2013 October; 10(10):957-63; Nakayama et. al., Genesis. 2013 December; 51(12):835-43; Ran et. al., Nat Protoc. 2013 November; 8(11):2281-308; Ran et. al., Cell. 2013 Sep. 12; 154(6): 1380-9; Upadhyay et. al., G3 (Bethesda). 2013 Dec. 9;

3(12):2233-8; Walsh et. al., Proc Natl Acad Sci USA. 2013 Sep. 24; 110(39):15514-5; Xie et. al., Mol Plant. 2013 Oct. 9; Yang et. al., Cell. 2013 Sep. 12; 154(6):1370-9; Briner et al., Mol Cell. 2014 Oct. 23; 56(2):333-9; Burstein et al., Nature. 2016 Dec. 22—Epub ahead of print; Gao et al., Nat Biotechnol. 2016 Jul. 34(7):768-73; Shmakov et al., Nat Rev Microbiol. 2017 March; 15(3):169-182; as well as international patent application publication Nos. WO2002099084; WO00/42219; WO02/42459; WO2003062455; WO03/080809; WO05/014791; WO05/084190; WO08/021207; WO09/042186; WO09/054985; and WO10/065123; U.S. patent application publication Nos. 20030059767, 20030108880, 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; 20140377868; 20150166983; and 20160208243; and U.S. Pat. Nos. 6,140,466; 6,511,808; 6,453,242 8,685,737; 8,906, 616; 8,895,308; 8,889,418; 8,889,356; 8,871,445; 8,865, 406; 8,795,965; 8,771,945; and 8,697,359; all of which are hereby incorporated by reference in their entirety.

Definitions

Conditioning regimen. Patients undergoing an allogeneic hemopoietic stem cell transplant (HSCT), are prepared with a so-called conditioning regimen that can suppress the recipient's immune system and deplete endogenous stem cells, in order to allow engraftment of the donor stem cells.

The intensity of conventional conditioning regimens can vary significantly. Description of the regimens can refer to genotoxic or non-genotoxic regimens, which may overlap with reference to myeloablative or non-myeloablative regimens. See, for example, Bacigalupo et al. (2009) Biol Blood Marrow Transplant. 15(12):1628-1633, herein specifically incorporated by reference.

Myeloablative conditioning regimens are combination of agents expected to produce profound pancytopenia and myeloablation within 1-3 weeks from administration; pancytopenia is long lasting, usually irreversible and in most instances fatal, unless hematopoiesis is restored by hemopoietic stem cell infusion. Examples include total body irradiation and/or administration of high doses of alkylating agents; busulfan, melphalan, cyclophosphamide; etc.

Non-myeloablative conditioning regiments typically cause minimal cytopenia, and little early toxicity, but are immunosuppressive to the extent that, when followed by administration of an effective dose of HSPC, will result in engraftment of donor lympho-hemopoietic stem cells.

In certain embodiments the conditioning regimens provided herein are non-myeloablative, and utilize agents for depletion of endogenous cells that prevent engraftment without causing log-lasting pancytopenia. In other embodiments, including without limitation combinations with additional chemotherapeutic agents, there may be an ablative effect, or a reduced intensity conditioning (RIC) effect.

"Concomitant administration" of active agents in the methods of the invention means administration with the reagents at such time that the agents will have a therapeutic effect at the same time. Such concomitant administration may involve concurrent (i.e. at the same time), prior, or subsequent administration of the agents. A person of ordinary skill in the art would have no difficulty determining the appropriate timing, sequence and dosages of administration for particular drugs and compositions of the present invention.

Stem cell markers. Exemplary markers for antibody mediated ablation of human hematopoietic stem cells include CD34; CD90 (thy-1); CD59; CD110 (c-mpl); c-kit (CD-117); etc. In one embodiment of the invention, the marker for depletion is c-kit (CD117). CD117 is a receptor tyrosine kinase type III, which binds to stem cell factor (a substance that causes certain types of cells to grow), also known as "steel factor" or "c-kit ligand". When this receptor binds to stem cell factor (SCF) it forms a dimer that activates its intrinsic tyrosine kinase activity, that in turn phosphorylates and activates signal transduction molecules that propagate the signal in the cell. See, for example, the human refseq entries Genbank NM_000222; NP_000213. CD117 is an important cell surface marker used to identify certain types of hematopoietic (blood) progenitors in the bone marrow. Hematopoietic stem cells (HSC), multipotent progenitors (MPP), and common myeloid progenitors (CMP) express high levels of CD117. A number of antibodies that specifically bind human CD117 are known in the art and commercially available, including without limitation SR1, 2B8, ACK2, YB5-B8, 57A5, 104D2, etc. Of interest is the humanized form of SR1, AMG 191, described in U.S. Pat. Nos. 8,436,150, and 7,915,391 which is an aglycosylated IgG1 humanized antibody.

An effective dose of an anti-CD117 antibody may be administered in one or more doses, including a single dose, which may be at least about one week prior to transplantation, at least about 5 days prior to transplantation, at least about 3 days prior to transplantation. The period of time between dosing and transplantation is sufficient to substantially eliminate the anti-CD117 antibody from the circulation of the recipient. For example the decrease in peak serum levels following administration is usually the time sufficient for the level to decrease as least about 10-fold from peak levels, usually at least about 100-fold, 1000-fold, 10,000-fold, or more. It is preferable to introduce the donor stem cells within the empty niche "window" following the washout period, usually within about 3 days, about 2 days, about 1 day, or at the time of clearance.

In some embodiments, an effective dose of an anti-CD117 antibody is up to about 25 mg/kg, up to about 15 mg/kg, up to about 10 mg/kg; up to about 5 mg/kg; up to about 1 mg/kg; up to about 0.1 mg/kg. In some embodiments an antibody dose is from about 0.1 mg/kg to about 25 mg/kg, from about 0.5 mg/kg to about 15 mg/kg, from about 1 to about 5 mg/kg; where the dose may vary with the specific antibody and recipient.

As used herein, "antibody" includes reference to an immunoglobulin molecule immunologically reactive with a particular antigen, and includes both polyclonal and monoclonal antibodies. The term also includes genetically engineered forms such as chimeric antibodies (e.g., humanized murine antibodies) and heteroconjugate antibodies. The term "antibody" also includes antigen binding forms of antibodies, including fragments with antigen-binding capability (e.g., Fab', F(ab')$_2$, Fab, Fv and rIgG. The term also refers to recombinant single chain Fv fragments (scFv). The term antibody also includes bivalent or bispecific molecules, diabodies, triabodies, and tetrabodies. The term "entire" antibody is used to refer to an antibody comprising both variable regions and constant regions, i.e. an Fc region.

Selection of antibodies for endogenous stem cell ablation and transient immunosuppression may be based on a variety of criteria, including selectivity, affinity, cytotoxicity, etc. The phrase "specifically (or selectively) binds" to an antibody or "specifically (or selectively) immunoreactive with," when referring to a protein or peptide, refers to a binding reaction that is determinative of the presence of the protein, in a heterogeneous population of proteins and other biologics. Thus, under designated immunoassay conditions, the specified antibodies bind to a particular protein sequences at least two times the background and more typically more than 10 to 100 times background. In general, antibodies of the present invention bind antigens on the surface of target cells in the presence of effector cells (such as natural killer cells or macrophages). Fc receptors on effector cells recognize bound antibodies. The cross-linking of Fc receptors signals the effector cells to kill the target cells by cytolysis or apoptosis. In one embodiment, the induction is achieved via antibody-dependent cellular cytotoxicity (ADCC). In alternative embodiments, the antibodies are active in growth inhibition of the targeted cells, an ablation is achieved by interfering with growth factor signaling, e.g. antibodies specific for growth factor receptors such as c-kit.

"Affinity" refers to the strength of binding, increased binding affinity being correlated with a lower KD. In an embodiment, affinity is determined by surface plasmon resonance (SPR), e.g. as used by Biacore systems. The affinity of one molecule for another molecule is determined by measuring the binding kinetics of the interaction, e.g. at 25° C.

An antibody immunologically reactive with a particular antigen can be generated by recombinant methods such as selection of libraries of recombinant antibodies in phage or similar vectors, or by immunizing an animal with the antigen or with DNA encoding the antigen. Methods of preparing polyclonal antibodies are known to the skilled artisan. The antibodies may, alternatively, be monoclonal antibodies. Monoclonal antibodies may be prepared using hybridoma methods. In a hybridoma method, an appropriate host animal is typically immunized with an immunizing agent to elicit lymphocytes that produce or are capable of producing antibodies that will specifically bind to the immunizing agent. Alternatively, the lymphocytes may be immunized in vitro. The lymphocytes are then fused with an immortalized cell line using a suitable fusing agent, such as polyethylene glycol, to form a hybridoma cell.

Human antibodies can be produced using various techniques known in the art, including phage display libraries. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire.

Antibodies also exist as a number of well-characterized fragments produced by digestion with various peptidases. Thus, pepsin digests an antibody below the disulfide linkages in the hinge region to produce F(ab)'$_2$, a dimer of Fab which itself is a light chain joined to V$_H$-C$_{H1}$ by a disulfide bond. The F(ab)'$_2$ may be reduced under mild conditions to break the disulfide linkage in the hinge region, thereby converting the F(ab)'2 dimer into an Fab' monomer. The Fab' monomer is essentially Fab with part of the hinge region. While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries.

A "humanized antibody" is an immunoglobulin molecule that contains minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally also will comprise at least a portion of an immunoglobulin constant region (Fc), typically that of a human immunoglobulin.

Antibodies of interest for ablation may be tested for their ability to induce ADCC (antibody-dependent cellular cytotoxicity). Antibody-associated ADCC activity can be monitored and quantified through detection of either the release of label or lactate dehydrogenase from the lysed cells, or detection of reduced target cell viability (e.g. annexin assay). Assays for apoptosis may be performed by terminal deoxynucleotidyl transferase-mediated digoxigenin-11-dUTP nick end labeling (TUNEL) assay (Lazebnik et al., Nature: 371, 346 (1994). Cytotoxicity may also be detected directly by detection kits known in the art, such as Cytotoxicity Detection Kit from Roche Applied Science (Indianapolis, Ind.). Preferably, the antibodies of the present invention induce at least 10%, 20%, 30%, 40%, 50%, 60%, or 80% cytotoxicity of the target cells.

In some embodiments, the antibody is conjugated to an effector moiety. The effector moiety can be any number of molecules, including labeling moieties such as radioactive labels or fluorescent labels, or can be a cytotoxic moiety. Cytotoxic agents are numerous and varied and include, but are not limited to, cytotoxic drugs or toxins or active fragments of such toxins. Suitable toxins and their corresponding fragments include diphtheria A chain, exotoxin A chain, ricin A chain, abrin A chain, curcin, crotin, phenomycin, enomycin, saporin, auristatin-E and the like. Cytotoxic agents also include radiochemicals made by conjugating radioisotopes to antibodies. Targeting the cytotoxic moiety to transmembrane proteins serves to increase the local concentration of the cytotoxic moiety in the targeted area.

A hypomethylating agent is a drug that inhibits DNA methylation. Because DNA methylation affects cellular function through successive generations of cells without changing the underlying DNA sequence, hypomethylating agents are considered a type of epigenetic therapy. DNA methylation is the modification of DNA nucleotides by addition of a methyl group. Currently available hypomethylating agents block the activity of DNA methyltransferase (DNA methyltransferase inhibitors/DNMT inhibitors). Members of this class include cytosine analogs, e.g. cytosine analog is one or more of 5-azacytidine, decitabine, guadecitabine, 5-Fluro-2'-deoxycytidine, etc.

For example, 5-Azacytidine, sold under the brand name Vidaza among others, is a chemical analog of cytidine, a nucleoside in DNA and RNA. 5-Azacytidine and its deoxy derivative, decitabine (also known as 5-aza-2'-deoxycytidine), are used in the treatment of myelodysplastic syndrome, acute myeloid leukemia and chronic myelomonocytic leukemia.

"Major histocompatibility complex antigens" ("MHC", also called "human leukocyte antigens", HLA) are protein molecules expressed on the surface of cells that confer a unique antigenic identity to these cells. MHC/HLA antigens are target molecules that are recognized by T-cells and natural killer (NK) cells as being derived from the same source of hematopoietic stem cells as the immune effector cells ("self") or as being derived from another source of hematopoietic reconstituting cells ("non-self"). Two main classes of HLA antigens are recognized: HLA class I and HLA class II. HLA class I antigens (A, B, and C in humans) render each cell recognizable as "self," whereas HLA class II antigens (DR, DP, and DQ in humans) are involved in reactions between lymphocytes and antigen presenting cells. Both have been implicated in the rejection of transplanted organs.

An important aspect of the HLA gene system is its polymorphism. Each gene, MHC class I (A, B and C) and MHC class II (DP, DQ and DR) exists in different alleles. HLA alleles are designated by numbers and subscripts. For example, two unrelated individuals may carry class I HLA-B, genes B5, and Bw41, respectively. Allelic gene products differ in one or more amino acids in the α and/or β domain(s). Large panels of specific antibodies or nucleic acid reagents are used to type HLA haplotypes of individuals, using leukocytes that express class I and class II molecules. The genes most important for HLA typing are the six MHC Class I and Class II proteins, two alleles for each of HLA-A; HLA-B and HLA-DR.

The HLA genes are clustered in a "super-locus" present on chromosome position 6p21, which encodes the six classical transplantation HLA genes and at least 132 protein coding genes that have important roles in the regulation of the immune system as well as some other fundamental molecular and cellular processes. The complete locus measures roughly 3.6 Mb, with at least 224 gene loci. One effect of this clustering is that "haplotypes", i.e. the set of alleles present on a single chromosome, which is inherited from one parent, tend to be inherited as a group. The set of alleles inherited from each parent forms a haplotype, in which some alleles tend to be associated together. Identifying a patient's haplotypes can help predict the probability of finding matching donors and assist in developing a search strategy, because some alleles and haplotypes are more common than others and they are distributed at different frequencies in different racial and ethnic groups.

As used herein, the term "HLA matched" refers to a donor recipient pair in which none of the HLA antigens are mismatched between the donor and recipient. HLA matched (i.e., where all of the 6 alleles are matched) donor/recipient pairs have a decreased risk of graft v. host disease (GVHD) relative to mismatched pairs (i.e. where at least one of the 6 alleles is mismatched). HLA haploidentical refers to a match where one chromosome is matched at least at HLA-A; HLA-B and HLA-DR, and may be matched at minor histocompatibility loci on the chromosome; but is not necessarily matched on the second chromosome. Such donors frequently occur in families, e.g. a parent is haploidentical to a child; and siblings may be haploidentical.

As used herein, the term "HLA mismatched" refers to a donor recipient pair in which at least one HLA antigen, in particular with respect to HLA-A, HLA-B and HLA-DR, is mismatched between the donor and recipient. In some cases, one haplotype is matched and the other is mismatched. This situation is frequently found with organs from living or deceased donors. HLA mismatched donor/recipient pairs have an increased risk of GVHD relative to perfectly matched pairs (i.e. where all 6 alleles are matched).

HLA alleles are typically noted with a variety of levels of detail. Most designations begin with HLA- and the locus name, then * and some (even) number of digits specifying the allele. The first two digits specify a group of alleles. Older typing methodologies often could not completely distinguish alleles and so stopped at this level. The third through fourth digits specify a synonymous allele. Digits five through six denote any synonymous mutations within the coding frame of the gene. The seventh and eighth digits distinguish mutations outside the coding region. Letters such as L, N, Q, or S may follow an allele's designation to specify an expression level or other non-genomic data known about it. Thus, a completely described allele may be up to 9 digits long, not including the HLA-prefix and locus notation.

As used herein, a "recipient" is an individual to whom an organ, tissue or cells from another individual (donor), commonly of the same species, has been transferred. For the purposes of the present disclosure, a recipient and a donor are either HLA-matched or HLA-mismatched.

The term stem cell is used herein to refer to a mammalian cell that has the ability both to self-renew, and to generate differentiated progeny (see Morrison et al. (1997) Cell 88:287-298). Generally, stem cells also have one or more of the following properties: an ability to undergo asynchronous, or symmetric replication, that is where the two daughter cells after division can have different phenotypes; extensive self-renewal capacity; capacity for existence in a mitotically quiescent form; and clonal regeneration of all the tissue in which they exist, for example the ability of hematopoietic stem cells to reconstitute all hematopoietic lineages.

For engraftment purposes, a composition comprising hematopoietic stem cells, is administered to a patient. Such methods are well known in the art. The stem cells are optionally, although not necessarily, purified. Abundant reports explore various methods for purification of stem cells and subsequent engraftment, including flow cytometry; an isolex system (Klein et al. (2001) Bone Marrow Transplant. 28(11):1023-9; Prince et al. (2002) Cytotherapy 4(2): 137-45); immunomagnetic separation (Prince et al. (2002) Cytotherapy 4(2):147-55; Handgretinger et al. (2002) Bone Marrow Transplant. 29(9):731-6; Chou et al. (2005) Breast Cancer. 12(3):178-88); and the like. Each of these references is herein specifically incorporated by reference, particularly with respect to procedures, cell compositions and doses for hematopoietic stem cell transplantation.

Hematopoietic stem cells can be obtained by harvesting from bone marrow or from peripheral blood. Bone marrow is generally aspirated from the posterior iliac crests while the donor is under either regional or general anesthesia. Additional bone marrow can be obtained from the anterior iliac crest. A dose of $1 \times 10^8$ and $2 \times 10^8$ marrow mononuclear cells per kilogram is generally considered desirable to establish engraftment in autologous and allogeneic marrow transplants, respectively. Bone marrow can be primed with granulocyte colony-stimulating factor (G-CSF; filgrastim [Neupogen]) to increase the stem cell count. Reference to "whole bone marrow" for the purposes described herein generally refers to a composition of mononuclear cells derived from bone marrow that have not been selected for specific immune cell subsets. "Fractionated bone marrow" may be, for example, depleted of T cells, e.g. CD8+ cells, CD52+ cells, CD3+ cells, etc.; enriched for CD34+ cells, etc.

Hematopoietic stem cells are also obtained from cord blood. Cord blood is an almost unlimited source of hematopoietic stem cells for allogeneic hematopoietic stem cell transplant. Cord blood banks (CBB) have been established for related or unrelated UCBT with more than 400,000 units available and more than 20,000 umbilical cord blood transplants performed in children and in adults. UCB hematopoietic progenitors are enriched in primitive stem/progenitor cells able to produce in vivo long-term repopulating stem cells. However, the number of cells available from any single donor can be relatively low in comparison with other sources.

Mobilization of stem cells from the bone marrow into peripheral blood by cytokines such as G-CSF or GM-CSF has led to the widespread adoption of peripheral blood progenitor cell collection by apheresis for hematopoietic stem cell transplantation. The dose of G-CSF used for mobilization is 10 µg/kg/day. In autologous donors who are heavily pretreated, however, doses of up to 40 µg/kg/day can be given. Mozobil may be used in conjunction with G-CSF to mobilize hematopoietic stem cells to peripheral blood for collection.

The dose of stem cells administered may depend on the desired purity of the infused cell composition, and the source of the cells. Current guidelines indicate that the minimum dose required for engraftment is $1\text{-}2\times10^6$ CD34+ cells/kg body weight for autologous and allogeneic transplants. Higher doses can include, for example, $3\times10^6$, $4\times10^6$, $5\times10^6$, $6\times10^6$, $7\times10^6$, $8\times10^6$, $9\times10^6$, $10^7$ or more. Frequently the dose is limited by the number of available cells. Typically, regardless of the source, the dose is calculated by the number of CD34+ cells present. The percent number of CD34+ cells can be low for unfractionated bone marrow or mobilized peripheral blood; in which case the total number of cells administered is much higher.

The CD34+ cells may be selected by affinity methods, including without limitation magnetic bead selection, flow cytometry, and the like from the donor hematopoietic cell sample. The HSPC composition may be at least about 50% pure, as defined by the percentage of cells that are CD34+ in the population, may be at least about 75% pure, at least about 85% pure, at least about 95% pure, or more. Preferable a maximum number of CD3+ cells delivered with the HSPC composition is not more than about $10^6$ CD3+ cells/kg of recipient body weight, not more than about $10^5$ CD3+ cells/kg of recipient body weight, not more than about $10^4$ CD3+ cells/kg of recipient body weight. Alternatively cell populations may be tandemly selected for expression of CD34 and CD90, which cell populations may be highly purified, e.g. at least about 85% CD34+CD90+ cells, at least about 90% CD34+CD90+ cells, at least about 95% CD34+ CD90+ cells and may be up to about 99% CD34+CD90+ cells or more. Alternatively, unmanipulated bone marrow or mobilized peripheral blood populations are used.

Hematopoietic stem cells can also be generated in vitro, for example from pluripotent embryonic stem cells, induced pluripotent cells, and the like. For example, see Sugimura et al. (2017) Nature 545:432-438, herein specifically incorporated by reference, which details a protocol for generation of hematopoietic progenitors.

The cells which are employed may be fresh, frozen, or have been subject to prior culture. They may be fetal, neonate, adult, etc. Hematopoietic stem cells may be obtained from fetal liver, bone marrow, blood, particularly G-CSF or GM-CSF mobilized peripheral blood, or any other conventional source. Cells for engraftment are optionally isolated from other cells, where the manner in which the stem cells are separated from other cells of the hematopoietic or other lineage is not critical to this invention. If desired, a substantially homogeneous population of stem or progenitor cells may be obtained by selective isolation of cells free of markers associated with differentiated cells, while displaying epitopic characteristics associated with the stem cells.

Cells may be genetically altered in order to introduce genes useful in the differentiated cell, e.g. repair of a genetic defect in an individual, selectable marker, etc., or genes useful in selection against undifferentiated ES cells. For example, programmable gene editing tools such as CRISPR/cas9 and the like can be used to edit genomes. Cells may also be genetically modified to correct genetic defects, enhance survival, control proliferation, competitiveness, and the like. Cells may be genetically altering by transfection or transduction with a suitable vector, homologous recombination, or other appropriate technique, so that they express a gene of interest. In one embodiment, cells are transfected with genes encoding a telomerase catalytic component (TERT), typically under a heterologous promoter that increases telomerase expression beyond what occurs under the endogenous promoter, (see International Patent Application WO 98/14592). In other embodiments, a selectable marker is introduced, to provide for greater purity of the desired differentiating cell. Cells may be genetically altered using vector containing supernatants over an 8-16 h period, and then exchanged into growth medium for 1-2 days. Genetically altered cells are selected using a drug selection agent such as puromycin, G418, or blasticidin, and then recultured.

The cells of this invention can also be genetically altered in order to enhance their ability to be involved in tissue regeneration, or to deliver a therapeutic gene to a site of administration. A vector is designed using the known encoding sequence for the desired gene, operatively linked to a promoter that is constitutive, pan-specific, specifically active in a differentiated cell type, etc. Suitable inducible promoters are activated in a desired target cell type, either the transfected cell, or progeny thereof. By transcriptional activation, it is intended that transcription will be increased above basal levels in the target cell by at least about 100-fold, more usually by at least about 1000 fold. Various promoters are known that are induced in different cell types.

In some cases, a cell is modified by a class 2 CRISPR/Cas effector protein (or a nucleic encoding the protein), e.g., as an endonuclease. In class 2 CRISPR systems, the functions of the effector complex (e.g., the cleavage of target DNA) are carried out by a single protein (which can be referred to as a CRISPR/Cas effector protein)—where the natural protein is an endonuclease (e.g., see Zetsche et al, Cell. 2015 Oct. 22; 163(3):759-71; Makarova et al, Nat Rev Microbiol. 2015 November; 13(11):722-36; Shmakov et al., Mol Cell. 2015 Nov. 5; 60(3):385-97; and Shmakov et al., Nat Rev Microbiol. 2017 March; 15(3):169-182: "Diversity and evolution of class 2 CRISPR-Cas systems"). As such, the term "class 2 CRISPR/Cas protein" or "CRISPR/Cas effector protein" is used herein to encompass the effector protein from class 2 CRISPR systems—for example, type II CRISPR/Cas proteins (e.g., Cas9), type V CRISPR/Cas proteins (e.g., Cpf1/Cas12a, C2c1/Cas12b, C2C3/Cas12c), and type VI CRISPR/Cas proteins (e.g., C2c2/Cas13a, C2C7/Cas13c, C2c6/Cas13b). Class 2 CRISPR/Cas effector proteins include type II, type V, and type VI CRISPR/Cas proteins, but the term is also meant to encompass any class 2 CRISPR/Cas protein suitable for binding to a corresponding guide RNA and forming a ribonucleoprotein (RNP) complex.

In some cases, an RNA-guided endonuclease is a fusion protein that is fused to a heterologous polypeptide (also referred to as a "fusion partner"). In some cases, an RNA-guided endonuclease is fused to an amino acid sequence (a fusion partner) that provides for subcellular localization, i.e., the fusion partner is a subcellular localization sequence (e.g., one or more nuclear localization signals (NLSs) for targeting to the nucleus, two or more NLSs, three or more NLSs, etc.). In some embodiments, an RNA-guided endonuclease is fused to an amino acid sequence (a fusion partner) that provides a tag (i.e., the fusion partner is a detectable label) for ease of tracking and/or purification (e.g., a fluorescent protein, e.g., green fluorescent protein (GFP), YFP, RFP, CFP, mCherry, tdTomato, and the like; a histidine tag, e.g., a 6×His tag; a hemagglutinin (HA) tag; a FLAG tag; a Myc tag; and the like). In some cases, the fusion partner can provide for increased or decreased stability (i.e., the fusion partner can be a stability control peptide, e.g., a degron, which in some cases is controllable (e.g., a temperature sensitive or drug controllable degron sequence).

An RNA-guided endonuclease (e.g., a Cas9 protein) can have multiple (1 or more, 2 or more, 3 or more, etc.) fusion partners in any combination of the above. As an illustrative example, an RNA-guided endonuclease (e.g., a Cas9 protein) can have a fusion partner that provides for tagging (e.g., GFP), and can also have a subcellular localization sequence (e.g., one or more NLSs). In some cases, such a fusion protein might also have a tag for ease of tracking and/or purification (e.g., a histidine tag, e.g., a 6×His tag; a hemagglutinin (HA) tag; a FLAG tag; a Myc tag; and the like). As another illustrative example, an RNA-guided endonuclease (e.g., a Cas9 protein) can have one or more NLSs (e.g., two or more, three or more, four or more, five or more, 1, 2, 3, 4, or 5 NLSs). In some cases a fusion partner (or multiple fusion partners, e.g., 1, 2, 3, 4, or 5 NLSs) (e.g., an NLS, a tag, a fusion partner providing an activity, etc.) is located at or near the C-terminus of the RNA-guided endonuclease (e.g., Cas9 protein). In some cases a fusion partner (or multiple fusion partners, e.g., 1, 2, 3, 4, or 5 NLSs) (e.g., an NLS, a tag, a fusion partner providing an activity, etc.) is located at the N-terminus of the RNA-guided endonuclease (e.g., Cas9 protein). In some cases the genome editing nuclease (e.g., Cas9 protein) has a fusion partner (or multiple fusion partners, e.g., 1, 2, 3, 4, or 5 NLSs)(e.g., an NLS, a tag, a fusion partner providing an activity, etc.) at both the N-terminus and C-terminus.

Other vectors useful for transferring exogenous genes into target mammalian cells are available. The vectors may be episomal, e.g. plasmids, virus derived vectors such cytomegalovirus, adenovirus, etc., or may be integrated into the target cell genome, through homologous recombination or random integration, e.g. retrovirus derived vectors such MMLV, HIV-1, ALV, etc. For modification of stem cells, lentiviral vectors are preferred. Lentiviral vectors such as those based on HIV or FIV gag sequences can be used to transfect non-dividing cells, such as the resting phase of human stem cells. Combinations of retroviruses and an appropriate packaging line may also find use, where the capsid proteins will be functional for infecting the target cells. Usually, the cells and virus will be incubated for at least about 24 hours in the culture medium. The cells are then allowed to grow in the culture medium for short intervals in some applications, e.g. 24-73 hours, or for at least two weeks, and may be allowed to grow for five weeks or more, before analysis. Commonly used retroviral vectors are "defective", i.e. unable to produce viral proteins required for productive infection. Replication of the vector requires growth in the packaging cell line. The vectors may include genes that must later be removed, e.g. using a recombinase system such as Cre/Lox, or the cells that express them destroyed, e.g. by including genes that allow selective toxicity such as herpesvirus TK, bcl-xs, etc.

Chimerism, as used herein, generally refers to chimerism of the hematopoietic system, unless otherwise noted. A determination of whether an individual is a full chimera, mixed chimera, or non-chimeric made be made by an analysis of a hematopoietic cell sample from the graft recipient, e.g. peripheral blood, bone marrow, etc. as known in the art, for example at 3 months post-transplant, 6 months post-transplant, 12 months post-transplant, etc. Analysis may be done by any convenient method of typing. In some embodiments the degree of chimerism amongst all mononuclear cells, T cells, B cells, CD56+NK cells, and CD15+ neutrophils is regularly monitored, using PCR with probes for microsatellite analysis. For example, commercial kits that distinguish polymorphisms in short terminal repeat lengths of donor and host origin are available. Automated readers provide the percentage of donor type cells based on standard curves from artificial donor and host cell mixtures.

Individuals who exhibited more than a 95% donor cells in a given blood cell lineage by such analysis at any time post-transplantation are referred to as having full donor chimerism in this transplant patient group. Mixed chimerism is defined as greater than 1% donor but less than 95% donor DNA in such analysis. Individuals who exhibit mixed chimerism may be further classified according to the evolution of chimerism, where improving mixed chimerism is defined as a continuous increase in the proportion of donor cells over at least a 6-month period. Stable mixed chimerism is defined as fluctuations in the percentage of recipient cells over time, without complete loss of donor cells.

A "patient" for the purposes of the present invention includes both humans and other animals, particularly mammals, including pet and laboratory animals, e.g. mice, rats, rabbits, etc. Thus, the methods are applicable to both human therapy and veterinary applications. In one embodiment the patient is a mammal, preferably a primate. In other embodiments the patient is human.

The terms "treatment", "treating", "treat" and the like are used herein to generally refer to obtaining a desired pharmacologic and/or physiologic effect. The effect can be prophylactic in terms of completely or partially preventing a disease or symptom(s) thereof and/or may be therapeutic in terms of a partial or complete stabilization or cure for a disease and/or adverse effect attributable to the disease. The term "treatment" encompasses any treatment of a disease in a mammal, particularly a human, and includes: (a) preventing the disease and/or symptom(s) from occurring in a subject who may be predisposed to the disease or symptom but has not yet been diagnosed as having it; (b) inhibiting the disease and/or symptom(s), i.e., arresting their development; or (c) relieving the disease symptom(s), i.e., causing regression of the disease and/or symptom(s). Those in need of treatment include those already inflicted (e.g., those with cancer, those with an infection, etc.) as well as those in which prevention is desired (e.g., those with increased susceptibility to cancer, those with an increased likelihood of infection, those suspected of having cancer, those suspected of harboring an infection, etc.).

Conditioning with Anti-CD117 Antibody and AZA for HSC Engraftment

The methods of the invention provide for improved engraftment of stem cells after transplantation into a recipient. The recipient may be immunocompetent, and the transplantation may be performed in the absence of myeloablative conditioning. The recipient is conditioned with the administration of an effective dose of an agent specific for CD117 in combination with a hypomethylating agent, e.g. an antibody.

An effective dose of anti-CD117 agent is the dose that depletes endogenous hematopoietic stem cells. The effective dose will depend on the individual and the specific agent, but will generally be up to about 100 µg/kg body weight, up to about 250 µg/kg, up to about 500 µg/kg, up to about 750 µg/kg, up to about 1 mg/kg, up to about 1.2 mg/kg, up to about 1.5 mg/kg, up to about 3 mg/kg, up to about 5 mg/kg, up to about 10 mg/kg.

The anti-CD117 agent is provided in the absence of myeloablative radiation, may be administered in a single dose, or may be administered twice or more for a period of time sufficient to effect the desired depletion of endogenous stem cells. They may also be administered in combination with other non-myeloablative regimens such as total lymphoid irradiation (TLI) or low dose total body irradiation (TBI). The agent specific for CD117 is administered in combination with hypomethylating agents that modify or deplete HSC. In some embodiments the hypomethylating agent/anti-CD117 agent combination includes other agents, e.g. biologics including without limitation anti-CD47, anti-CD38, etc., or other chemotherapeutic agents, e.g. venetoclax, etc.

The infusion of either bone marrow or peripheral blood stem and progenitor cell products is a relatively simple process that is performed at the bedside. The stem cell containing product is generally used fresh and is infused through a central vein over a period of several hours. Autologous or allogeneic products may be cryopreserved; if so they are thawed and infused over a specified time period.

Where the donor is allogeneic to the recipient, the HLA type of the donor and recipient may be tested for a match, or haploidentical cells are used. HLA-haploidentical donors can be manipulated by CD34 or CD34CD90 selection. Moreover, HLA-haplo-identical donors are now widely used (and may surpass HLA-identical) for other indications. This widespread use is made possible by the administration of cyclophosphamide in the days post-transplant to prevent GVHD. For HLA matching, traditionally, the loci critical for matching are HLA-A, HLA-B, and HLA-DR. HLA-C and HLA-DQ are also now considered when determining the appropriateness of a donor. A completely matched sibling donor is generally considered the ideal donor. For unrelated donors, a complete match or a single mismatch is considered acceptable for most transplantation, although in certain circumstances, a greater mismatch is tolerated. Preferably matching is both serologic and molecular. Where the donor is umbilical cord blood the degree of tolerable HLA disparity is much greater, and a match of 3-4 out of the 6 HLA-A, HLA-B and HLA-DRB1 antigens is sufficient for transplantation. Immunocompetent donor T cells may be removed using a variety of methods to reduce or eliminate the possibility that graft versus host disease (GVHD) will develop.

For positive selection of CD34$^+$ cells, commercial instruments can be employed to remove the desired cells, using solid-phase, anti-CD34 monoclonal antibodies. With negative selection, anticancer monoclonal antibodies can be used to remove tumor cells, leaving stem cells in the graft.

Engraftment of HSC

Following infusion of the conditioning regimen, i.e. anti-CD117 agent in combination with a hypomethylating agent, a population of donor HSC are administered. Administration (transplantation) of the donor HSC may be delayed until the Cmax of an anti-CD117 agent, e.g. a depleting antibody, in serum has dropped to a level below about 500 ng/ml, below 100 ng/ml; and may be below about 10 ng/ml; below about 5 ng/ml. The period of time for the drop in antibody titer can be variable depending on the patient; and analysis of antibody levels may be desirable.

Donor cell populations for transplantation are enriched for CD34+ hematopoietic stem cells. In some embodiments the donor cells are HLA-matched. In some embodiments the donor cells are haplotype matched. In some embodiments the donor cells are autologous, including without limitation genetically corrected autologous cells. In some embodiments the donor cells are mobilized peripheral blood cells; in other embodiments the donor cells are bone marrow cells. In some embodiments the donor cells are enriched for expression of CD34, e.g. by art recognized methods such as the cliniMACS® system, by flow cytometry, etc. Cell populations single enriched for CD34 may be from about 50% up to about 90% CD34$^+$ cells. Alternatively cell populations may be tandemly selected for expression of CD34 and CD90, which cell populations may be highly purified, e.g. at least about 85% CD34$^+$CD90$^+$ cells, at least about 90% CD34$^+$CD90$^+$ cells, at least about 95% CD34$^+$CD90$^+$ cells and may be up to about 99% CD34$^+$CD90$^+$ cells or more. Alternatively unmanipulated bone marrow or mobilized peripheral blood populations are used.

The dose of cells is at least about $2\times10^6$ CD34$^+$ cells/kg from a single enriched population, preferably at least about $10\times10^6$ CD34$^+$ cells/kg. Higher doses, if available, are generally not deleterious, with the proviso that not more than about $3\times10^4$ CD3$^+$ cells/kg are administered. For a tandemly selected population, where a high percentage of the CD34$^+$ cells are HSC, the dose may be lower, e.g. at least about $3\times10^5$ CD34$^+$ cells/kg, at least about $5\times10^5$ CD34$^+$ cells/kg, at least about $10^6$ CD34$^+$ cells/kg. Higher doses can be administered with the proviso that not more than about $3\times10^3$ CD3$^+$ cells/kg are administered.

In some embodiments, success of the procedure is monitored by determining the presence of host-derived myeloid cells, including without limitation, CD15$^+$ cells, in circulation of the recipient. Blood myeloid chimerism is indicator of true HSC engraftment due to the short-lived nature of myeloid cells. After about 8 weeks post-HCT, methods described herein have provided for measurable and sustained levels of blood myeloid chimerism, e.g. of at least about 1% donor type CD15$^+$ cells, at least about 2% donor type CD15$^+$ cells, at least about 4% donor type CD15$^+$ cells, at least about 8% donor type CD15$^+$ cells, or more. In some embodiments, long term HSC engraftment is evidenced by myeloid chimerism $\geq$5% at 24 weeks, reconstitution of T and B lymphoid compartments with reduced or eliminated dependence on immunoglobulin supplementation. Sustained chimerism may be achieved for greater than one year post-transplantation.

Formulations

For depletion, each of the anti-CD117 agent, e.g. anti-CD117 antibody, and hypomethylating agent is formulated in a pharmaceutical composition. The anti-CD117 agent, e.g. anti-CD117 antibody, and the hypomethylating agents can be formulated separately or together, usually separately. The exact dose will depend on the purpose of the treatment, and will be ascertainable by one skilled in the art using known techniques (e.g., Ansel et al., Pharmaceutical Dosage Forms and Drug Delivery; Lieberman, Pharmaceutical Dosage Forms (vols. 1-3, 1992), Dekker, ISBN 0824770846, 082476918X, 0824712692, 0824716981; Lloyd, The Art, Science and Technology of Pharmaceutical Compounding (1999); and Pickar, Dosage Calculations (1999)). As is known in the art, adjustments for patient condition, systemic versus localized delivery, as well as the age, body weight, general health, sex, diet, time of administration, drug interaction and the severity of the condition may be necessary, and will be ascertainable with routine experimentation by those skilled in the art.

The administration of the agents can be done in a variety of ways as discussed above, including, but not limited to, orally, subcutaneously, intravenously, intranasally, transdermally, intraperitoneally, intramuscularly, intrapulmonary, vaginally, rectally, or intraocularly.

In one embodiment, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly useful are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol.

The pharmaceutical compositions can be administered in a variety of unit dosage forms depending upon the method of administration. For example, unit dosage forms suitable for oral administration include, but are not limited to, powder, tablets, pills, capsules and lozenges. It is recognized that compositions of the invention when administered orally, should be protected from digestion. This is typically accomplished either by complexing the molecules with a composition to render them resistant to acidic and enzymatic hydrolysis, or by packaging the molecules in an appropriately resistant carrier, such as a liposome or a protection barrier. Means of protecting agents from digestion are well known in the art.

The compositions for administration will commonly comprise an antibody or other ablative agent dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, e.g., sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs (e.g., Remington's Pharmaceutical Science (15th ed., 1980) and Goodman & Gillman, The Pharmacological Basis of Therapeutics (Hardman et al., eds., 1996)).

Compositions are administered to a patient in an amount sufficient to substantially deplete targeted endogenous stem cells, as described above. An amount adequate to accomplish this is defined as a "therapeutically effective dose." Single or multiple administrations of the compositions may be administered depending on the dosage and frequency as required and tolerated by the patient. The particular dose required for a treatment will depend upon the medical condition and history of the mammal, as well as other factors such as age, weight, gender, administration route, efficiency, etc.

In the methods of the invention, the agents are administered as a short course of therapy prior to transplantation.

Conditions for Treatment

The indications for stem cell transplantation vary according to disease categories and are influenced by factors such as cytogenetic abnormalities, response to prior therapy, patient age and performance status, disease status (remission vs relapse), disease-specific prognostic factors, availability of a suitable graft source, time of referral, and time to transplant.

Myelodysplastic syndrome (MDS). The myelodysplastic syndromes (MDS) are classified according to features of cellular morphology, etiology, clinical presentation, and cytogenetic and molecular features. The morphological classification of the MDS is largely based on the percent of myeloblasts in the bone marrow and blood, the type and degree of myeloid dysplasia, and the presence of ringed sideroblasts. The clinical classification of the MDS depends upon whether there is an identifiable etiology, the nature of the molecular or chromosomal abnormalities and whether the MDS has been treated previously. Current classification of MDS cellular types and subtypes are listed below.

Included in MDS is Refractory anemia (RA). In patients with RA, the myeloid and megakaryocytic series in the bone marrow appear normal to conventional tests, but megaloblastoid erythroid hyperplasia is present. Dysplasia is usually minimal. Marrow blasts are less than 5%, and no peripheral blasts are present. Macrocytic anemia with reticulocytopenia is present in the blood. Transformation to acute leukemia is rare, and median survival varies from 2 years to 5 years in most series.

Refractory anemia with ringed sideroblasts (RARS). In patients with RARS, the blood and marrow are identical to those in patients with RA, except that at least 15% of marrow red cell precursors are ringed sideroblasts. Prognosis is similar to that of RA.

Refractory anemia with excess blasts (RAEB). In patients with RAEB, there is significant evidence of disordered myelopoiesis and megakaryocytopoiesis in addition to abnormal erythropoiesis. Because of differences in prognosis related to progression to a frank AML, this cellular classification is comprised of two categories, refractory anemia with excess blasts-1 (RAEB-1) and refractory anemia with excess blasts-2 (RAEB-2). Combined, the two categories account for approximately 40% of all patients with MDS. RAEB-1 is characterized by 5% to 9% blasts in the bone marrow and less than 5% blasts in the blood. Approximately 25% of cases of RAEB-1 progress to AML. Median survival is approximately 18 months. RAEB-2 is characterized by 10% to 19% blasts in the bone marrow. Approximately 33% of cases of RAEB-2 progress to AML. Median survival for RAEB-2 is approximately 10 months.

Refractory cytopenia with multilineage dysplasia (RCMD). In patients with RCMD, bicytopenia or pancytopenia is present. In addition, dysplastic changes are present in 10% or more of the cells in two or more myeloid cell lines. There are less than 1% blasts in the blood and less than 5% blasts in the bone marrow. Auer rods are not present. Monocytes in the blood are less than $1\times10^9$. RCMD accounts for approximately 24% of cases of MDS. The frequency of evolution to acute leukemia is 11%. The overall median survival is 33 months. Refractory cytopenia with multilineage dysplasia and ringed sideroblasts (RCMD-RS) represents another category of RMDS. In RCMD-RS, features of RCMD are present, and more than 15% of erythroid precursors in the bone marrow are ringed sideroblasts. RCMD-RS accounts for approximately 15% of cases of MDS. Survival in RCMD-RS is similar to that in primary RCMD.

Myelodysplastic syndrome associated with an isolated del(5q) chromosome abnormality is associated with an isolated del(5q) cytogenetic abnormality. Blasts in both blood and bone marrow are less than 5%. This subtype is associated with a long survival.

The mainstay of treatment of the myelodysplastic syndromes (MDS) has conventionally been supportive care. The use of erythropoietin may improve anemia, although effective treatment may require substantially higher doses of erythropoietin than are used for other indications (150-300 μg/kg/day).

Acute myelogenous leukemia (AML). Acute myelogenous leukemia involves malignant transformation and uncontrolled proliferation of an abnormally differentiated, long-lived progenitor cell that results in high circulating numbers of immature blood forms and replacement of normal marrow by malignant cells. Symptoms include fatigue, pallor, easy bruising and bleeding, fever, and infection; symptoms of extramedullary leukemic infiltration are present in only about 5% of patients. There are a number of subtypes.

A subtype of particular interest is secondary acute myeloid leukemia, referring to the development of AML after myelodysplastic syndromes (MDS) or myeloproliferative neoplasms (MPN). Secondary AML is associated to factors that confer a poor prognosis such as high age and high-risk chromosomal and molecular abnormalities.

Autologous HSCT is currently used to treat the following conditions: Multiple myeloma, Non-Hodgkin lymphoma, Hodgkin disease, Acute myeloid leukemia, Neuroblastoma, Germ cell tumors, Autoimmune disorders—Systemic lupus erythematosus (SLE), systemic sclerosis, Amyloidosis.

Allogenic HSCT is currently used to treat the following disorders: Acute myeloid leukemia, Acute lymphoblastic leukemia, Chronic myeloid leukemia; Chronic lymphocytic leukemia, Myeloproliferative disorders, Myelodysplastic syndromes, Multiple myeloma, Non-Hodgkin lymphoma, Hodgkin disease, Aplastic anemia, Pure red cell aplasia, Paroxysmal nocturnal hemoglobinuria, Fanconi anemia, Thalassemia major, Sickle cell anemia, Severe combined immunodeficiency (SCID), Wiskott-Aldrich syndrome, Hemophagocytic lymphohistiocytosis (HLH), Inborn errors of metabolism—Eg, mucopolysaccharidosis, Gaucher disease, metachromatic leukodystrophies, and adrenoleukodystrophies, Epidermolysis bullosa, Severe congenital neutropenia, Shwachman-Diamond syndrome, Diamond-Blackfan anemia, Leukocyte adhesion deficiency, and the like.

Embodiments of the invention include transplantation into a patient suffering from a genetic blood disorder, where exogenous stem cells of a normal phenotype are transplanted into the patient. Such diseases include, without limitation, the treatment of anemias caused by defective hemoglobin synthesis (hemoglobinopathies). The stem cells may be allogeneic stem cells of a normal phenotype, or may be autologous cells that have been genetically engineered to delete undesirable genetic sequences, and/or to introduce genetic sequences that correct the genetic defect.

Sickle cell diseases include HbS Disease; drepanocytic anemia; meniscocytosis. Chronic hemolytic anemia occurring almost exclusively in blacks and characterized by sickle-shaped RBCs caused by homozygous inheritance of Hb S. Homozygotes have sickle cell anemia; heterozygotes are not anemic, but the sickling trait (sicklemia) can be demonstrated in vitro. In Hb S, valine is substituted for glutamic acid in the sixth amino acid of the beta chain. Deoxy-Hb S is much less soluble than deoxy-Hb A; it forms a semisolid gel of rodlike tactoids that cause RBCs to sickle at sites of low $PO_2$. Distorted, inflexible RBCs adhere to vascular endothelium and plug small arterioles and capillaries, which leads to occlusion and infarction. Because sickled RBCs are too fragile to withstand the mechanical trauma of circulation, hemolysis occurs after they enter the circulation. In homozygotes, clinical manifestations are caused by anemia and vaso-occlusive events resulting in tissue ischemia and infarction. Growth and development are impaired, and susceptibility to infection increases. Anemia is usually severe but varies highly among patients. Anemia may be exacerbated in children by acute sequestration of sickled cells in the spleen.

Thalassemias are a group of chronic, inherited, microcytic anemias characterized by defective Hb synthesis and ineffective erythropoiesis, particularly common in persons of Mediterranean, African, and Southeast Asian ancestry. Thalassemia is among the most common inherited hemolytic disorders. It results from unbalanced Hb synthesis caused by decreased production of at least one globin polypeptide chain (β, α, γ, δ).

Aplastic anemia results from a loss of RBC precursors, either from a defect in stem cell pool or an injury to the microenvironment that supports the marrow, and often with borderline high MCV values. The term aplastic anemia commonly implies a panhypoplasia of the marrow with associated leukopenia and thrombocytopenia.

Combined immunodeficiency is a group of disorders characterized by congenital and usually hereditary deficiency of both B- and T-cell systems, lymphoid aplasia, and thymic dysplasia. The combined immunodeficiencies include severe combined immunodeficiency, Swiss agammaglobulinemia, combined immunodeficiency with adenosine deaminase or nucleoside phosphorylase deficiency, and combined immunodeficiency with immunoglobulins (Nezelof syndrome). Most patients have an early onset of infection with thrush, pneumonia, and diarrhea. If left untreated, most die before age 2. Most patients have profound deficiency of B cells and immunoglobulin. The following are characteristic: lymphopenia, low or absent T-cell levels, poor proliferative response to mitogens, cutaneous anergy, an absent thymic shadow, and diminished lymphoid tissue. *Pneumocystis* pneumonia and other opportunistic infections are common.

EXPERIMENTAL

Example 1

Monoclonal antibody (mAb)-targeting of CD117 (c-Kit) on the surface of hematopoietic stem cells (HSC) is an emerging strategy to safely condition patients for hematopoietic cell transplantation (HCT). These mAbs aim to eliminate recipient HSC from bone marrow niches to permit donor HSC engraftment. To date, such HSC niche clearance has been accomplished by standard-of-care genotoxic alkylators or radiation, which cause substantial morbidity and mortality. We have sought to develop the anti-CD117 platform to replace or augment standard conditioning and thereby reduce the acute and long-term toxicities of HCT. Here, we show that the anti-mouse CD117-mAb, ACK2, combined with the clinically well-established hypomethylating agent, 5-Azacytidine (AZA), permits stable multilineage donor chimerism after HSC transplantation in immunocompetent mice. Notably, we determined that single agent AZA transiently depletes endogenous HSC and enables low levels of donor engraftment. Moreover, the addition of ACK2 led to more robust HSC depletion and higher levels of donor chimerism in mouse models of congenic and allogeneic HCT. The effectiveness of the combination on HSC depletion was dependent on the antagonistic potency of the anti-CD117 mAb, and exposure to exogenous stem cell factor (SCF) in vivo rescued long-term HSC, indicating that blocking the SCF/CD117 interaction by anti-CD117 mAb is essential for achieving the desired potency of the dual combination. Together, these findings highlight a novel conditioning strategy by using anti-CD117 mAb and AZA, which may be rapidly translated into the clinical setting.

Based on the favorable safety profile and unique mechanism of action of anti-CD117 mAbs relative to other conditioning modalities, we have further tested this approach in combination with agents already in clinical use with the goal to potentiate HSC elimination and develop rapidly translatable novel conditioning regimens. Here we show that 5-Azacytidine (AZA) synergizes with ACK2 to deplete HSC and enable congenic and allogeneic donor HSC engraftment in wildtype mice. AZA is a nucleoside analogue best known as an epigenetic modifier used for the treatment of MDS, AML, and chronic myelomonocytic leukemia (CMML). The anti-tumor activity of AZA has been related to multiple mechanisms beyond re-expression of silenced tumor suppressor genes, such as direct apoptotic effects on malignant cells, promoting immune-mediated response against tumor cells, differentiation induction, and effects on the bone marrow microenvironment. Although myelosuppression is the most common hematologic adverse event, little is known about the effects of AZA on normal hematopoiesis in vivo.

Administration of AZA as maintenance therapy in patients after HCT, who have reconstituted normal hematopoiesis, results in neutropenia and thrombocytopenia, which suggests that AZA-induced myelosuppression cannot be fully explained by the anti-leukemic effects of the drug.

By studying the effects of AZA on normal hematopoiesis in immunocompetent mice, we show, for the first time, that AZA induces rapid depletion of CD117$^+$ cells in the bone marrow, including long-term (LT) and short-term (ST) HSC. Depletion was promptly followed by significant expansion of the downstream myeloid biased multipotent progenitors (MPP2; Lin−Sca+Kit+CD150+CD48+) with rapid recovery of mature myeloid cells. Treatment with AZA resulted in HSC depletion of sufficient magnitude to enable engraftment of donor HSC in immunocompetent mice. Moreover, blockade of CD117 by ACK2 followed by administration of AZA resulted in synergist depletion of recipient HSC, prolonged HSC recovery, and significant increase in the levels of donor HSC engraftment in immunocompetent mice.

Materials and Methods

Mice. C57BL/6 (B6) mice (H-2$^b$, Thy1.1, CD45.1/CD45.2) were recipients and B6 mice (H-2$^b$, Thy1.1, CD45.1) were donors for the congenic transplant experiments. BALB.B (H-2$^b$, Thy1.2, CD45.2) mice were used as recipients and B6 mice (H-2$^b$, Thy1.1, CD45.1) as donors for minor MHC-matched (allogeneic) transplant experiments. Recipients were >8 weeks old and donors were 8-12 weeks old at timepoint of transplantation. B6 (H-2$^b$, Thy1.1, CD45.2) mice were used for in vivo depletion studies. Mice were bred and maintained under pathogen free conditions at the Stanford University Research Animal Facility. All experiments were performed under a protocol approved by the Stanford Administrative Panel on Laboratory Animal Care.

In vivo administration of therapeutic agents and cytokines. Anti-mouse CD117 mAbs, clone ACK2 (BioXcell) and 2B8 (BioXcell), were injected retroorbital as a single dose of 500 μg following intraperitoneal administration of Diphenhydramine (Benadryl). Anti CD4 (clone GK1.5, BioXcell) and anti-CD8 (clone YTS169.4, BioXcell) were administered intraperitoneally at a dose of 100 μg in 100 μl phosphate-buffered saline (PBS). 5-Azacytidine (AZA) (STEMCELL Technologies), was reconstituted in PBS to a concentration of 5 mg/ml and kept at −20° for up to 1 month. Before each injection, AZA was thawed for 10-15 min at room temperature (RT), resuspended in PBS and administered intraperitoneally in 100 μl. Recombinant murine SCF (PeproTech), dissolved in deionized water to concentration of 10 μg/ml, was injected intraperitoneally at the amount of 1 μg/day.

Flow cytometry. Cells were stained for surface markers and incubated at RT in the dark for 20 min. Monoclonal antibodies used for mouse depletion/sorting studies: CD3 Pe-Cy5 (clone 145-2c11), CD3 APC (clone 145-2c11), CD4 Pe-Cy5 (clone GK1.5), CD4 PerCyP-Cy5.5 (clone RM4.5), CD8 Pe-Cy5 (clone 53-6.7), CD8 APC-Cy7 (5H10), CD19 Pe-Cy7 (clone 1D3), Mac-1 Pe-Cy5 (clone M1/70), Mac-1 Alexa Fluor (clone M1/70), Gr-1 Pe-Cy5 (clone R66-8C5), Gr-1 PB (clone RB6-8C5), NK1.1 PE (clone PK136), c-Kit APC-Cy-7 (clone 2B8), Sca1 Pe-Cy7 (clone D7), CD48

APC (clone HM48-1), CD150 PB (clone TC15-12 F 12.2), CD16/32 PE (clone 93), CD34 FITC (clone RAM34), CD127 PB (clone A7R34), Flt3 PE (clone A2F10).

For the Ki67 analyses cells were first stained with antibodies that mark the different HSPC subsets. Stained cells were washed with PBS, fixed with Cytofix/Cytoperm buffer (BD Biosciences) for 1 h at 4° C. and washed twice with 1× PermWash buffer (BD Biosciences). Cells were then stained with Ki67 FITC antibody (clone B56, BD Biosciences) or isotype control, incubated for 1 h at RT and washed twice with 1× PermWash buffer. Monoclonal antibodies used for chimerism analyses: CD45.1 FITC (clone A20), CD45.2 PB (clone 104), CD3 APC-Cy7 (clone 145-2c11), CD19 APC (clone 1 D3), Gr-1 PE (clone R66-8C5), Mac-1 Pe-Cy7 (clone M1/70), Ter-119 Pe-Cy5 (clone TER-119), NK1.1 Alexa Fluor (clone PK136).

Monoclonal antibodies used for in vitro human HSC-sorting experiments: CD2, CD3, CD4, CD7, CD8, CD10, CD11 b, CD14, CD19, CD20, CD56, CD235a (all in Pe-Cy7), CD38 PE-Cy7 (clone HIT2), CD90 PE (clone PR13), CD34 APC (clone 563), CD45RA Pac Blue (clone HI100).

Bone marrow and spleen cell preparation for analysis. Mice were euthanized and bone marrow (hips, femurs, tibia, spine) and spleen were harvested. Bones were crushed in PBS+2% bovine calf serum (BCS) into single cell suspensions and filtered through 70-μm filter (Falcon). Spleens were mashed direct in 70-μm filter (Falcon). RBC lysis was performed with ACK lysis buffer for 10 min at RT. Cells were rinsed, filtered again and counted on a Countess automated cell counter (Invitrogen).

Bone marrow cell preparation and HSC isolation for transplantation experiments. For preparation of total bone marrow cells hips, femurs, tibia and spine from donors were harvested and crushed in PBS+2% fetal bovine serum (FBS). Cells were filtered through 70-μm filter, lysed in ACK lysis buffer and counted on Invitrogen Countess. For HSC (LSK; Lin⁻ Sca1⁺c-Kit⁺) transplants, total bone marrow cells were lineage depleted using magnetic column separation and direct lineage cell depletion kit (MACS Separation Columns LS; Miltenyi Biotec) per manufacturer instructions. Lin⁻ cells were stained for surface markers for 20 min at RT in the dark, washed and sorted on BD FACSAria II. Prior to sort propidium iodide was added to exclude dead cells. Whole bone marrow or LSK-sorted cells were resuspended in PBS+2% FBS and injected into recipients retroorbitally in 100 μl cell suspensions.

Statistical analysis. Mann-Whitney U test and Kruskal-Wallis one-way ANOVA were performed using GraphPad Prism software. P values <0.05 were reported as statistically significant. Kaplan-Meier survival curves were analyzed by log-rank test.

Hematoxylin and Eosin (H&E) staining of bone marrow sections. Histology was performed by HistoWiz Inc. using a Standard Operating Procedure and fully automated workflow as follows: mouse femurs were formalin fixed, embedded in paraffin, and sectioned at 4 μm. After staining, sections were dehydrated and film coverslipped using a TissueTek-Prisma and Coverslipper (Sakura). Whole slide scanning (40×) was performed on an Aperio AT2 (Leica Biosystems).

In vitro cell culture, imaging and viability assay. Fibronectin coated 96-well flat-bottom plates were used for the murine experiments. Briefly bovine plasma fibronectin (Sigma-Aldrich, F1141) was reconstituted in 0.1% BSA+ PBS w/o Ca⁺⁺ and Mg⁺⁺ to a final concentration of 5 μg/ml and added to each well in volume 50 μl. After 1 h the fibronectin solution was aspirated from each well and the plate was left for an additional 1 h at RT to dry. Lin⁻Sca1⁺ c-Kit⁺CD48⁻ cells from the BM of B6 mice were sorted by FACS. After sorting, the cells were spun down at 0.5×g for 5 min and the cell pellet was reconstituted in HSC media, containing serum-free StemSpan media (STEMCELL Technologies), 10 ng/mL recombinant murine SCF (PeproTech) and 100 ng/mL recombinant murine thrombopoietin (PeproTech). 100 μl of cells in HSC media were plated to a density of 2000-3000 cells/well and left overnight at 37° C., 5% CO₂ to recover from sorting. For the human HSC, in vitro assay frozen cord blood or bone marrow CD34+ cells were purchased from STEMCELL Technologies and thawed in warm RPMI media, containing 10% FBS. 3000-4000 Lin⁻CD34⁺ CD38⁻ were directly sorted into 96-well plates, coated with human fibronectin (Corning® BioCoat™, Cat. #354409), containing 100 μl of serum-free StemSpan media, supplemented with 10 ng/mL human recombinant SCF (PeproTech), 100 ng/mL human recombinant TPO (PeproTech) and 40 μg/ml human LDL (StemCell Technologies, Cat. #02698). Plates were left overnight at 37° C., 5% CO₂ AZA was reconstituted in HSC media and added as 2× concentration (100 μl/well) to final AZA concentrations 0.1, 0.5 and 1 μg/ml at baseline and 24 h of cell culture. Cell imaging and cell counting was performed every 6 h by using the Imag-Express Pico automated imaging system, equipped with environmental control (5% CO₂, 85% humidity and 37° C.). After 48 h cells were stained with the EarlyTox Live/Dead Assay Kit (Molecular Devices) as per manufacturer instruction for 20 min followed by staining with 10 μM Hoechst 33342 nuclear dye for another 20 min at RT in the dark. Cells were imaged using ImageXpress Pico. Hoechst staining was used to identify total cells, Calcein AM to identify live cells and Ethidium homodimer-Ill (EthD-III) to identify death cells. Data analysis was performed on CellReporterXpress software (ImageXpress).

Whole blood transfusion. B6. Rag2cyc⁻/⁻ mice were euthanized and 500-700 μl whole blood per mouse was collected via cardiac puncture into heparinized syringes and transferred into eppendorf tubes, containing 2 μl of 0.2% Heparine solution (STEMCELL Technology). 100 μl of whole blood was immediately administered via retroorbital injection in recipient mouse.

Complete blood cell count. 20 μl of whole blood was collected via the tail vein and complete blood counts (CBC) were conducted using Heska HemaTrue Veterinary Hematology Analyzer (Heska). For more detailed CBC analyses, including reticulocyte counts and manual differentiation, 150 μl of whole blood was collected and processed in the Animal Diagnostic Laboratory in the Veterinary Service Center at Stanford University. Automated hematology was performed using the Sysmex XT-2000iV analyzer system. Blood smears were made for all CBC samples and reviewed by a medical technologist. Manual differentials were performed as indicated by species and automated analysis. Flagged abnormalities were additionally reviewed by a board-certified veterinary clinical pathologist.

Results

Figure 9:
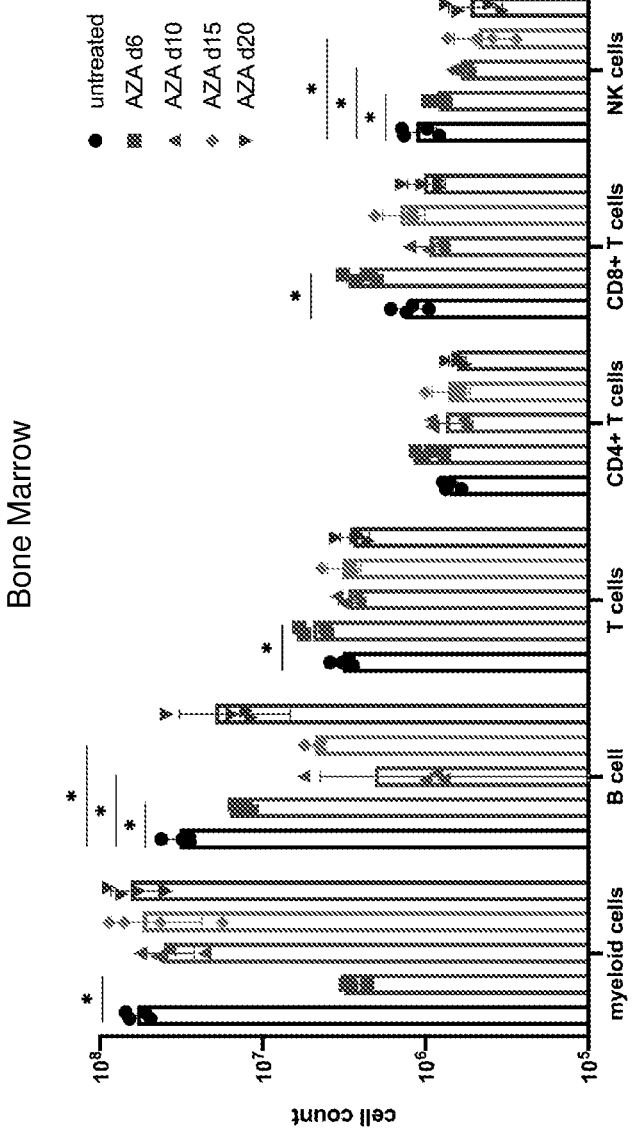
FIG. 9 shows depletion kinetics of mature myeloid and lymphoid cells following treatment with AZA 5 mg/kg/d for 5 days in BM (A) and Spleen (B). Myeloid cells (Gr1⁺ Mac1⁺), B cells (CD19⁺CD3⁻), T cells (CD3⁺CD19⁻), NK cells (NK1.1⁺CD3⁻), CD4 cells (CD3⁺CD4⁺), CD8 cells (CD3⁺CD8⁺). Data represent mean±SD (n=4 per group per timepoint). Statistics were calculated by Mann-Whitney test between control and treated groups for the different timepoints; *P<0.05.
Figure 9:
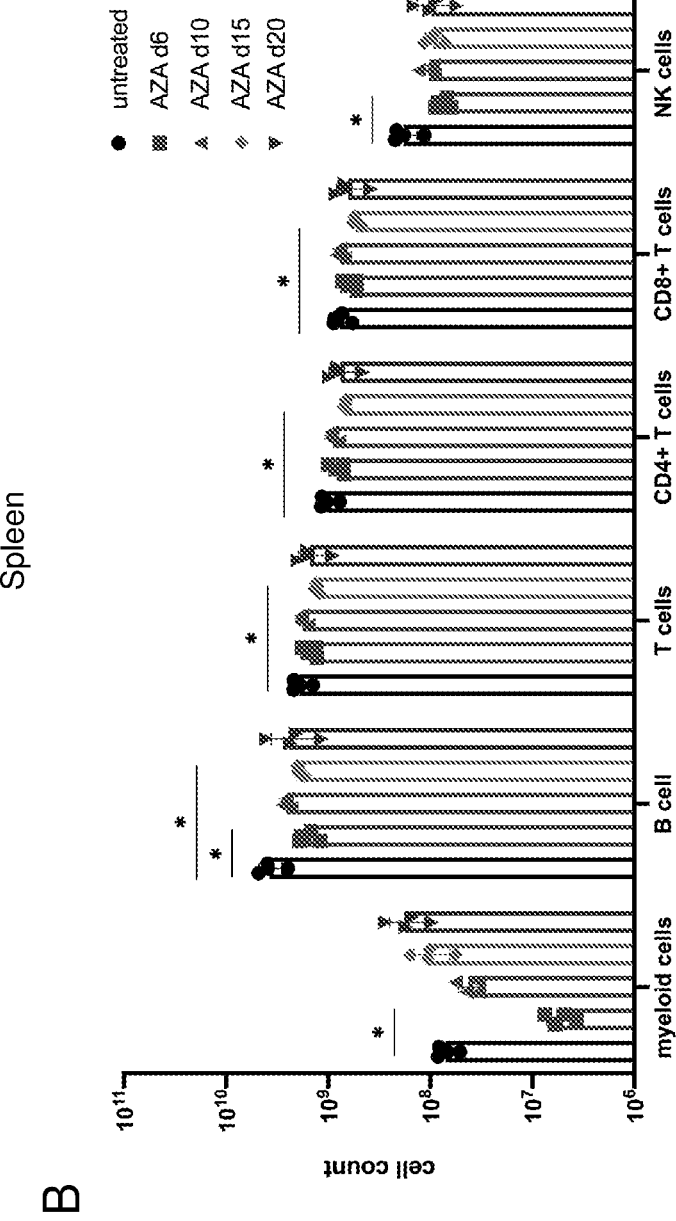

AZA depletes mature and hematopoietic stem and progenitor cells. We sought to study the effect of AZA on normal hematopoiesis and determined that AZA causes depletion of both mature and hematopoietic stem and progenitor cell (HSPC) populations in vivo. Immunocompetent C57BL/6 (B6) mice were treated with 5 mg/kg/d AZA for 5 consecutive days and the blood, spleen, and bone marrow (BM) were analyzed by extended phenotype analysis on days 6, 10, 15 and 20 after initiation of AZA treatment (FIG. 1A). In the blood, transient reduction in all lineages except platelets was observed, including decreases in hemoglobin (Hb), white blood cell count (WBC), granulocytes, lymphocytes, and monocytes with the lowest values documented on day 10 (FIG. 1B). Granulocytes were the most affected showing an approximate 4-fold reduction. All blood subsets recovered to normal range values by day 20. Splenic myeloid cells were significantly reduced on day 6, but rebounded to normal levels by day 10, whereas splenic lymphocyte populations were only slightly affected by AZA treatment (FIG. 9B).

Figure 6:
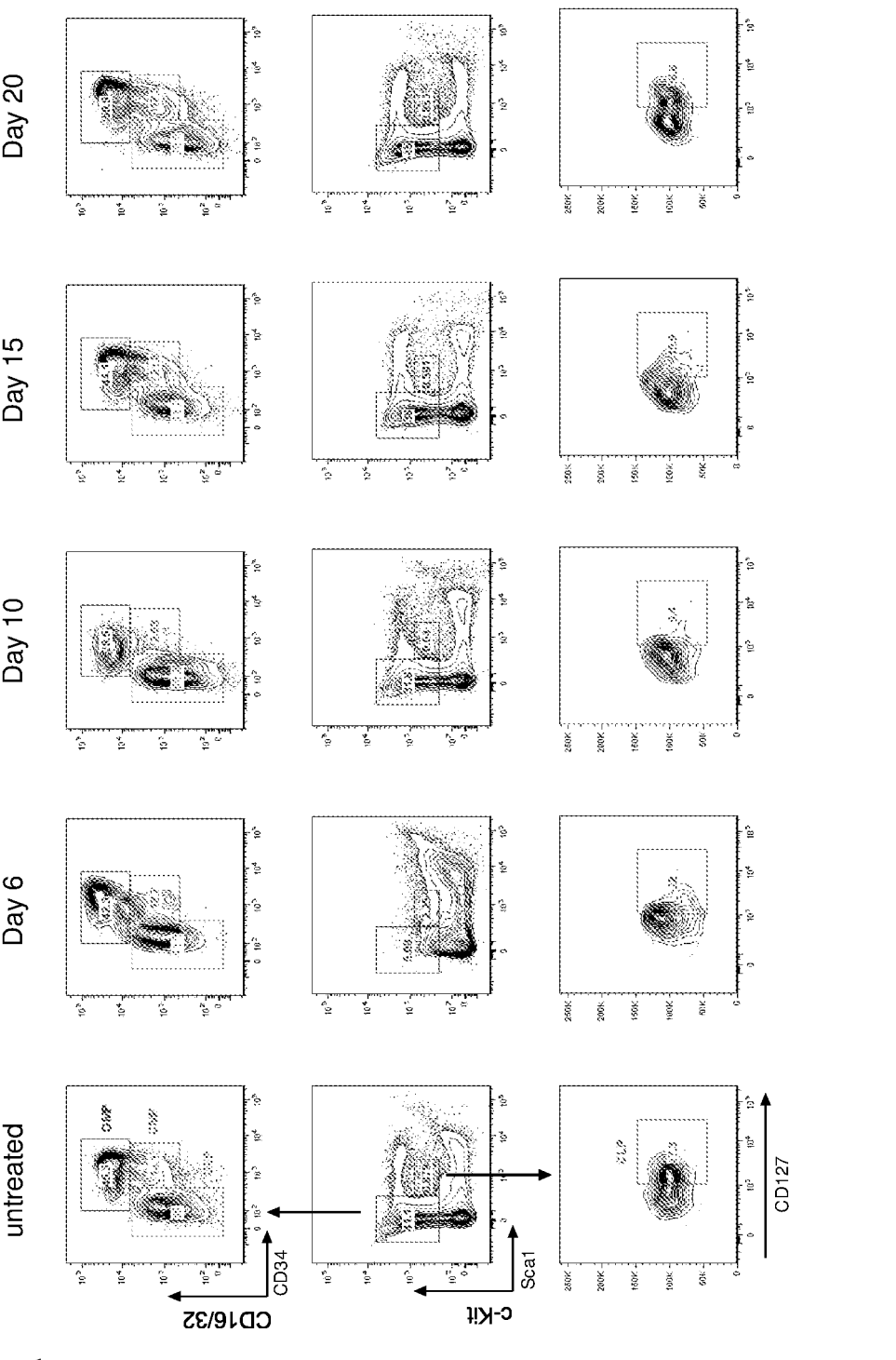
FIG. 6 shows (A) Flow cytometric analysis of the myeloid and lymphoid progenitors in the BM of mice treated with AZA 5 mg/kg/d for 5 days at day 6, 10, 15 and 20 as compared to untreated controls. Myeloid progenitors (MP) are gated from live, Lin⁻Sca1⁻c-Kit⁺ cells and common lymphoid progenitors (CLP) are gated from live, Lin⁻Sca1$^{dim}$c-Kit$^{dim}$ cells. Megakaryocyte-erythrocyte progenitors (MEP), granulocyte-monocyte progenitors (GMP), common myeloid progenitors (CMP). (B) Absolute number of MEP, CMP, GMP and CLP in the BM at day 6, 10, 15 and 20 after 1$^{st}$ AZA dose as compared to untreated control mice. Data represent mean±SD (n=4 per group per timepoint). Statistics were calculated by Mann-Whitney test between control and treated groups for the different timepoints; *P<0.05.
Figure 6:
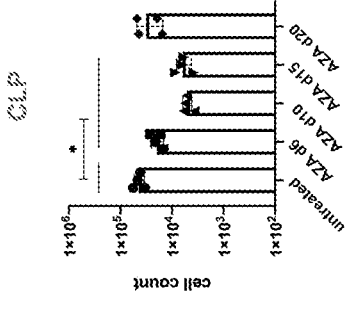
Figure 6:
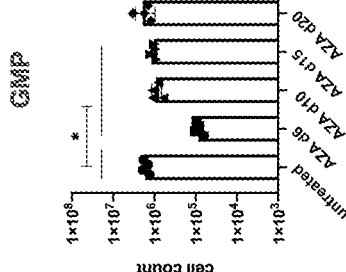
Figure 6:
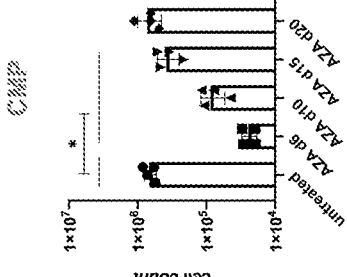
Figure 6:
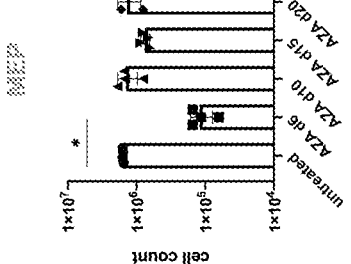

In contrast to the relatively mild effects in the peripheral hematopoietic compartment, impact on the hematopoietic cells in the BM was more substantial. Although overall cellularity was decreased on day 6 [80% from baseline, p value=0.0286, FIG. 1C-D] and recovered by day 10, analyses of the different BM subpopulations showed that AZA resulted in marked depletion of all CD117+BM cells including HSC, Multi-Potent Progenitors (MPP) and downstream lineage-restricted progenitors (FIG. 1E). Both LT-HSC (Lin⁻Sca1+c-Kit⁺[LSK]CD150⁺CD48⁻) and ST-HSC (LSKCD150⁻CD48⁻) were noted to be markedly reduced, nadiring day 6 at 15-fold and 24-fold, respectively; and recovery of the ST-HSC fraction was delayed beyond day 20 (FIG. 1F). Common myeloid progenitors (CMP), granulocyte-macrophage progenitors (GMP) and megakaryocyte-erythrocyte progenitors (MEP) were also substantially depleted (>25-, >18- and >11-fold, respectively) by day 6. MEP promptly recovered by day 10, whereas CMP and GMP recovery was delayed beyond day 15 (FIGS. 6A and B).

Figure 7:
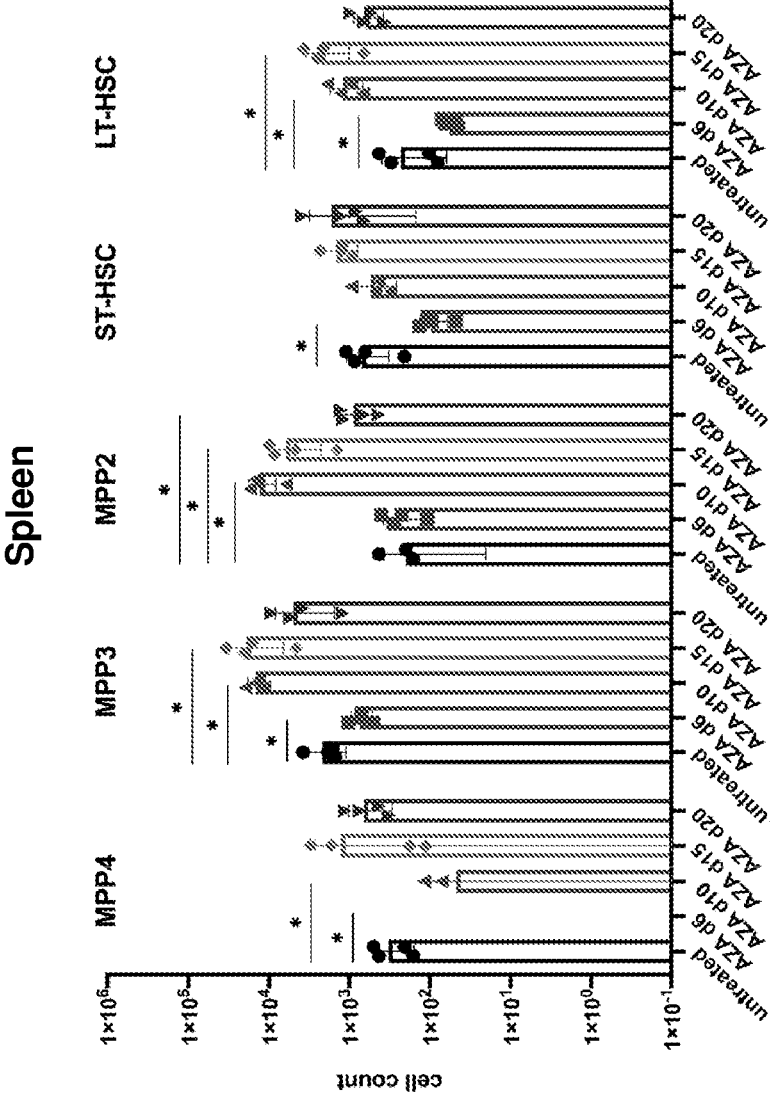
FIG. 7 shows the absolute number of the different HSPC compartments in the spleen at day 6, 10, 15 and 20 following AZA treatment as compared to untreated control mice. Multipotent progenitors (MPP); MPP4: Lin⁻Sca1⁺c-Kit⁺ (LSK)CD150⁻CD48⁺Flt3⁺; MPP3: LSKCD150⁻ CD48⁺ Flt3⁻; MPP2: LSKCD150⁺CD48⁺; Short-term HSC (ST-HSC): LSKCD150⁻CD48⁻; long-term HSC (LT-HSC): LSKCD150⁺CD48⁻. Data represent mean±SD (n=4 per group per timepoint). Statistics were calculated with Mann-Whitney test (*P<0.05).

Examination of the HSC populations in the spleen did not support the idea that mobilization of LT-HSC and ST-HSC to secondary organs was the cause of the decrease in BM (FIG. 7). Rather, ST- and LT-HSC in the spleen were also observed to decrease on day 6 with rebound of LT-HSC by day 10, although given the smaller numbers of HSC that reside in the spleen, the depletion was less pronounced than in the BM.

Figure 8:
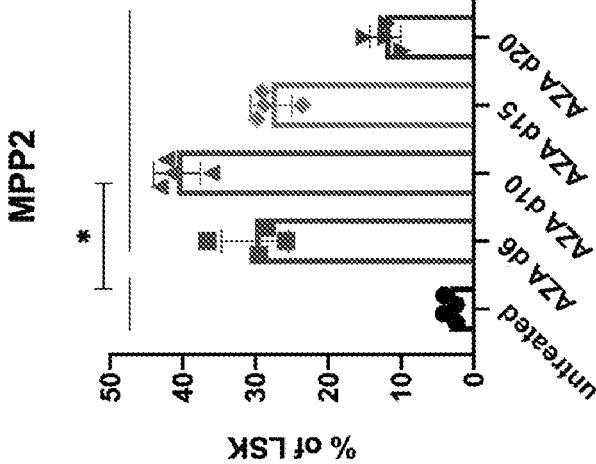
FIG. 8 shows BM MPP3 and MPP2 as % of LSK at day 6, 10, 15 and 20 following AZA treatment as compared to untreated control mice. Data represent mean±SD (n=4 per group per timepoint). Statistics were calculated with Mann-Whitney test (*P<0.05).
Figure 8:
Figure 8:
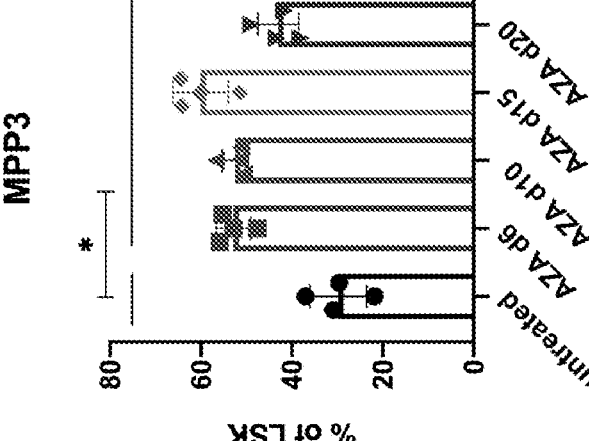

BM depletion of HSC was followed by rapid expansion of myeloid-biased multipotent progenitors, defined phenotypically as LSKCD150+CD48+(MPP2) and LSKCD150-CD48+Flt3-(MPP3), reflected by a proportional shift by day 6 in these cells amongst LSK HSPC (FIG. 1F, FIG. 8). In comparison, the pattern of lymphoid-biased progenitors, MPP4 (LSKCD150-CD48+Flt3⁺), and common lymphoid progenitors (CLP; Lin⁻Sca1ᵈⁱᵐc-KitᵈⁱᵐCD127⁺), was depletion reaching nadirs on day 10 and recovery by day 20 (FIG. 1F and FIG. 6B); and the dynamics of recovery of these populations were not as striking as the MPP2 expansion. Another notable effect of AZA in the BM was marked and prolonged depletion of B cells as assessed by the CD19 marker. Maximal B cell depletion of >30-fold occurred at day 10 and did not recover until >day 15 after AZA treatment (FIG. 9A). BM NK-cells were also noted to transiently decline, whereas CD8+ T cells were transiently increased, normalizing by day 10.

Figure 2:
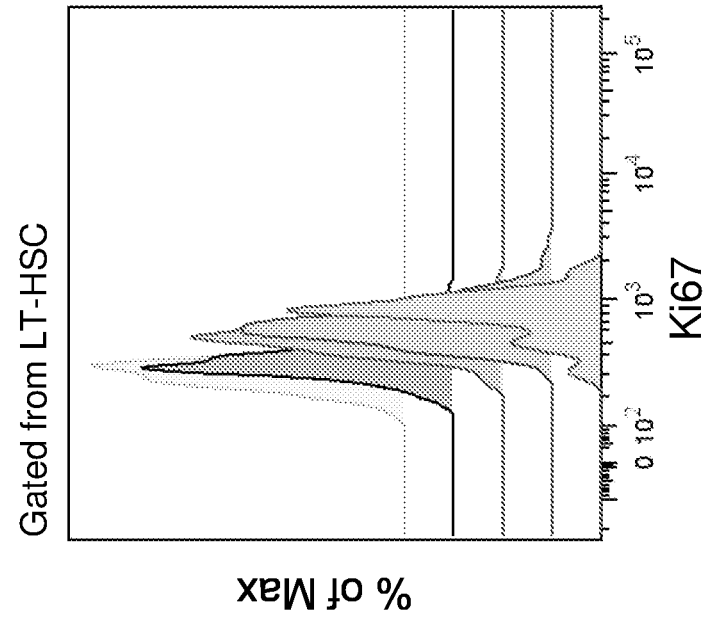
FIG. 2 shows AZA induces HSC-proliferation in vivo and reduces growth and viability of proliferating HSC in vitro. A. Schematic of treatment protocol. C57BL/6 mice were injected with three different doses of AZA (1.25, 2.5 and 5 mg/kg/d) for 3 days. 24 h after last AZA injection BM was analyzed for HSC-depletion and Ki67 intracellular protein expression. B. Overlay histogram of Ki67 intracellular protein expression in LT-HSC (gated from live, Lin⁻Sca1⁺c-Kit⁺CD150⁺CD48⁻ cells) in mice treated with AZA 1.25 mg/kg, 2.5 mg/kg and 5 mg/kg/d for 3 consecutive days. C. Mean fluorescence intensity (MFI) of Ki67 intracellular protein expression in LT-HSC, ST-HSC, MPP2, MPP3/4 and myeloid progenitors (MP). Data were pooled from 2 independent experiments and represent mean±SD (n=7). Statistics were calculated Mann-Whitney test (*P<0.05; P<0.01; *P<0.001). D. Schematic of in vitro culture protocol. Mouse Lin⁻Sca1+c-Kit⁺CD48⁻ or human Lin⁻CD34⁺CD38⁻ were FACS-sorted and plated in 96-well flat bottom plate, coated with fibronectin and containing 100 μl of HSC media/well, supplemented with 10 ng/ml SCF and 100 ng/ml TPO. Different concentrations of AZA (0.1, 0.5 and 1 μg/ml) were added on two consecutive days (at baseline and 24 h after cell culturing) and cell counting, and cell imaging was performed every 6 h for total of 48 h on ImagExpress Pico automated cell counting system. After 48 h % live/dead cells was assessed by using EarlyTox Live/Dead Assay Kit. E. Proliferation curves of FACS-sorted mouse Lin⁻Sca1⁺c-Kit⁺CD48⁻ in the presence of indicated concentrations of AZA (left) and cell viability as assessed by % of Calcein AM positive cells after 48 h of cell culture (right). Data represent mean±SD from 3 independent experiments. Statistics were calculated with Mann-Whitney test (*P<0.05; P<0.01; *P<0.001). F. Proliferation curves of FACS-sorted human Lin⁻CD34⁺CD38⁻ cells in the presence of indicated concentrations of AZA (left) and cell viability as assessed by % of Calcein AM positive cells after 48 h of cell culture (right). Data represent mean±SD from 2 independent experiments. Statistics were calculated with Mann-Whitney test (P<0.01; *P<0.001).
Figure 2:
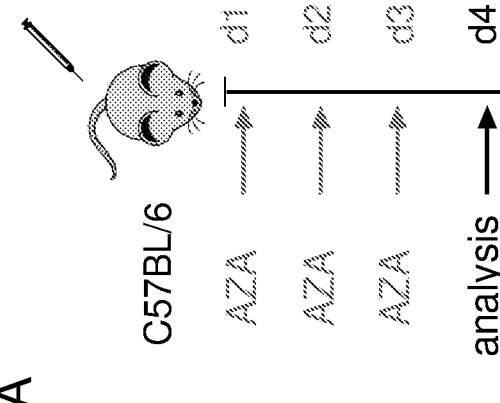
Figure 2:
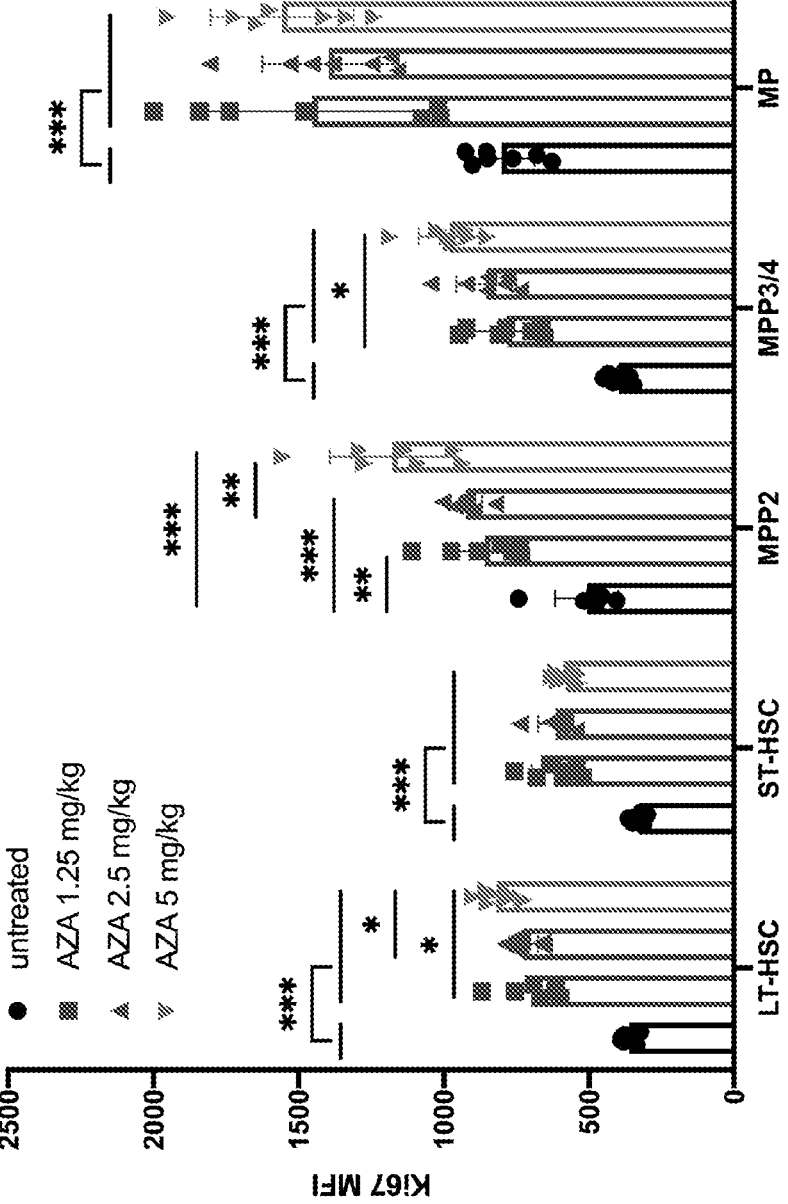
Figure 2:
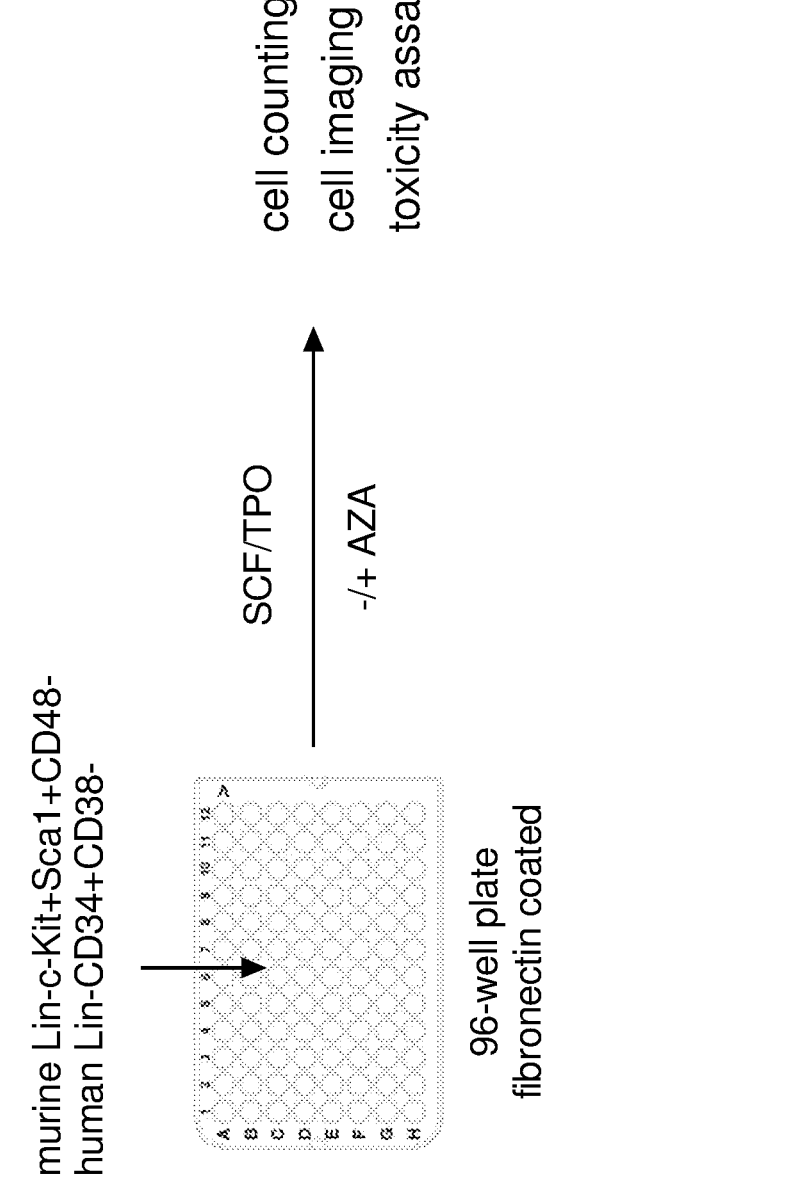
Figure 2:
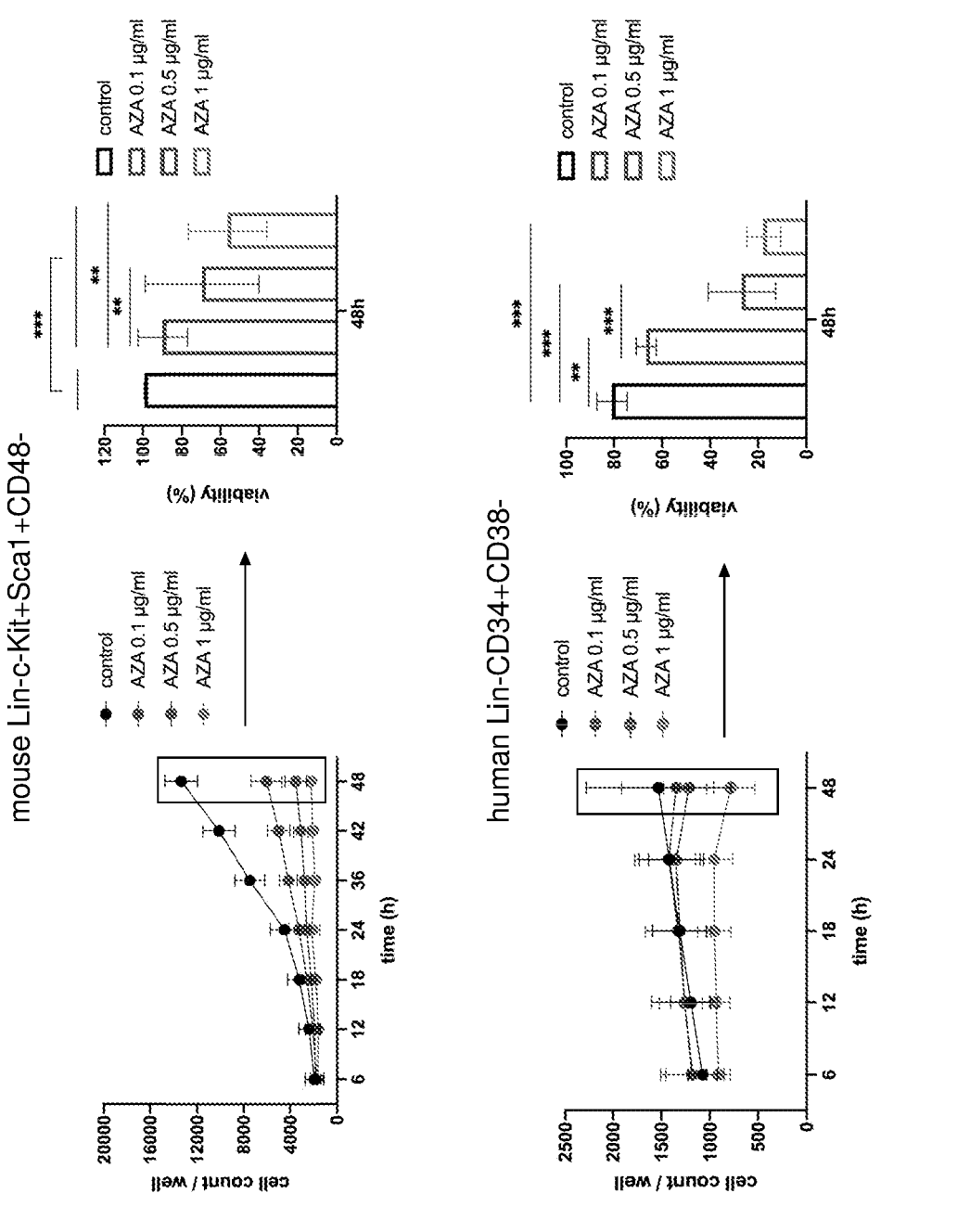
Figure 10:
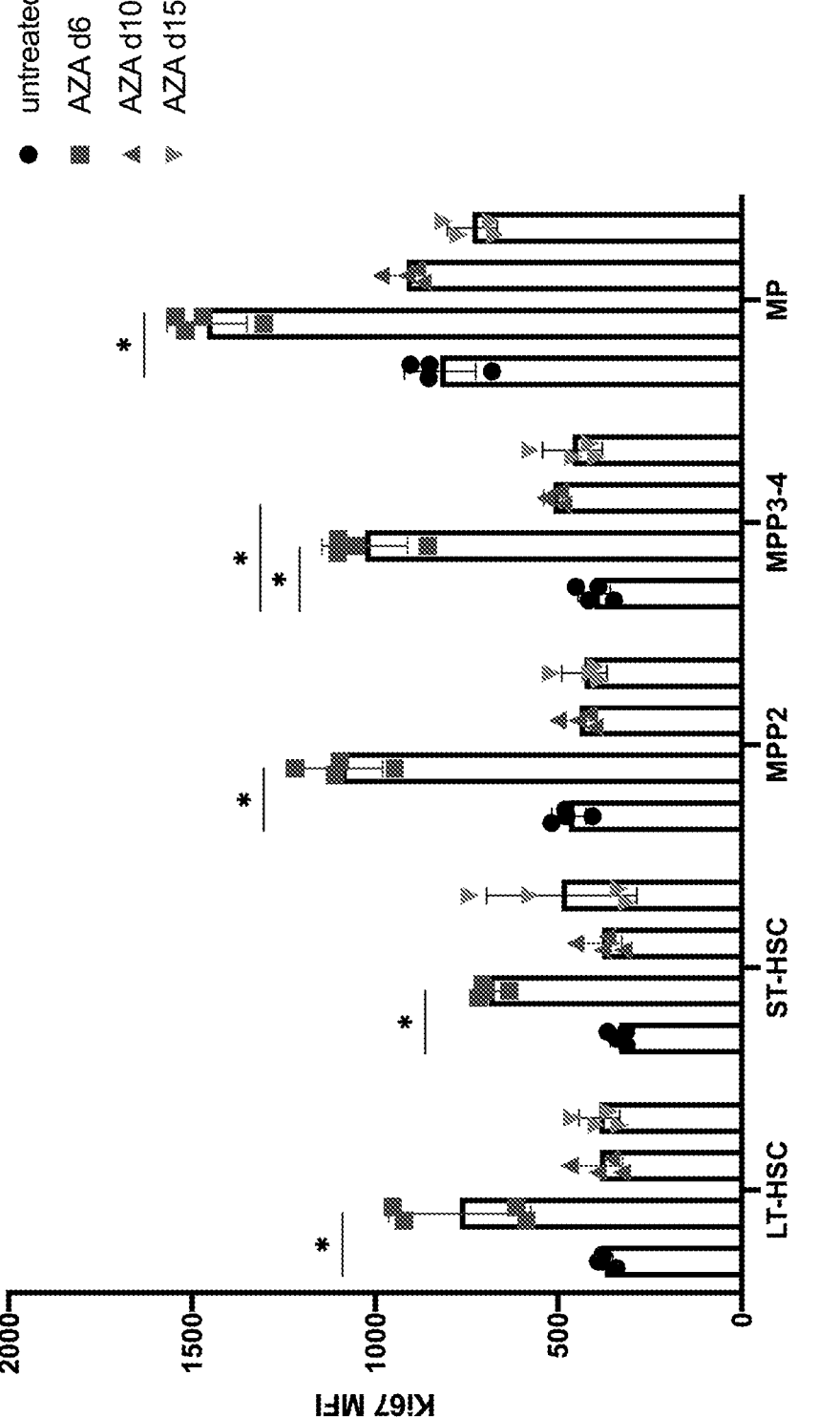
FIG. 10 shows mean fluorescence intensity (MFI) of Ki67 intracellular protein expression in LT-HSC, ST-HSC, MPP2 and MPP3/4. Data were pooled from 2 independent experiments and represent mean±SD (n=7). Statistics were calculated Mann-Whitney test (*P<0.05; P<0.01; *P<0.001).
Figure 11:
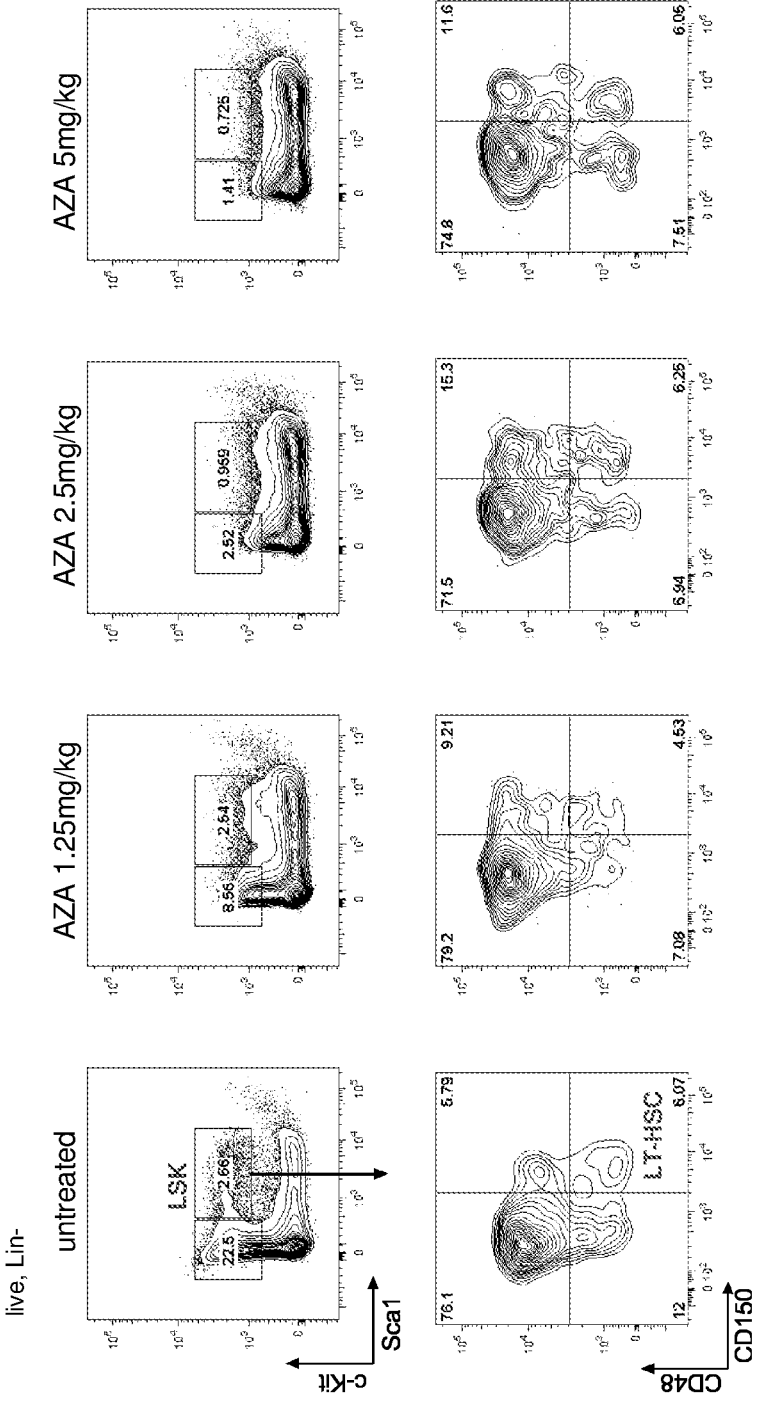
FIG. 11 shows (A) Flow cytometric analysis of the hematopoietic stem and progenitor cell (HSPC) compartment in the BM of untreated controls and mice treated with three different AZA doses (1.25, 2.5 and 5 mg/kg/d) for 3 days. Analysis was performed 24 h after last AZA administration. Gated from lineage negative (Lin⁻) live cells. Lin⁻Sca1⁺c-Kit⁺⁺ cells (LSK), long-term hematopoietic stem cells (LT-HSC). (B) Absolute number of LSK and LT-HSC in the bone marrow of mice following treatment with AZA 1.25, 2.5 and 5 mg/kg/d for 3 days as compared with untreated controls. Data were pooled from 2 independent experiments and represent mean±SD (n=7). Statistics were calculated Mann-Whitney test (P<0.01; *P<0.001).
Figure 11:
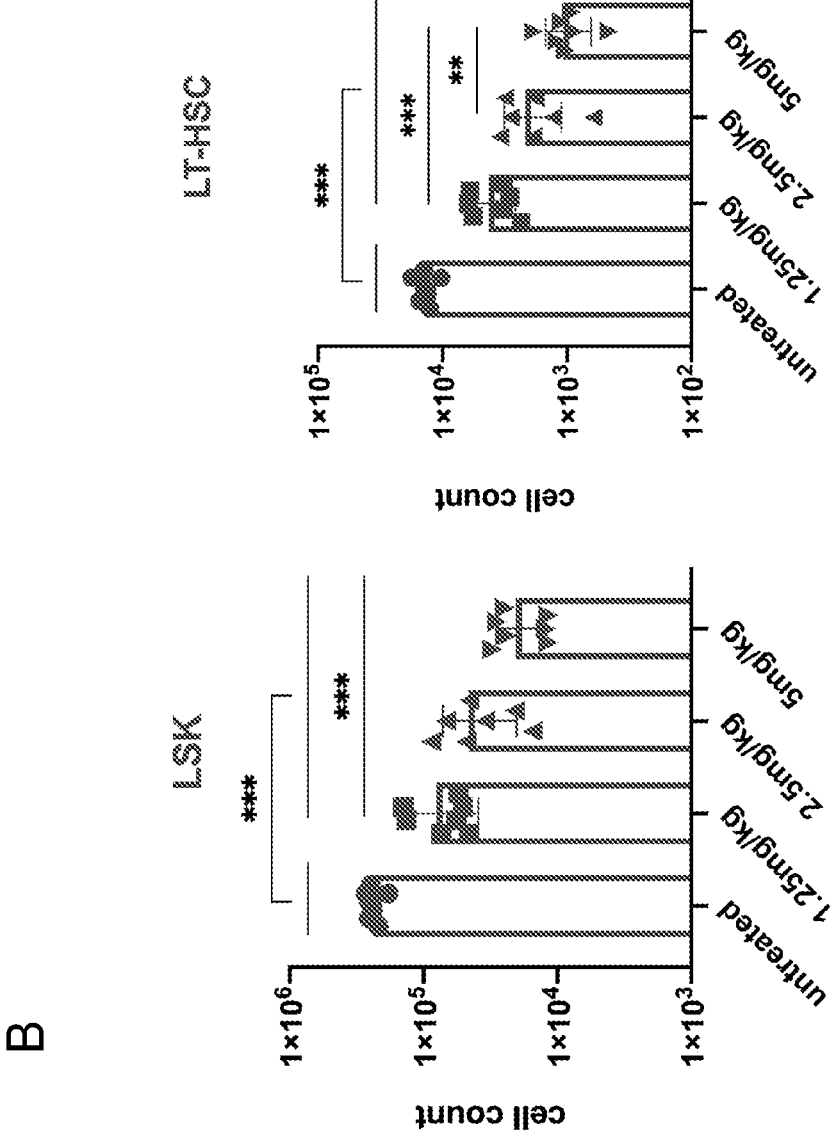

AZA-induced HSC proliferation in vivo is responsible for the direct toxic effects of the drug on HSC. In vivo depletion of HSC by AZA has not been previously reported, and was surprising given that most HSC are quiescent, and non-proliferating cells are known to be insensitive to the toxicities of AZA. Given the rapid recovery of the mature myeloid lineage, which was reflected in the shift of hematopoiesis towards the more actively cycling MPP2/3 fractions, we hypothesized that depletive effects of AZA on mature BM cells might induce early activation of dormant HSC and thus explain the increased sensitivity of this cell population to the effects of the drug in vivo. We therefore sought to better characterize the proliferative state of the entire HSPC compartment following treatment with AZA. B6 mice were injected with AZA 5 mg/kg/d for 5 days and Ki67 protein expression of LT-HSC, ST-HSC, MPP2 and MPP3/4 was assessed on day 6, 10 and 15. We observed significant increase of Ki67 in both HSC and MPP at day 6, which normalized by day 10 (FIG. 10). We noted, however, that the marked reduction of these HSPC subsets permitted analyses of only relatively rare events. Hence, in order to increase the sensitivity of these Ki67 analyses and confirm that AZA treatment can indeed activate quiescent HSC, the dose of AZA administered to mice was titrated down, and depletion and Ki67 analyses performed after 3 instead of 5 days of treatment (FIG. 2A). At the lowest dose of 1.25 mg/kg/d overall depletion of HSPC (as assessed by LSK phenotype) and LT-HSC still occurred to a level of –25% of baseline. However, this reduction was far less than the reduction caused by the 2.5 and 5.0 mg/kg dose respectively (FIGS. 11A and B). In all three dose regimens significant increase in Ki67 protein expression in HSC, MPP and MP compartments was detected (FIGS. 2B and C), pointing towards activation of hematopoiesis in response to the myelosuppressive effects of AZA.

To confirm the direct effects of AZA on the survival of actively proliferating mouse and human HSC in vitro we FACS-purified and cultured mouse LSKCD48⁻ or human Lin⁻CD34+CD38-cells (which contain both LT and ST-HSC) in the presence of SCF and TPO. AZA at concentration 0.1, 0.5 and 1 μg/ml was added to the cell culture on two consecutive days (at baseline and after 24 h). The concentration range was chosen based upon the plasma concentration range documented in patients after subcutaneous administration of 75 mg/m² AZA (Cmax=750±403.3 ng/mL). Cell imaging and cell counting was performed every 6 h and live/dead toxicity assay at 48 h by using ImagExpress Pico automated cell counting system (FIG. 2D). In both mouse and human HSC cultures AZA reduced the number of cells in a dose dependent manner and showed significant decrease in cell viability as assessed by Calcein AM when used in concentrations 0.1 μg/ml (FIG. 2E-F).

Figure 12:
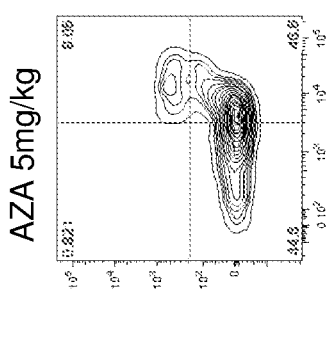
FIG. 12 shows (A) Flow cytometric analysis of Annexin V/PI staining of the Lin⁻Sca1⁺c-Kit⁺ cells (LSK) compartment in the of untreated controls and mice treated with three different AZA doses (1.25, 2.5 and 5 mg/kg/d) for 3 days. Analysis was performed 24 h after last AZA administration. Gated from LSK. (B) Annexin V+(left) and Annexin V/PI+(right) cells shown as % from LSK in the three different dose groups as compared to untreated controls. Data were pooled from 2 independent experiments and represent mean±SD (n=4 in the control group and n=7 in the AZA groups). Statistics were calculated Mann-Whitney test (*P<0.05; **P<0.01).
Figure 12:
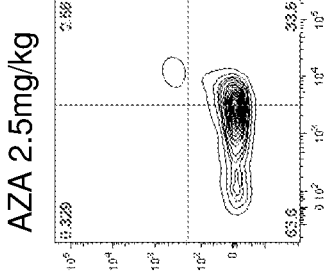
Figure 12:
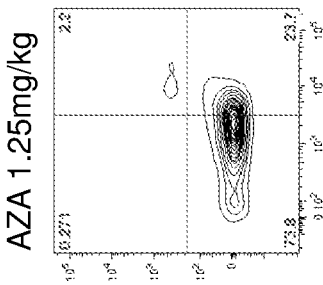
Figure 12:
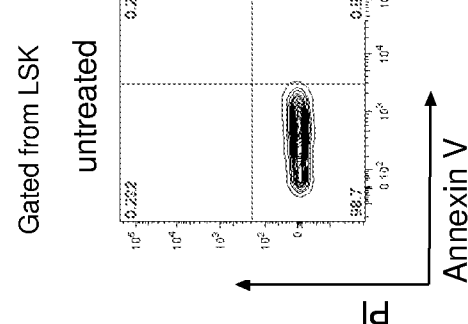
Figure 12:
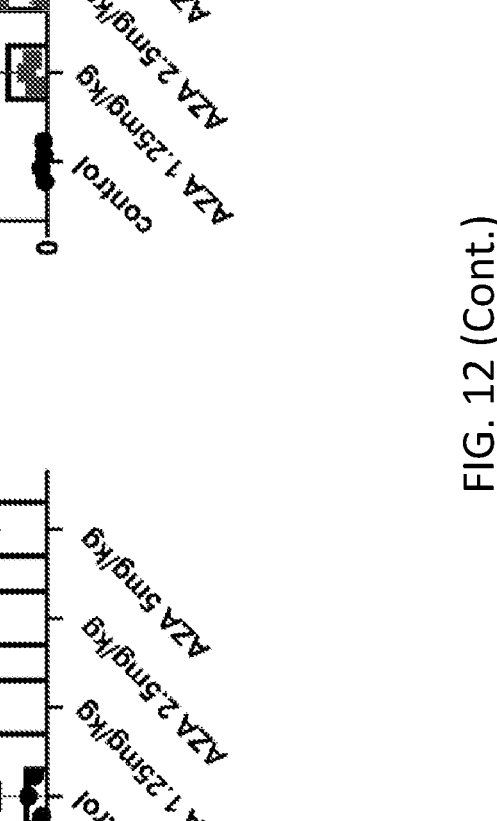

In vivo direct killing by apoptosis was confirmed by flow cytometry using Annexin V/PI to stain the HSPC fractions. Increases in apoptosis and apoptotic cell death in the HSPC compartment were dose dependent and were already detectable after 3 days of treatment (FIGS. 12A and B). Collectively, these data suggest that AZA induces HSC proliferation in vivo, which increases the susceptibility of this population to the direct toxic effects of the drug.

Figure 3:
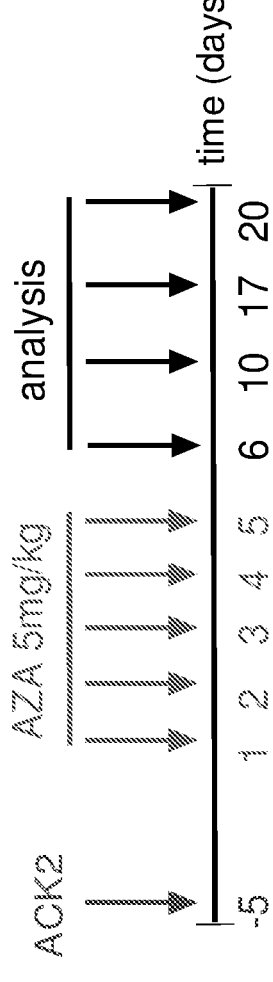
FIG. 3 shows anti-CD117 mAb (ACK2) in combination with AZA enhances HSC depletion and prolongs HSC recovery in vivo. A. Schematic of treatment protocol. C57BL/6 mice were injected retroorbital with single dose of ACK2 500 μg 5 days prior start treatment with AZA. AZA was administered in dose 5 mg/kg/d daily for 5 days. Mice were sacrificed 6, 10, 17 and 20 days after first dose of AZA and bone marrow (BM) and spleens were harvested and analyzed for HSC-depletion and depletion of mature myeloid and lymphoid cells. B. Hematoxylin and eosin staining of BM section from a mouse femur at day 6 from the in the ACK2 only group and the ACK2+AZA group. Magnification 100 μm. C. Absolute numbers of the different HSPC compartments in the BM and spleen of untreated controls and mice treated with ACK2 in combination with AZA at 6, 10, 17 20 days after start AZA as measured by flow cytometry; Lin⁻Sca1⁺c-Kit⁺(LSK)CD150+CD48⁻ (LT-HSC), LSKCD150⁻CD48⁻ (ST-HSC), LSKCD150⁺CD48⁺ (MPP2), LSKCD150⁻CD48⁺ (MPP3/4). Data represent mean±SD (n=3-4 per group per timepoint). Statistics were calculated Mann-Whitney test (*P<0.05). D. ACK2, but not 2B8 in combination with AZA significantly enhances and prolongs depletion of HSC in the BM of treated animals. Absolute number of ST-HSC and LT-HSC in the bone marrow of mice treated with AZA, 2B8+AZA and ACK2+AZA. ACK2 and 2B8 were administered as a single dose of 500 μg retroorbital 5 days prior treatment with AZA; AZA was given at dose 5 mg/kg/d for 5 days. BM was analyzed at d6, d10 and d20 after the start of AZA. Each treatment group represents an individual experiment with its own control group (baseline). Statistics were calculated by Kruskal-Wallis test (*P<0.05, ***P<0.001). E. Schematic of treatment protocol in C57BL/6 mice treated with recombinant murine stem cell factor (SCF) following treatment with ACK2+AZA. ACK2 in dose 500 μg was administered by intravenously by retroorbital injection 5 days prior start treatment with AZA. AZA was administered in dose 5 mg/kg daily for 5 consecutive days. Exogenous SCF was injected intraperitoneally at a dose of 1 μg/d for 5 consecutive days following treatment with AZA. Mice were sacrificed at day 11 after first dose of AZA and BM and spleen were analyzed for HSC-depletion. F. Flow cytometry analysis of HSPC compartments in untreated control and mice treated with ACK2+AZA+SCF as compared to mice treated with ACK2+AZA. Gated from live, Lin⁻ cells. G. Absolute numbers of LT-HSC, ST-HSC, MPP2 and MPP3/4 in the BM following treatment with ACK2+AZA (d11), with or without the addition of recombinant SCF. BM was harvested from both legs. Data were pooled from 2 independent experiments and represent mean±SD (n=8 per group). Statistics were calculated by Mann-Whitney test (*P<0.05, ns=non-significant).
Figure 3:
Figure 3:
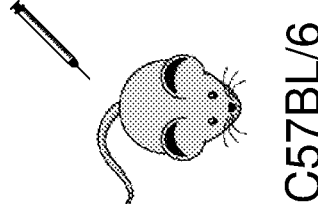
Figure 3:
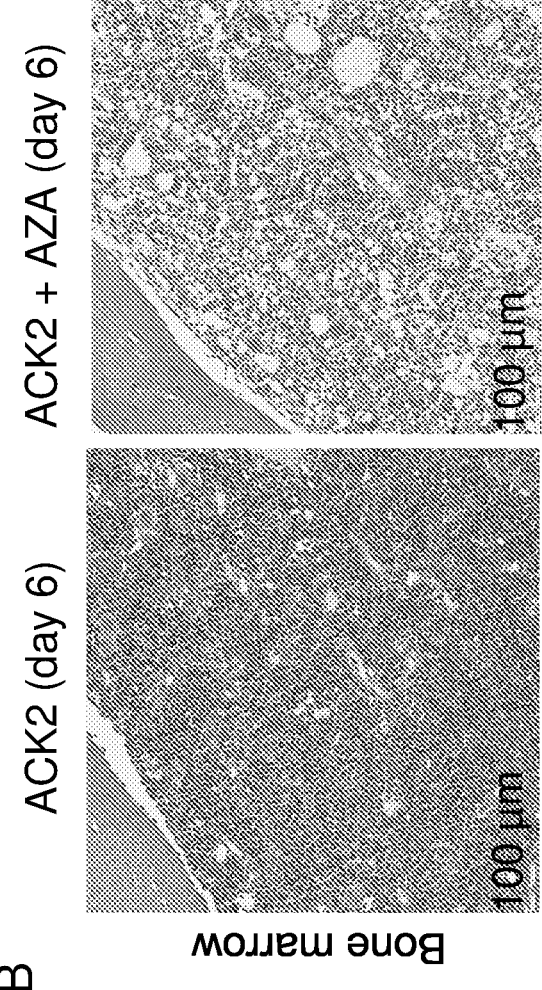
Figure 3:
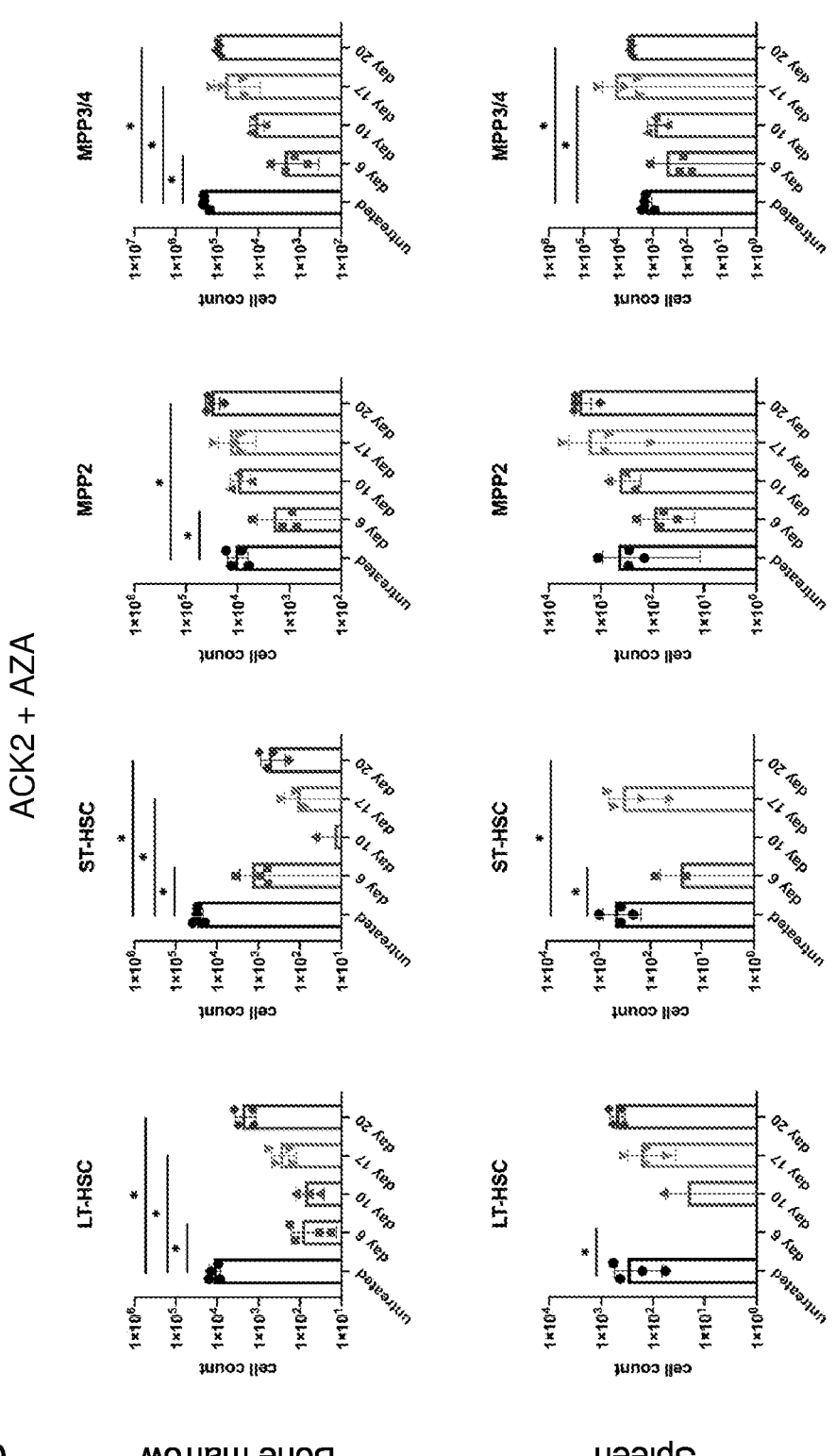
Figure 3:
Figure 3:
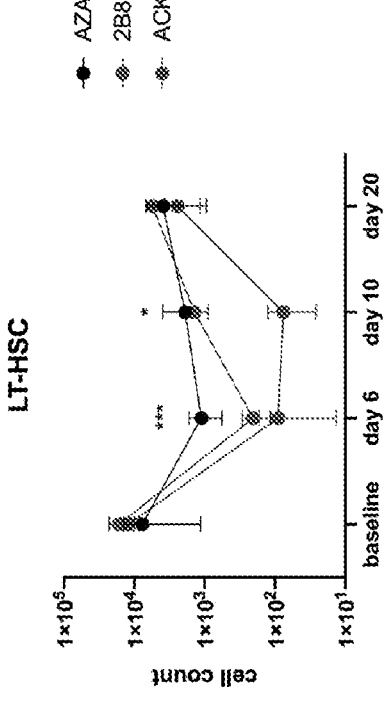
Figure 3:
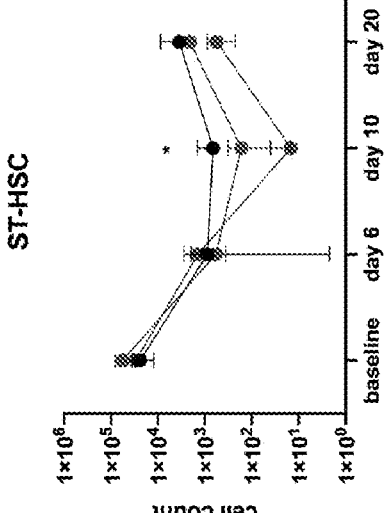
Figure 3:
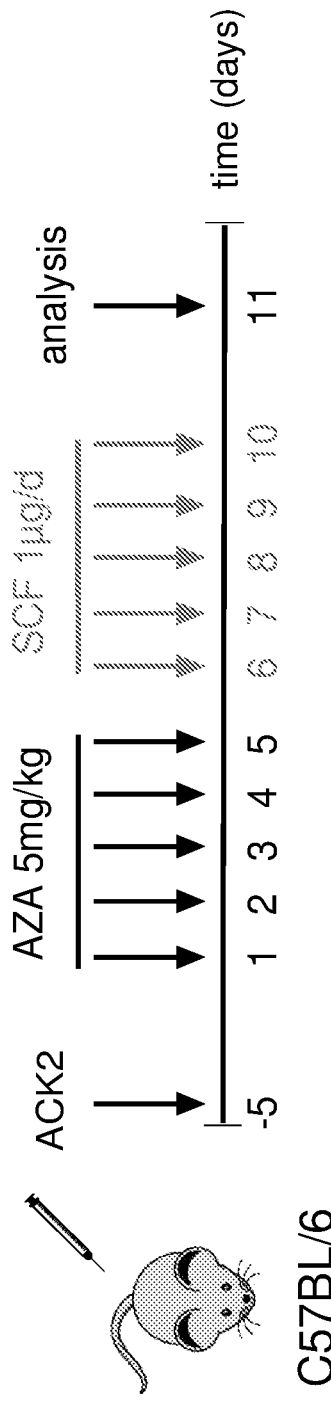
Figure 3:
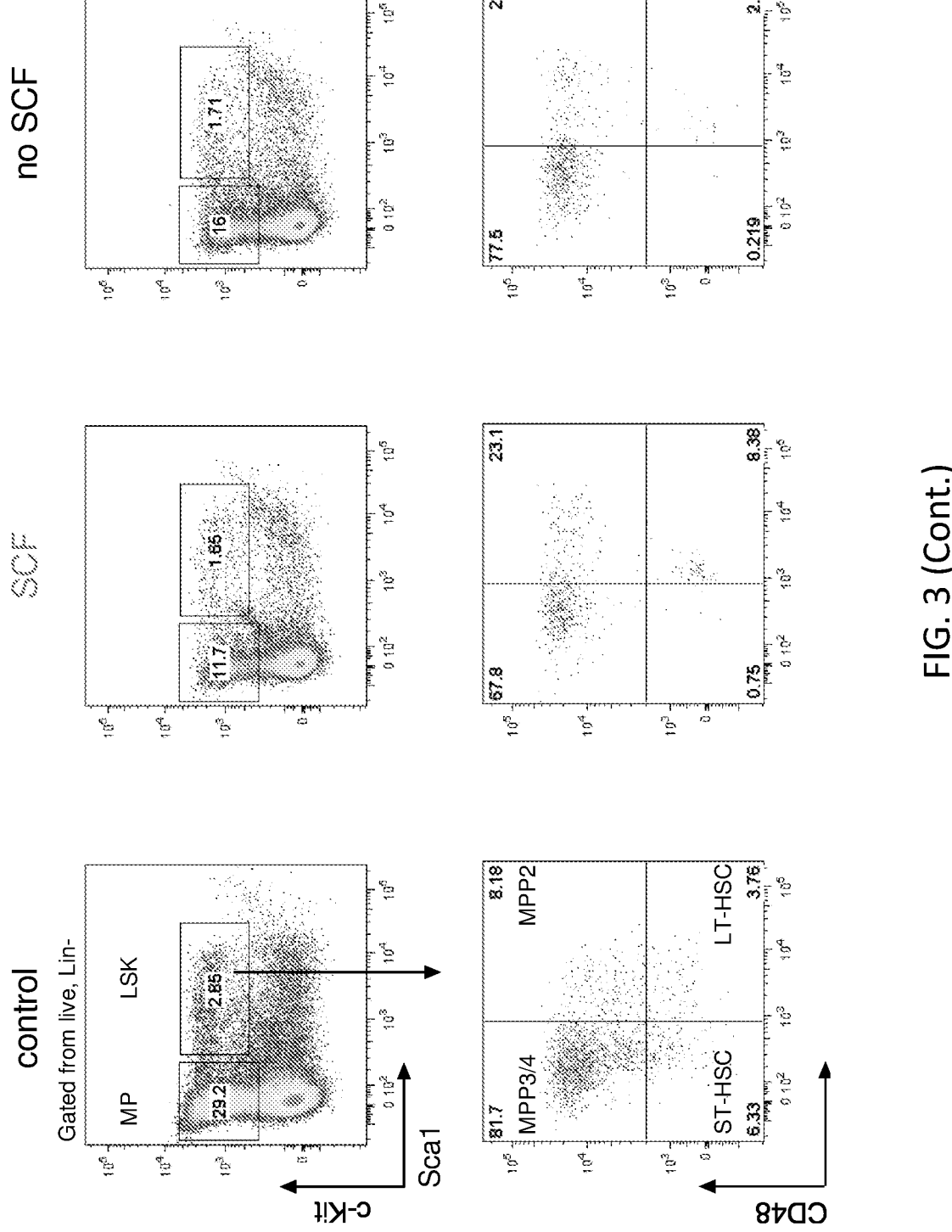
Figure 3:
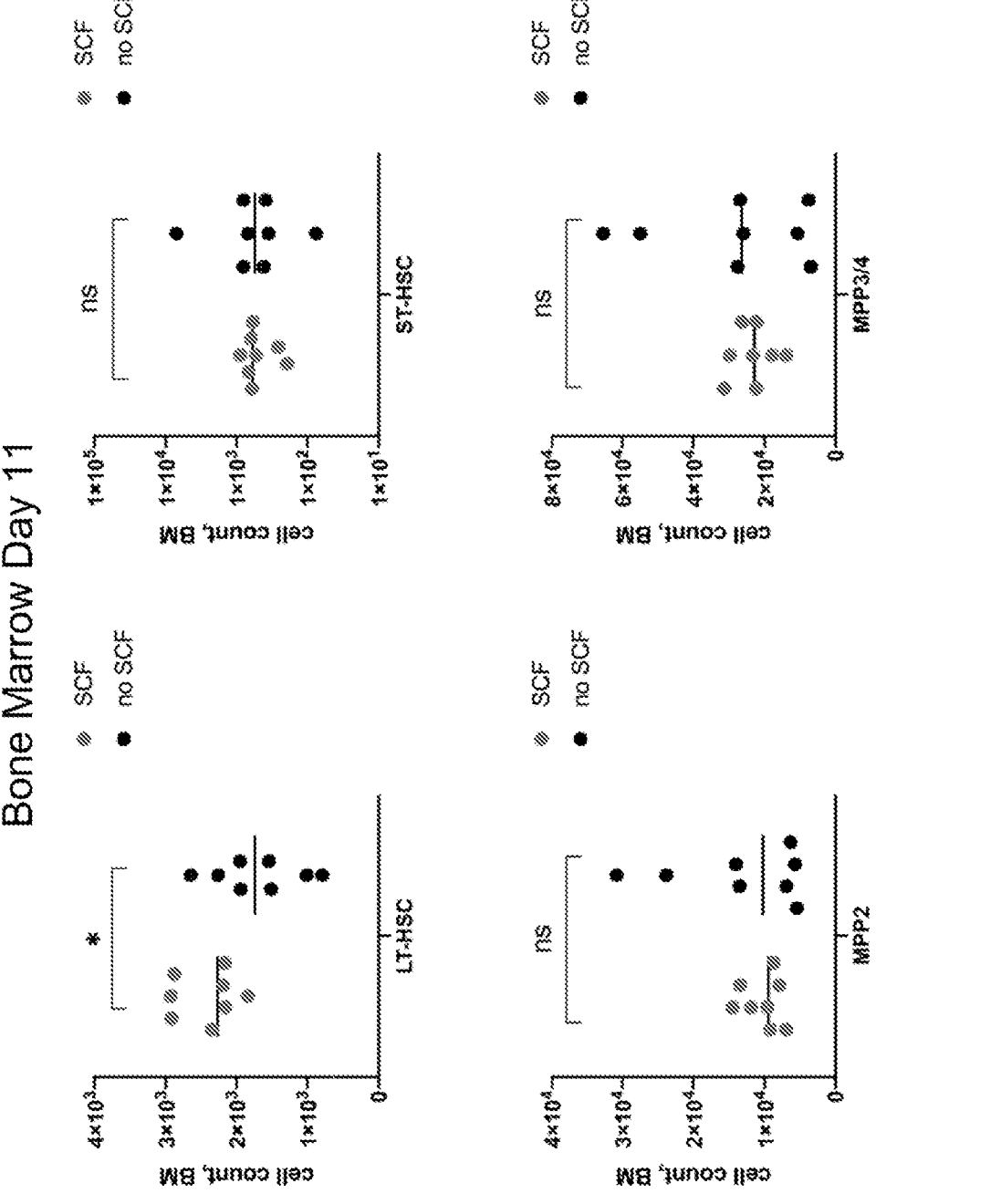
Figure 13:
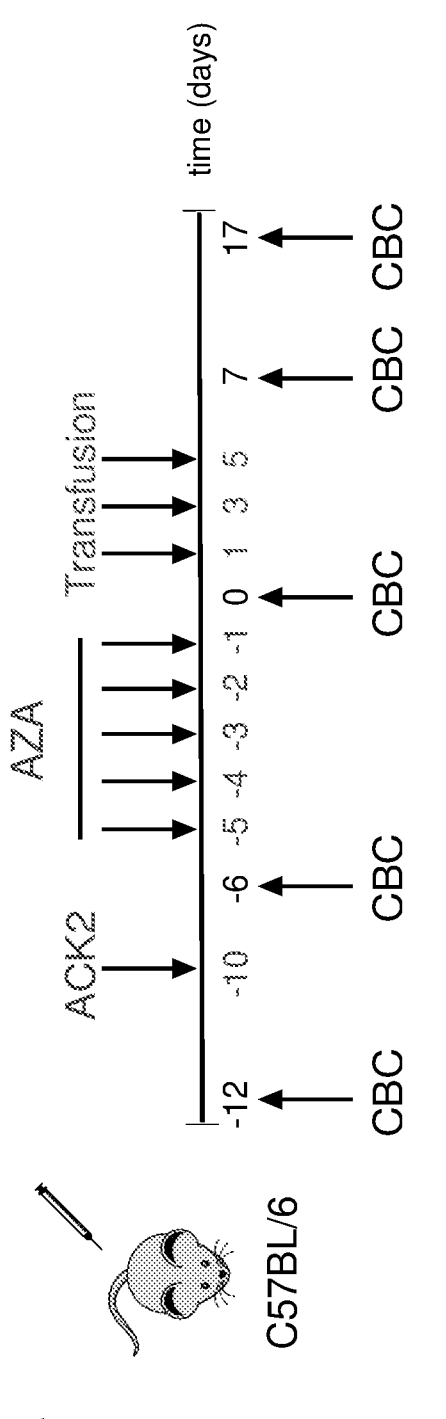
FIG. 13 shows transient myelosuppression with complete autologous recovery of peripheral blood parameters following treatment of ACK2+AZA. (A) Schematic of experiment. ACK2 was administered 5 days prior start 5-AZA. Transfusion group received 1000 of whole blood from B6. Rag2cyc⁻/⁻ mice every second day (cumulative ×3 transfusion) following treatment discontinuation. CBC were collected before start ACK2, before start 5-AZA and after treatment on days 0, 7 and 17. Mice were assessed twice weekly for signs of morbidity and mortality for 2 months. (B) Kaplan-Meier survival curve showing 100% survival in treated mice. (C) Complete blood cell counts (CBC) at different timepoints following ACK2+AZA treatment and ACK2+AZA+Transfusion treatment as compared to untreated controls.
Figure 13:
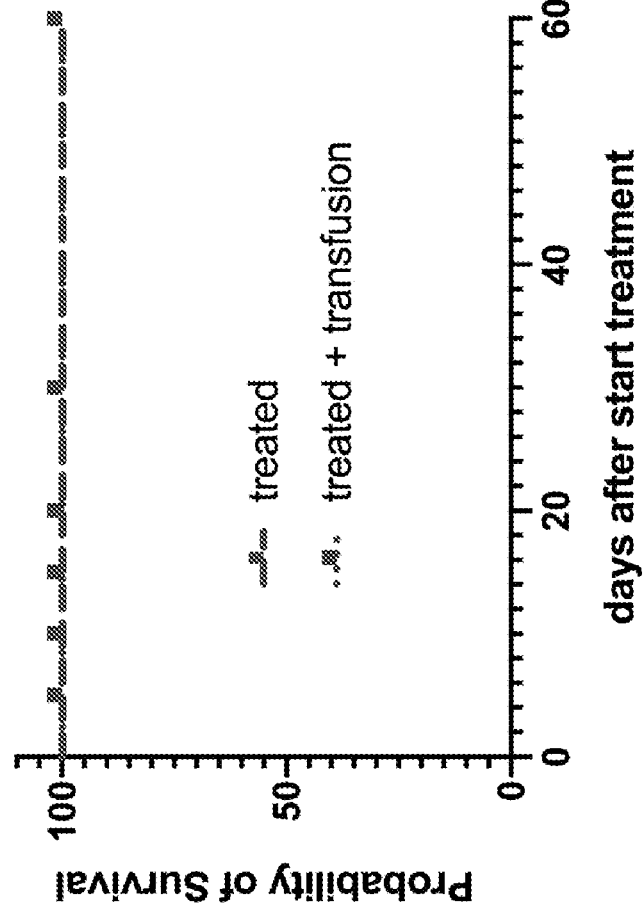
Figure 13:
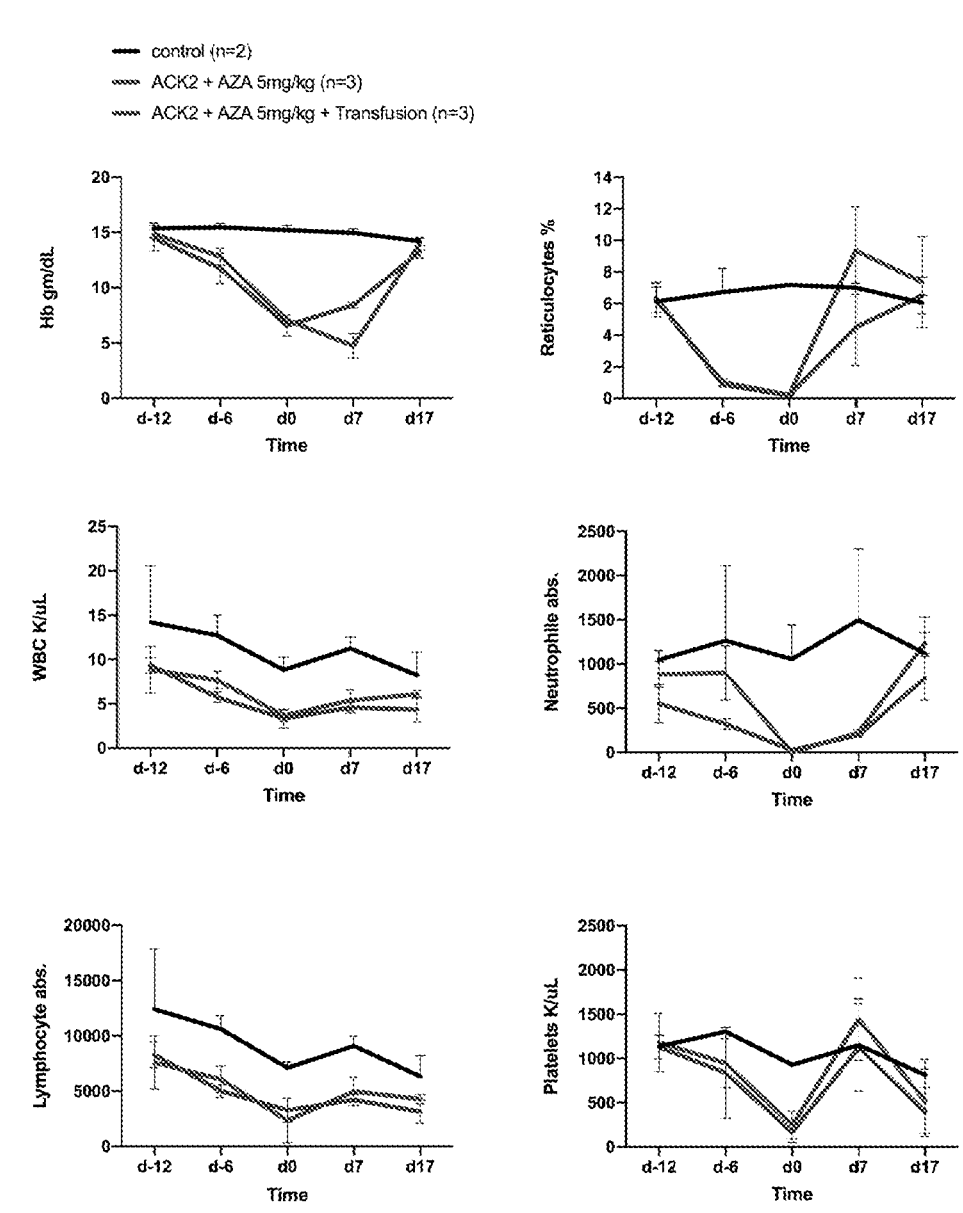

Anti-CD117 mAb ACK2 in combination with AZA augments depletion of HSC by inhibiting CD117/SCF signaling. It is well known that HSC survival depends on CD117/SCF signaling and it was previously shown that neutralizing SCF antibody mitigates hematopoietic recovery in the setting of hematopoietic stress following sublethal total body irradiation (TBI). Having determined that AZA depletes HSC by inducing cellular proliferation and apoptosis in vivo we next tested if blockade of CD117/SCF signaling in combination with AZA could lead to enhanced HSC depletion in vivo. ACK2 as a single dose of 500 μg was given 5 days prior treatment with AZA (FIG. 3A). This combination approach achieved bone marrow niche clearance at day 6 (FIG. 3B) and robust depletion in all HSPC compartments with significantly delayed recovery (compared to AZA alone) of MPP2, MPP3/4, ST-HSC, and LT-HSC, even 2 weeks after treatment discontinuation (FIG. 3C). There was no evidence that these populations mobilized to the spleen as there was a decrease of all HSC and MPP fractions in the spleen which, except ST-HSC, recovered by day 20 (FIG. 3C). In all mice treated with ACK2 and AZA, there was deep depletion of peripheral counts after treatment, but all lineages recovered from this pancytopenia by 17 days post treatment (FIG. 13C). Transfusion of whole blood was able to correct anemia and 100% survival rate was documented in both transfused- and non-transfused groups (FIG. 13A-C), suggesting the non-myeloablative nature of ACK2/AZA treatment.

Figure 14:
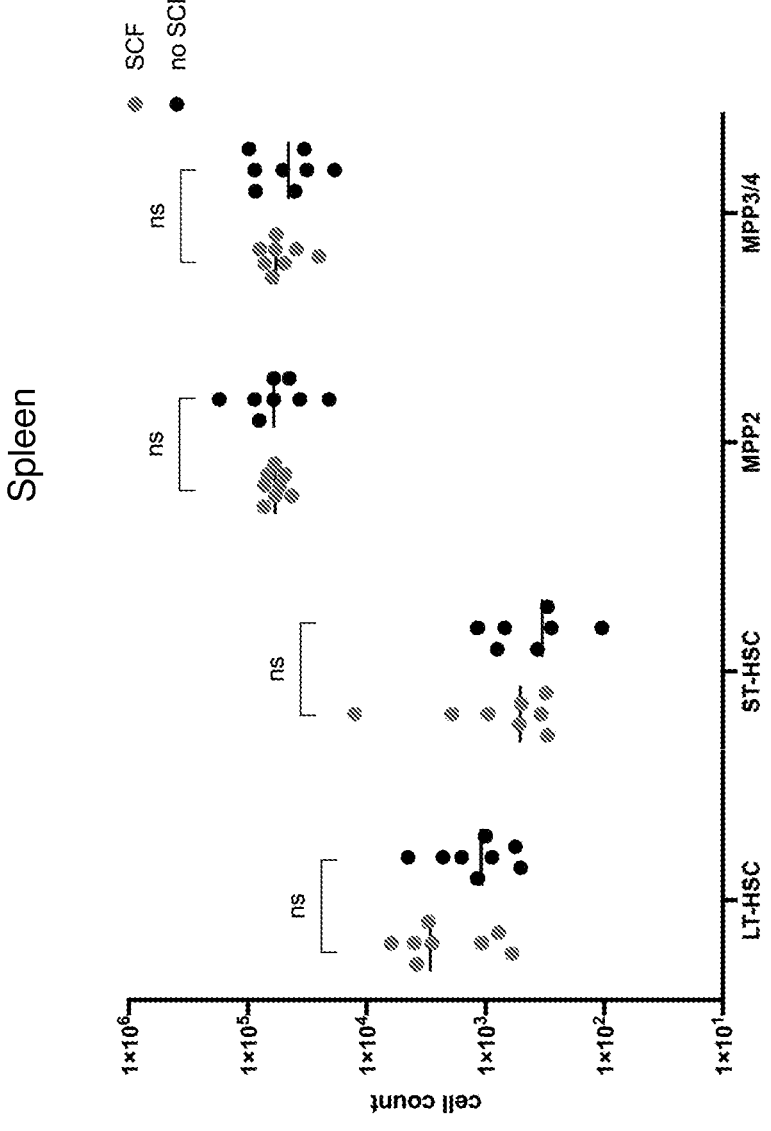
FIG. 14 shows absolute numbers of LT-HSC, ST-HSC, MPP2 and MPP3/4 in the spleen following treatment with ACK2+AZA with or without the addition of recombinant SCF. Analysis was performed on day 11 post start treatment with AZA5 mg/kg. Data were pooled from 2 independent experiments and represent mean±SD (n=8 per group). Statistics were calculated by Mann-Whitney test (ns=non-significant).
Figure 15:
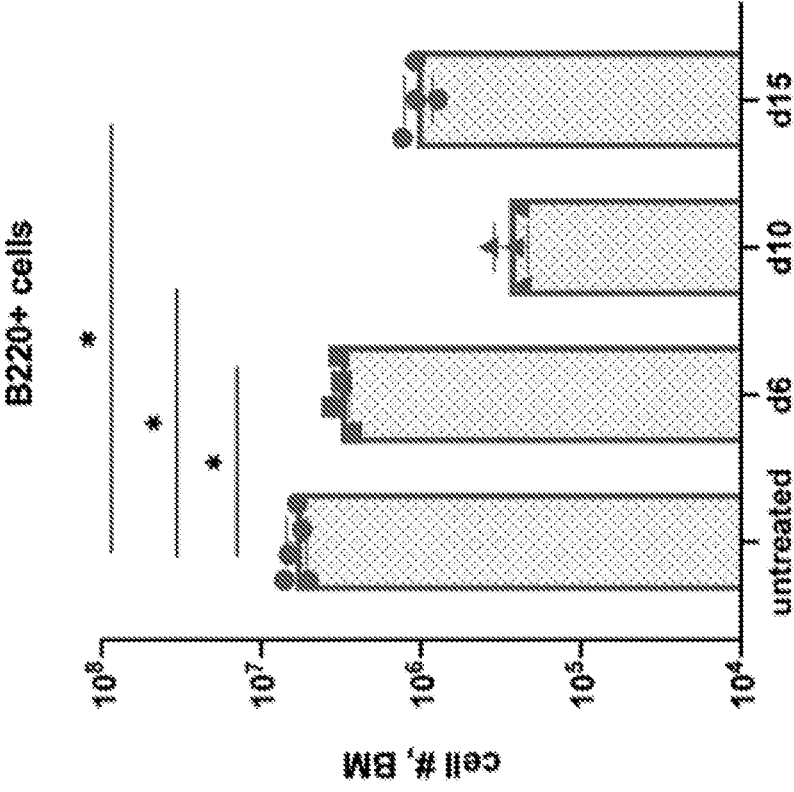
FIG. 15 shows AZA depletes mature B cells. C57BL/6 mice were injected with AZA in dose 5 mg/kg/d for 5 consecutive days. B220+ cells in the BM were assessed by flow cytometry. n=4 per group per timepoint; Statistics were calculated with Mann-Whitney test (*P<0.05).
Figure 16:
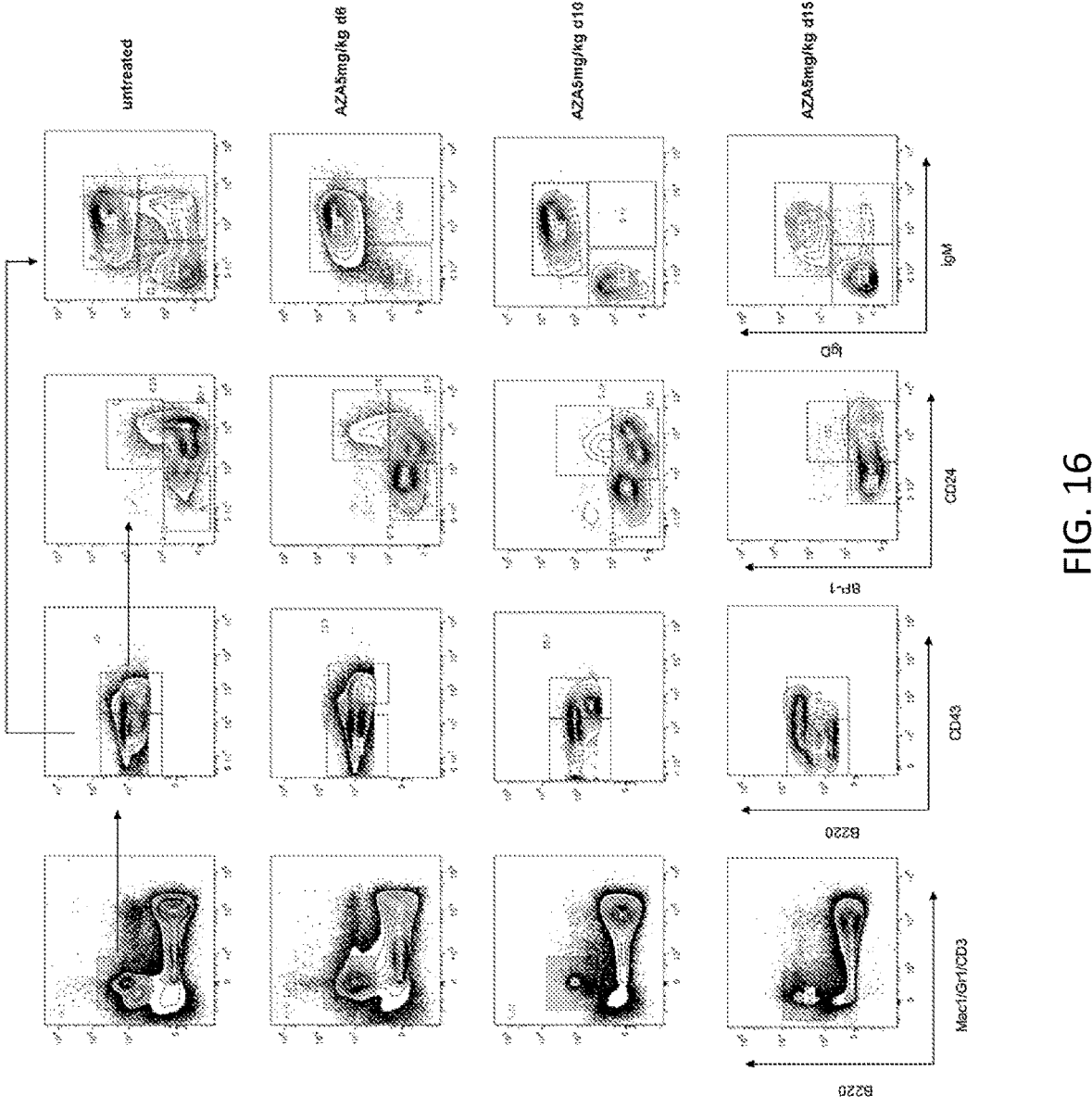
FIG. 16 shows 5-Azacytidine causes maturation block in B-cell development in the bone marrow. C57BL/6 mice were injected with AZA in dose 5 mg/kg/d for 5 consecutive days. B-cell lineage development stages in the BM was assessed by flow cytometry using Hardy profile (Fraction A-F). Representative flow cytometry plots at day 6, 10, 15 and 20 show maturation block at Fraction D and E in the treated mice as compared to normal B-cell maturation in the untreated control. Gated from live cells.

We next evaluated if blockade of CD117 with its ligand SCF by ACK2 was the cause of the prolonged depletion of HSC seen in mice treated with ACK2 plus AZA. We used 2B8 clone of CD117 mAb, which also binds mouse CD117, but only partially inhibits SCF binding to CD117 and does not lead to in vivo functional depletion of HSC. In contrast with single agent AZA or the combination of 2B8 with AZA, significant impairment in HSC recovery was observed only in the ACK2/AZA group (FIG. 3D). These data suggested that the synergistic effect of ACK2 and AZA on the depth and duration of HSC-depletion is dependent on the interaction of CD117 and SCF. To test this hypothesis, we treated immunocompetent mice with ACK2 and AZA, and also administered 1 µg of exogenous murine SCF for 5 consecutive days (FIG. 3E). SCF-treated mice showed faster recovery of LT-HSC in the bone marrow at day 11, with no changes in ST-HSC, MPP2 and MPP3/4 (FIG. 3F-G). Same tendency was observed in the spleen of treated mice, although increase in LT-HSC did not reach statistical significance (FIG. 14). These data demonstrate that the CD117/SCF interaction plays an important role in HSPC restoration following treatment with ACK2 and AZA.

Figure 4:
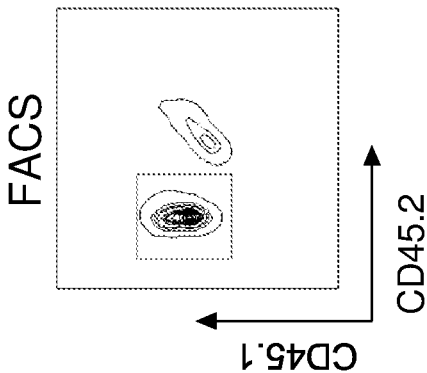
FIG. 4 shows ACK2 synergizes with AZA and permits engraftment of congenic hematopoietic stem cells in immunocompetent mice. A. Schematic of congenic transplantation protocol. B6 (H-2ᵇ, Thy1.1, CD45.1) mice were donors for B6 (H-2b, Thy1.1, CD45.1/CD45.2) recipients. ACK2 in dose 500 μg was injected 10 days prior transplantation and AZA was administered day −5 through day −1 at dose 2.5 and 5 mg/kg/d; chimerism analysis from peripheral blood was assessed by flow cytometry using CD45 marker to distinguish between donor and recipient total, myeloid (Gr1⁺Mac1⁺), B-cells (CD19⁺CD3⁻) and T-cells (CD19⁻CD3⁺). B. Higher levels of sustained multilineage donor engraftment in the combination groups in comparison to single agent ACK2 or AZA following transplantation of 20×10⁶ WBM cells. Data were pooled from 2 independent experiments and represent mean±SD (n=3-6 per group). C. ACK2 in combination with AZA 5 mg/kg/d enables sustained multilineage engraftment of 5×10⁴ FACS-sorted donor congenic Lin⁻Sca1⁺c-Kit⁺ cells (LSK). Data were pooled from 2 independent experiments and represent mean±SD (n=6-7 per group). D. Multilineage donor-derived chimerism in peripheral blood at 4, 8, 16 and 20 weeks following no conditioning or conditioning with AZA in dose 2.5 or 5 mg/kg/d for 5 consecutive days and transplantation of 15×10⁶ allogeneic WBM cells. Data represent mean±SD (n=3-4 per group).
Figure 4:
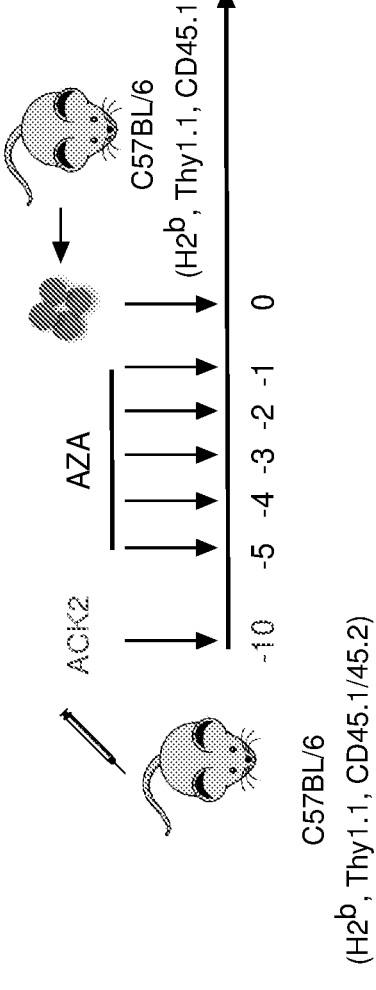
Figure 4:
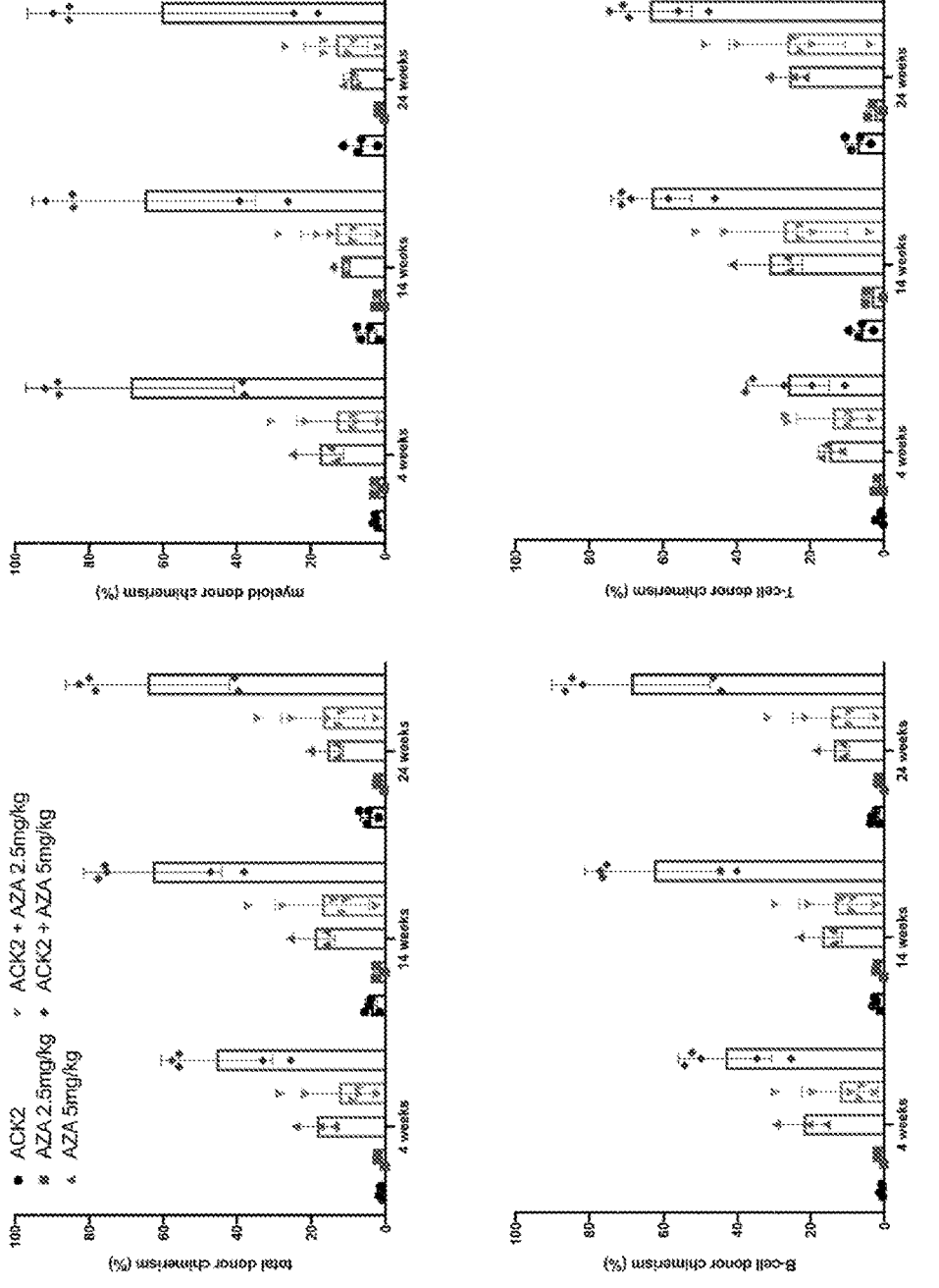
Figure 4:
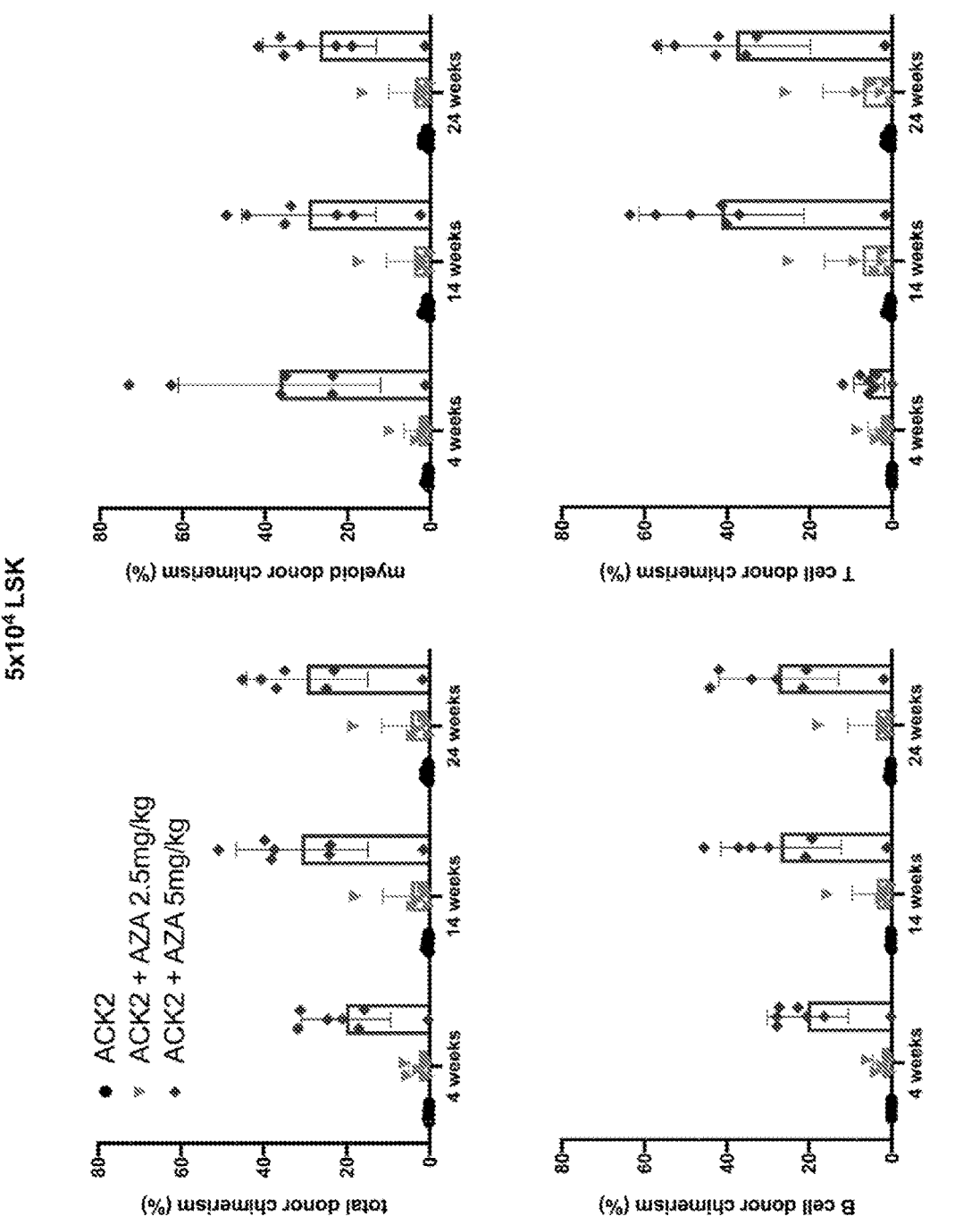

ACK2 in combination with AZA enables engraftment of purified congenic HSC in immunocompetent mice. Next, we tested if ACK2/AZA treatment would enable donor HSC engraftment in immunocompetent mice. Conditioning with ACK2 at day −10 was followed by AZA for 5 consecutive days (day −5 through day −1) and transplantation of $20 \times 10^6$ congenic WBM cells or $5 \times 10^4$ LSK (FIG. 4A). While ACK2 alone-conditioned mice showed donor engraftment <5%, and 5 days of AZA 2.5 mg/kg alone treatment does not enable stable engraftment of donor WBM, sustained multilineage donor chimerism was achieved with transplantation of WBM cells using ACK2 and 5 days of AZA 2.5 mg/kg conditioning (FIG. 4B). Conditioning with ACK2 plus 5 days of AZA 5 mg/kg lead to significantly increased stable multilineage donor chimerism levels (>50%). (FIG. 4B). Interestingly, single agent AZA 5 mg/kg enabled sustained donor engraftment with levels of myeloid donor chimerism between 10-15%, which served as a proof of principle that AZA can indeed clear HSC niches. Similar synergistic activity between ACK2 and AZA was achieved when sorted purified HSC (LSK) from congenic donors were transplanted following conditioning with ACK2 and 5 days of AZA 2.5 mg/kg or 5 mg/kg (FIG. 4C). ACK2 and 5 days of AZA 5 mg/kg was able to facilitate engraftment of purified HSC, suggesting that prolonged availability of HSC niches and competitional disadvantage of recipient HSC induced by the conditioning regimen are important for HSC engraftment across non-immunological barriers.

Figure 5:
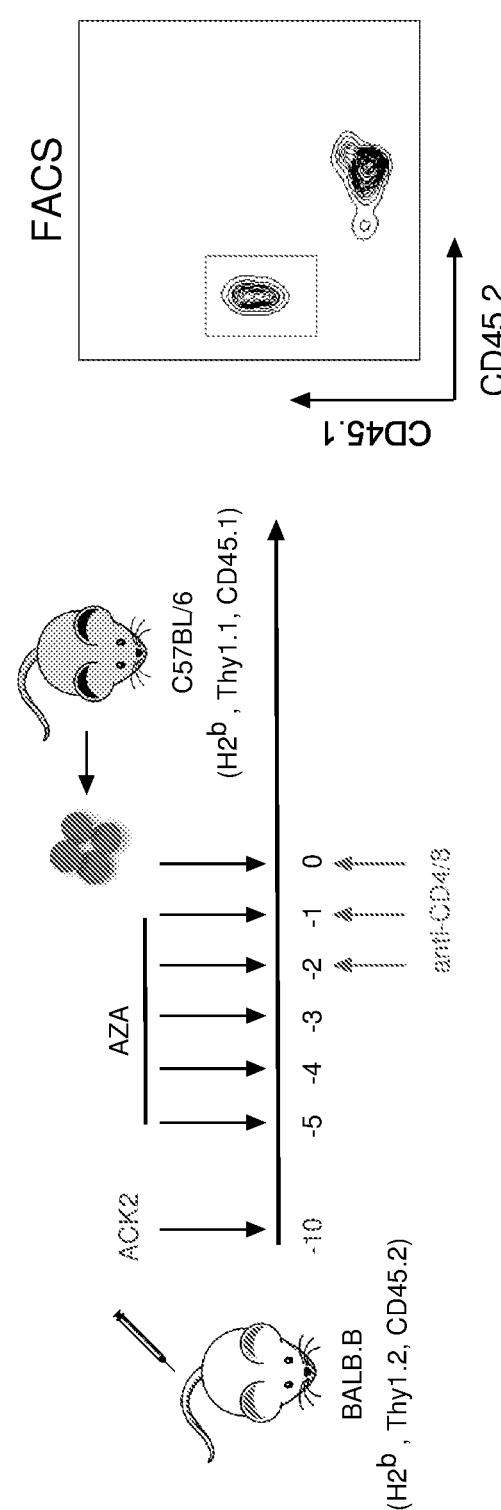
FIG. 5 shows ACK2 synergizes with AZA and permits engraftment of allogeneic HSC in immunocompetent mice. A. Schematic of allogeneic transplantation protocol. BALB.B mice (H-2$^b$, Thy1.2, CD45.2) were recipients for B6 donors (H-2b, Thy1.1, CD45.1); ACK2 was injected 10 days prior transplantation, AZA was administered days −5 through −1 in dose 2.5 or 5 mg/kg/d, anti-CD4/CD8 were injected in dose 100 μg at days −2, −1 and at the day of transplant (day 0); recipients received 15×10⁶ WBM cells or 5×10⁴ LSK at d0; chimerism analysis was assessed by flow cytometry using CD45 marker to distinguish between donor and recipient total, myeloid (Gr1⁺Mac1⁺), B-cells (CD19⁺CD3⁻) and T-cells (CD19⁻CD3⁺). B. Multilineage donor-derived chimerism after conditioning with ACK2, AZA 2.5 mg/kg, AZA 5 mg/kg or their combination and transplantation of 15×10⁶WBM cells. Chimerism levels from peripheral blood are shown at 4, 14 and 26 weeks post-HCT. Data represent mean±SD (n=4 per group). C. Multilineage donor-derived chimerism in peripheral blood at 4, 14 and 26 weeks following conditioning with single agent ACK2, single agent AZA 5 mg/kg/d or their combination and transplantation of 5×10⁴ Lin⁻ Sca1⁺c-Kit⁺ cells (LSK). Data represent mean±SD (n=3-5 per group) between the donor and recipient.
Figure 5:
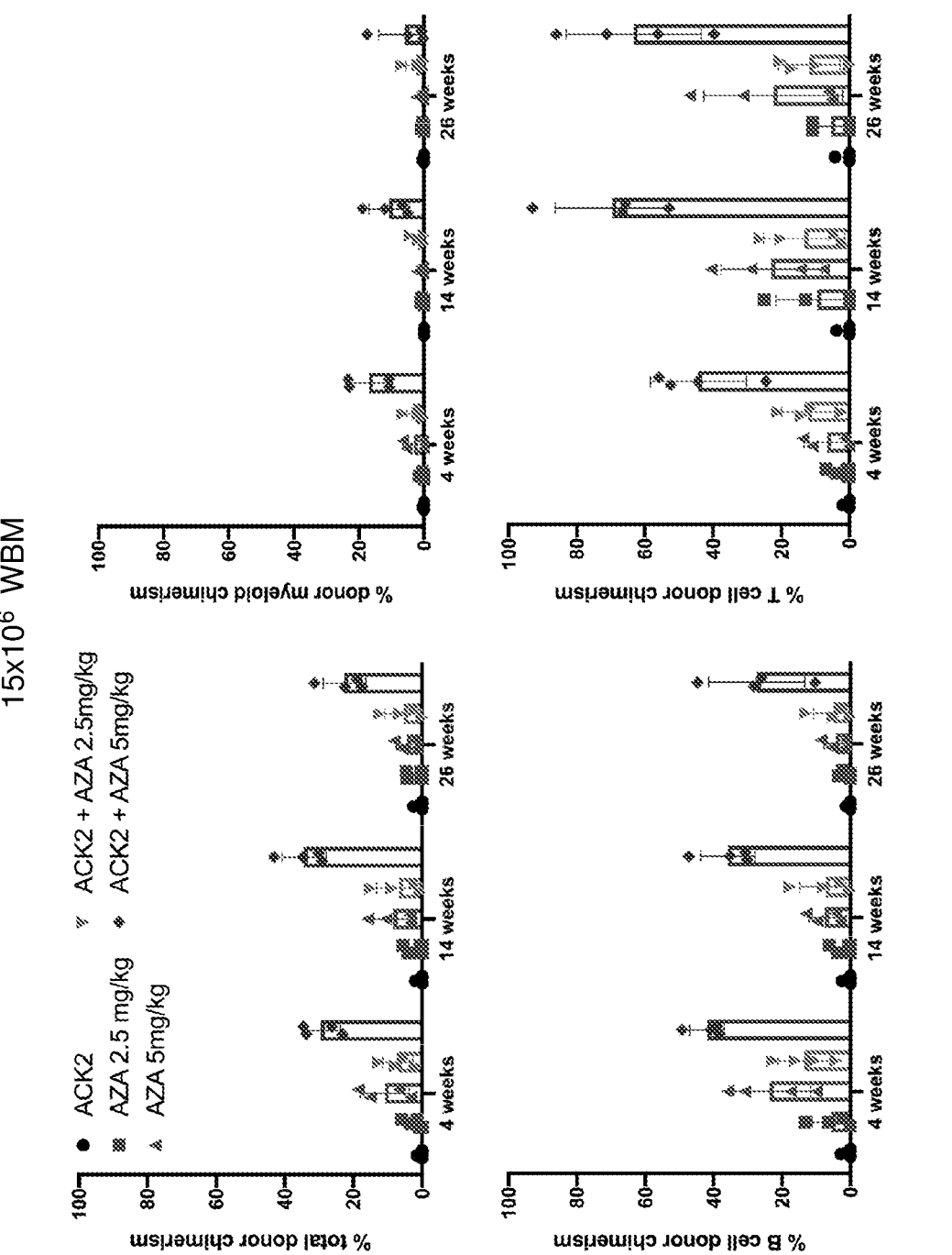
Figure 5:
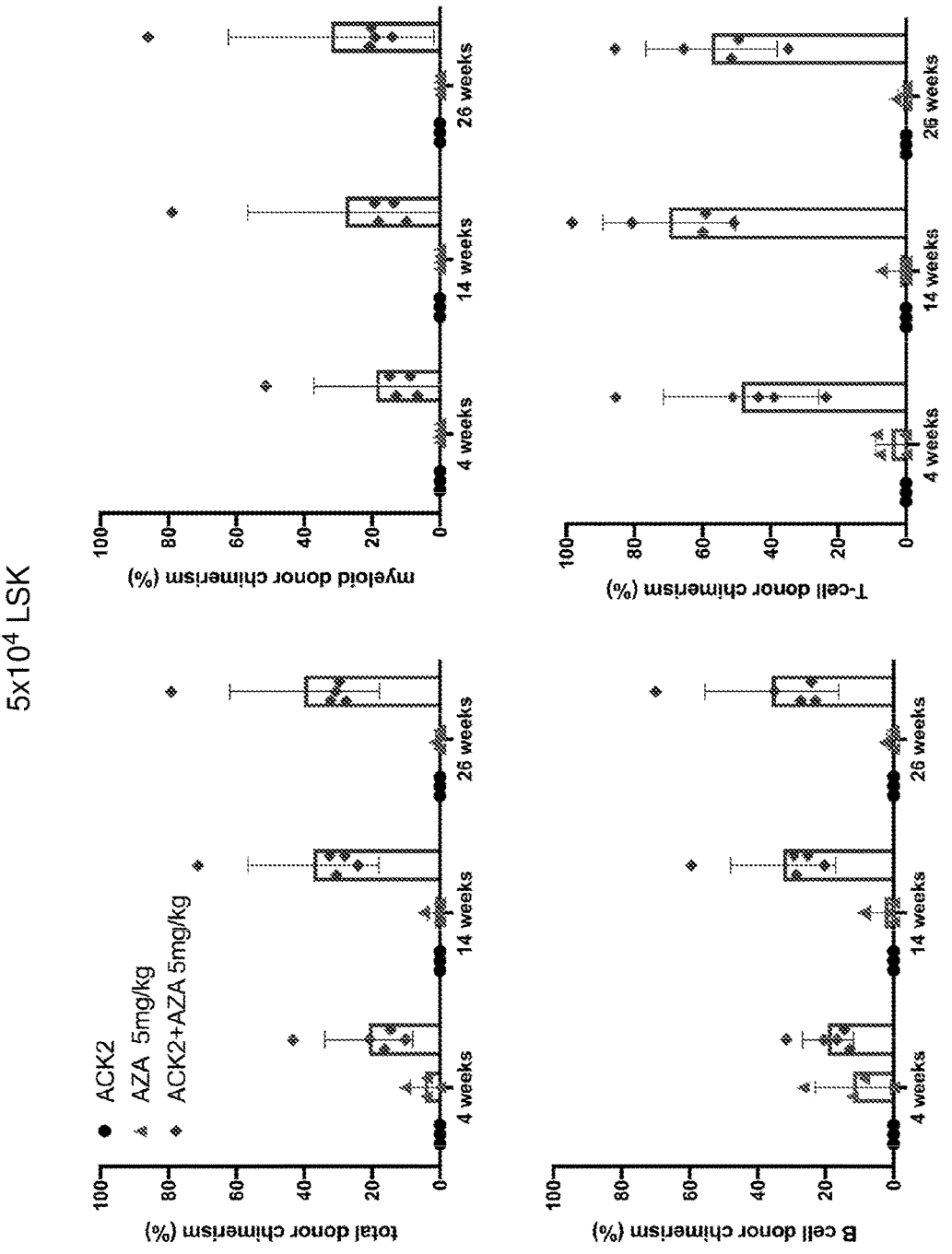

ACK2 in combination with AZA enables engraftment of purified allogeneic HSC in immunocompetent mice. Next, we tested if ACK2/AZA conditioning would enable engraftment of allogeneic HSC transplanted across minor-MHC barriers (FIG. 5A). $15 \times 10^6$ WBM cells from B6 donors (H-$2^b$, Thy1.1, CD45.1) were transplanted into BALB.B recipients (H-2b, Thy1.2, CD45.2) after conditioning with ACK2, AZA 2.5 mg/kg, AZA 5 mg/kg or their combination. In this model anti-CD4 and anti-CD8 monoclonal antibodies were administered for 3 consecutive days prior to donor cell transplantation to minimize immune-mediated rejection of the allogeneic donor cells. Similar to the congenic setting, successful donor engraftment was achieved when AZA was used at doses 5 mg/kg/d (FIG. 3B). Whereas total donor chimerism was noted to decrease in the AZA alone group, in the combination group levels of total donor chimerism remained stable at around 20% 26 weeks post HCT. Similar to WBM grafts, $5 \times 10^4$ purified HSC (LSK) showed long-term multilineage donor engraftment only in the combination group with levels of myeloid chimerism reaching >30%.

These studies show the novel finding that the hypomethylating agent, AZA, combined with an anti-CD117 antibody, ACK2, potently depletes recipient HSPC and allows donor HSC to engraft in mouse models. Anti-CD117 antibodies have recently reached the clinic as a new class of biologic agents capable of safely depleting HSPC, thereby opening marrow niche space, a requirement of all HCT conditioning regimens to achieve engraftment of donor allogeneic or autologous gene-corrected HSC. Current HCT relies on genotoxic modalities to achieve this HSC niche clearance, and the deleterious off-target effects of these agents have severely limited HCT to patients with few or no co-morbidities, and have excluded many others with diseases curable by HCT. By contrast, anti-CD117 antibodies act by targeted depletion of HSPC. Their specificity, outstanding safety profile, and unique mechanism of action make anti-CD117 antibodies ideal to use therapeutically to augment the activity of other HSPC-depleting modalities.

Our determination that AZA can be a therapeutic partner to augment the HSC depleting and engraftment capacity of a naked anti-CD117 antibody was surprising. Hypomethylating agents have not been previously used as components of conditioning for transplant. Although these agents have been shown to suppress myelopoiesis in the setting of minimal or no measurable malignant disease, (e.g., post-allogeneic HCT as maintenance therapy), the effect of these drugs on normal hematopoiesis has not been well studied. The depletion of normal HSC by AZA alone was unexpected because the vast majority (>95%) of HSC are non-cycling, and cytotoxicity by hypomethylating agents rely on incorporation of drug metabolites into DNA during S-phase. Direct toxicity reportedly occurs via irreversible binding of the incorporated drug metabolites to DNA methyltransferase (DNMT), and it is these DNMT-AZA adducts that are cytotoxic, rather than the hypomethylated state caused by this binding. Because cells with higher levels of DNMT are reported to be more susceptible to the toxic effects of hypomethylating agents and HSC have been shown to have high levels of maintenance DNMT1, HSC may have increased sensitivity to DNMT-inhibitors in the event that the drug gains access into the DNA.

Since most HSC are quiescent, we examined if AZA itself will induce HSC proliferation. We observed that consecutive in vivo dosing of AZA resulted in pronounced depletion of mature cells, and proliferation of HSC and MPP. In vitro assays confirmed that AZA, at concentrations equivalent to plasma levels observed in patients, was directly toxic to both mouse and human proliferating HSC. We thus hypothesize that AZA induces stress hematopoiesis, causing HSC to leave their quiescent state, and in the setting of proliferating HSC the drug exerts direct cytotoxic effects. It follows that sequential doses of the hypomethylating agent, as is given clinically, is required to obtain HSC depletion. However, we recognize that AZA's metabolites incorporate into both DNA and RNA, and there are likely additional AZA-mediated intra- and extracellular events that explain the drug's activity on normal and clonally abnormal hematopoietic cells.

Having noted that AZA induces HSPC death, and given that prior studies have shown that SCF can rescue hematopoiesis following irradiation-related injury, we hypothesized that the addition of a CD117 blocking antibody to AZA treatment might inhibit the restoration of AZA-injured HSC. Indeed, our studies using combined ACK2+AZA showed prolonged LT-HSC depletion, and administration of exogenous SCF to AZA+ACK2 treated mice resulted in faster recovery of LT-HSC. Furthermore, we tested LT-HSC depletion with AZA plus two different anti-CD117 antibodies, ACK2 and 2B8, which have differential ability to block hematopoiesis in vitro in the presence of SCF. In combination with AZA, ACK2 showed greater efficacy to deplete LT-HSC as compared to 2B8. Taken together, these findings support the important role of SCF/CD117 signal blockade in the synergy between ACK2 and AZA.

The clinical applications for this anti-CD117 antibody plus AZA combination are broad, spanning both non-malignant and malignant hematologic disorders. Based on the mechanisms of action and clinical experience, these two agents used as transplant conditioning are expected to have a substantially better safety profile compared to traditional alkylator or radiation-based regimens. Busulfan, the most commonly used alkylator in transplant, has well known acute and chronic toxicities, the latter of which are especially problematic for children. The acute risks of busulfan are pancytopenia, mucositis, seizure, and hepatic sinusoidal obstructive syndrome. Long-term sequelae include infertility, growth failure, pulmonary fibrosis, neurodevelopmental delays, and increased risk of cancer. By contrast, AZA's major toxicities of myelosuppression and gastrointestinal symptoms (e.g., nausea, vomiting) are acute. Long-term data on the effects of AZA in children are lacking, but the extensive experience with AZA in adults does not raise the same specter of irreversible tissue damage and mutagenesis compared to busulfan.

With regards to anti-CD117 agents, our group recently reported on the safety and efficacy of an anti-CD117 antibody, JSP191, used as single agent conditioning prior to allogeneic HCT in children with SCID. All patients tolerated JSP191 well, without safety issues, and all showed evidence of long-term HSC engraftment. For other nonmalignant diseases (e.g. sickle cell disease, thalassemia, Fanconi's anemia), patients routinely present to transplant with increased risk of transplant-related toxicities because of their inherent disease-specific co-morbidities including hepatic or renal dysfunction, and iron-overload. Importantly, achievement of mixed hematopoietic chimerism, in the order of >20%, is sufficient to provide curative benefit particularly for hemoglobinopathies. A safer pre-transplant conditioning regimen would permit more patients to qualify or electively pursue HCT as a curative option earlier in the disease course and significantly improve quality of life for long-term survivors of HCT.

These findings for hematologic malignancies include transplantation, but can extend to the utilization of this combination as a therapeutic regimen. For myeloid malignancies, elimination of leukemic stem cells (LSC) is essential for disease eradication. Despite the disease-modifying effects of AZA in patients with MDS, AML and CMML, single agent AZA is insufficient to eliminate LSC and therefore does not achieve durable remissions. By comparison, the combination of AZA with the B-cell lymphoma 2 (BCL-2) inhibitor Venetoclax or with the human anti-CD70 antibody have proved to be more efficacious in AML by synergistic targeting of LSC. We recently showed that the anti-CD117 mAb, JSP191, depletes human MDS HSC in MDS-xenografted mice. Future investigations will study combined anti-CD117 antibody plus AZA on the eradication of MDS and AML.

In summary, our studies provide a platform for the clinical utilization of a novel combination of anti-CD117 antibody plus AZA, which may prove to be of therapeutic benefit for malignant and non-malignant hematologic diseases in the near future.

REFERENCES

1. Ades L, Guardiola P, Socie G. Second malignancies after allogeneic hematopoietic stem cell transplantation: new insight and current problems. Blood Rev. 2002; 16(2):135-146.
2. Diaconescu R, Flowers C R, Storer B, et al. Morbidity and mortality with nonmyeloablative compared with myeloablative conditioning before hematopoietic cell transplantation from HLA-matched related donors. Blood. 2004; 104(5):1550-1558.
3. Socie G, Salooja N, Cohen A, et al. Nonmalignant late effects after allogeneic stem cell transplantation. Blood. 2003; 101(9):3373-3385.
4. Lowe T, Bhatia S, Somlo G. Second malignancies after allogeneic hematopoietic cell transplantation. Biol Blood Marrow Transplant. 2007; 13(10):1121-1134.
5. Kwon H S, Logan A C, Chhabra A, et al. Anti-human CD117 antibody-mediated bone marrow niche clearance in nonhuman primates and humanized NSG mice. Blood. 2019; 133(19):2104-2108.
6. Agarwal R, Dvorak C, Kwon H S, et al. Non-Genotoxic Anti-CD117 Antibody Conditioning Results in Successful Hematopoietic Stem Cell Engraftment in Patients with Severe Combined Immunodeficiency. Blood. 2019; 134 (Supplement_1):800.
7. Ikuta K, Ingolia D E, Friedman J, Heimfeld S, Weissman I L. Mouse hematopoietic stem cells and the interaction of c-kit receptor and steel factor. Int J Cell Cloning. 1991; 9(5):451-460.
8. Li C L, Johnson G R. Stem cell factor enhances the survival but not the self-renewal of murine hematopoietic long-term repopulating cells. Blood. 1994; 84(2): 408-414.
9. Czechowicz A, Kraft D, Weissman I L, Bhattacharya D. Efficient transplantation via antibody-based clearance of hematopoietic stem cell niches. Science. 2007; 318 (5854):1296-1299.
10. Pang W W, Czechowicz A, Logan A C, et al. Anti-CD117 antibody depletes normal and myelodysplastic syndrome human hematopoietic stem cells in xenografted mice. Blood. 2019; 133(19):2069-2078.
11. Czechowicz A, Palchaudhuri R, Scheck A, et al. Selective hematopoietic stem cell ablation using CD117-antibody-drug-conjugates enables safe and effective transplantation with immunity preservation. Nat Commun. 2019; 10(1):617.
12. Xue X, Pech N K, Shelley W C, Srour E F, Yoder M C, Dinauer M C. Antibody targeting KIT as pretransplantation conditioning in immunocompetent mice. Blood. 2010; 116(24):5419-5422.
13. Chhabra A, Ring A M, Weiskopf K, et al. Hematopoietic stem cell transplantation in immunocompetent hosts without radiation or chemotherapy. *Sci Transl Med.* 2016; 8(351):351ra105.

14. George B M, Kao K S, Kwon H S, et al. Antibody Conditioning Enables MHC-Mismatched Hematopoietic Stem Cell Transplants and Organ Graft Tolerance. *Cell Stem Cell.* 2019; 25(2):185-192 e183.

15. Silverman L R, Demakos E P, Peterson B L, et al. Randomized controlled trial of azacitidine in patients with the myelodysplastic syndrome: a study of the cancer and leukemia group B. *J Clin Oncol.* 2002; 20(10):2429-2440.

16. Fenaux P, Mufti G J, Hellstrom-Lindberg E, et al. Efficacy of azacitidine compared with that of conventional care regimens in the treatment of higher-risk myelodysplastic syndromes: a randomised, open-label, phase III study. *Lancet Oncol.* 2009; 10(3):223-232.

17. Dombret H, Seymour J F, Butrym A, et al. International phase 3 study of azacitidine vs conventional care regimens in older patients with newly diagnosed AML with >30% blasts. *Blood.* 2015; 126(3):291-299.

18. Tantravahi S K, Szankasi P, Khorashad J S, et al. A phase II study of the efficacy, safety, and determinants of response to 5-azacitidine (Vidaza®) in patients with chronic myelomonocytic leukemia. *Leuk Lymphoma.* 2016; 57(10):2441-2444.

19. Drummond M W, Pocock C, Boissinot M, et al. A multi-centre phase 2 study of azacitidine in chronic myelomonocytic leukaemia. *Leukemia.* 2014; 28(7): 1570-1572.

20. Khan R, Schmidt-Mende J, Karimi M, et al. Hypomethylation and apoptosis in 5-azacytidine-treated myeloid cells. *Exp Hematol.* 2008; 36(2):149-157.

21. Chiappinelli K B, Strissel P L, Desrichard A, et al. Inhibiting DNA Methylation Causes an Interferon Response in Cancer via dsRNA Including Endogenous Retroviruses. *Cell.* 2017; 169(2):361.

22. Curik N, Burda P, Vargova K, et al. 5-azacitidine in aggressive myelodysplastic syndromes regulates chromatin structure at PU.1 gene and cell differentiation capacity. *Leukemia.* 2012; 26(8):1804-1811.

23. Christman J K, Mendelsohn N, Herzog D, Schneiderman N. Effect of 5-azacytidine on differentiation and DNA methylation in human promyelocytic leukemia cells (HL-60). *Cancer Res.* 1983; 43(2):763-769.

24. Wenk C, Garz A K, Grath S, et al. Direct modulation of the bone marrow mesenchymal stromal cell compartment by azacitidine enhances healthy hematopoiesis. *Blood Adv.* 2018; 2(23):3447-3461.

25. Ehx G, Fransolet G, de Leval L, et al. Azacytidine prevents experimental xenogeneic graft-versus-host disease without abrogating graft-versus-leukemia effects. *Oncoimmunology.* 2017; 6(5):e1314425.

26. Unnikrishnan A, Papaemmanuil E, Beck D, et al. Integrative Genomics Identifies the Molecular Basis of Resistance to Azacitidine Therapy in Myelodysplastic Syndromes. *Cell Rep.* 2017; 20(3):572-585.

27. Marcucci G, Silverman L, Eller M, Lintz L, Beach C L. Bioavailability of azacitidine subcutaneous versus intravenous in patients with the myelodysplastic syndromes. *J Clin Pharmacol.* 2005; 45(5):597-602.

28. Domen J, Weissman I L. Hematopoietic stem cells need two signals to prevent apoptosis; BCL-2 can provide one of these, Kitl/c-Kit signaling the other. *J Exp Med.* 2000; 192(12):1707-1718.

29. Neta R, Williams D, Selzer F, Abrams J. Inhibition of c-kit ligand/steel factor by antibodies reduces survival of lethally irradiated mice. *Blood.* 1993; 81(2):324-327.

30. Maples K T, Sabo R T, McCarty J M, Toor A A, Hawks K G. Maintenance azacitidine after myeloablative allogeneic hematopoietic cell transplantation for myeloid malignancies. *Leuk Lymphoma.* 2018; 59(12):2836-2841.

31. de Lima M, Giralt S, Thall P F, et al. Maintenance therapy with low-dose azacitidine after allogeneic hematopoietic stem cell transplantation for recurrent acute myelogenous leukemia or myelodysplastic syndrome: a dose and schedule finding study. *Cancer.* 2010; 116(23):5420-5431

32. Wilson A, Laurenti E, Oser G, et al. Hematopoietic stem cells reversibly switch from dormancy to self-renewal during homeostasis and repair. *Cell.* 2008; 135(6):1118-1129.

33. Juttermann R, Li E, Jaenisch R. Toxicity of 5-aza-2'-deoxycytidine to mammalian cells is mediated primarily by covalent trapping of DNA methyltransferase rather than DNA demethylation. *Proc Natl Acad Sci USA.* 1994; 91(25):11797-11801.

34. Tadokoro Y, Ema H, Okano M, Li E, Nakauchi H. De novo DNA methyltransferase is essential for self-renewal, but not for differentiation, in hematopoietic stem cells. *J Exp Med.* 2007; 204(4):715-722.

35. Lu L J, Randerath K. Mechanism of 5-azacytidine-induced transfer RNA cytosine-5-methyltransferase deficiency. *Cancer Res.* 1980; 40(8 Pt 1):2701-2705.

36. Glazer R I, Peale A L, Beisler J A, Abbasi M M. The effect of 5-azacytidine and dihydro-5-azacytidine on nuclear ribosomal RNA and poly(A) RNA synthesis in L1210 cells in vitro. *Mol Pharmacol.* 1980; 17(1):111-117.

37. Schuening F G, Appelbaum F R, Deeg H J, et al. Effects of recombinant canine stem cell factor, a c-kit ligand, and recombinant granulocyte colony-stimulating factor on hematopoietic recovery after otherwise lethal total body irradiation. *Blood.* 1993; 81(1):20-26.

38. Liebmann J, DeLuca A M, Epstein A, Steinberg S M, Morstyn G, Mitchell J B. Protection from lethal irradiation by the combination of stem cell factor and tempol. *Radiat Res.* 1994; 137(3):400-404.

39. Shenoy S, Angelucci E, Arnold S D, et al. Current Results and Future Research Priorities in Late Effects after Hematopoietic Stem Cell Transplantation for Children with Sickle Cell Disease and Thalassemia: A Consensus Statement from the Second Pediatric Blood and Marrow Transplant Consortium International Conference on Late Effects after Pediatric Hematopoietic Stem Cell Transplantation. *Biol Blood Marrow Transplant.* 2017; 23(4):552-561.

40. Fitzhugh C D, Cordes S, Taylor T, et al. At least 20% donor myeloid chimerism is necessary to reverse the sickle phenotype after allogeneic HSCT. *Blood.* 2017; 130(17):1946-1948.

41. Thomas D, Majeti R. Biology and relevance of human acute myeloid leukemia stem cells. *Blood.* 2017; 129 (12):1577-1585.

42. Craddock C, Quek L, Goardon N, et al. Azacitidine fails to eradicate leukemic stem/progenitor cell populations in patients with acute myeloid leukemia and myelodysplasia. *Leukemia.* 2013; 27(5):1028-1036.

43. DiNardo C D, Pratz K W, Letai A, et al. Safety and preliminary efficacy of venetoclax with decitabine or azacitidine in elderly patients with previously untreated acute myeloid leukaemia: a non-randomised, open-label, phase 1 b study. *Lancet Oncol.* 2018; 19(2):216-228.

44. Pollyea D A, Stevens B M, Jones C L, et al. Veneto-clax with azacitidine disrupts energy metabolism and targets leukemia stem cells in patients with acute myeloid leukemia. *Nat Med.* 2018; 24(12):1859-1866.
45. Riether C, Pabst T, Hopner S, et al. Targeting CD70 with cusatuzumab eliminates acute myeloid leukemia stem cells in patients treated with hypomethylating agents. *Nat Med.* 2020.

Each publication cited in this specification is hereby incorporated by reference in its entirety for all purposes.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

What is claimed is:

1. A method for providing hematopoietic stem cell engraftment in a mammalian subject, the method comprising:
   (i) administering to the subject an effective dose of an anti-CD117 antibody;
   (ii) administering to the subject an effective dose of a hypomethylating agent; and
   (iii) infusing a cellular composition comprising exogenous hematopoietic stem cells to the subject,
   wherein the administration of the anti-CD117 antibody and the administration of the hypomethylating agent ablate targeted endogenous hematopoietic stem cells in the subject, and the exogenous hematopoietic stem cells are engrafted to the subject in the absence of myeloablative conditioning.

2. The method of claim 1, wherein the anti-CD117 antibody is a monoclonal antibody, and optionally is an aglycosylated IgG antibody.

3. The method of claim 2, wherein the dose of the anti-CD117 antibody is from about 0.1 mg/kg to about 25 mg/kg.

4. The method of claim 2, wherein the anti-CD117 antibody is administered as a single dose.

5. The method of claim 1, wherein the hypomethylating agent blocks the activity of DNA methyltransferase, and wherein the hypomethylating agent is a cytosine analog.

6. The method of claim 5, wherein the hypomethylating agent is 5-azacytidine, decitabine, guadecitabine, or 5-fluro-2'-deoxycytidine.

7. The method of claim 6, wherein the daily dose of the hypomethylating agent is from about 0.1 mg/kg to about 10 mg/kg.

8. The method of claim 1, wherein the hypomethylating agent is administered daily for a period of from 1 to 9 days, or for a period of 5 days.

9. The method of claim 1, wherein the hypomethylating agent and the anti-CD117 antibody are administered concomitantly.

10. The method of claim 1, wherein the hypomethylating agent is administered subsequent to the administration of the anti-CD117 antibody, and the interval of time between administration of the anti-CD117 antibody and administration of the hypomethylating agent is between 1 and 10 days.

11. The method of claim 1, wherein the infusion of the cellular composition comprising the exogenous hematopoietic stem cells is performed from after about 12 hours to after about 10 days when the administration of the hypomethylating agent is completed.

12. The method of claim 1, wherein the exogenous hematopoietic stem cells are autologous or allogeneic relative to the subject, and are optionally genetically engineered ex vivo.

13. The method of claim 1, wherein the exogenous hematopoietic stem cells are obtained from bone marrow, cord blood, or peripheral blood and selected for CD34+ expression; optionally wherein the cellular composition comprises at least 50% CD34+ cells.

14. The method of claim 13, wherein the cellular composition comprises at least 105 CD34+ cells/kg of recipient body weight.

15. The method of claim 1, wherein the subject has a hematologic malignancy, a blood disorder, or has received an organ transplant from the same donor of the hematopoietic stem cells.

16. A method of treatment for a hematologic malignancy in a subject, the method comprising:
   (i) administering to the subject an effective dose of an anti-CD117 antibody; and
   (ii) administering to the subject an effective dose of a hypomethylating agent,
   wherein the administration of the anti-CD117 antibody and the administration of the hypomethylating agent ablate targeted endogenous hematopoietic stem cells in the subject.

17. The method of claim 16, wherein the anti-CD117 antibody is an aglycosylated IgG antibody, and wherein the dose of the anti-CD117 antibody is from about 0.1 mg/kg to about 25 mg/kg.

18. The method of claim 16, wherein the hypomethylating agent is 5-azacytidine, decitabine, guadecitabine, or 5-fluro-2'-deoxycytidine, and wherein the daily dose of the hypomethylating agent is from about 0.1 mg/kg to about 10 mg/kg.

19. The method of claim 16, wherein the hematologic malignancy is a leukemia or pre-leukemia.

20. The method of claim 19, wherein the hematologic malignancy is myelodysplastic syndrome (MDS), acute myelogenous leukemia (AML), or chronic myelomonocytic leukemia (CMML).

* * * * *